(12) United States Patent
Traynelis et al.

(10) Patent No.: US 10,273,214 B2
(45) Date of Patent: *Apr. 30, 2019

(54) SUBUNIT SELECTIVE NMDA RECEPTOR POTENTIATORS FOR THE TREATMENT OF NEUROLOGICAL CONDITIONS

(71) Applicant: EMORY UNIVERSITY, Atlanta, GA (US)

(72) Inventors: Stephen F. Traynelis, Decatur, GA (US); Dennis C. Liotta, Atlanta, GA (US); Rose M. Santangelo, Decatur, GA (US); Ethel C. Garnier, Tucker, GA (US)

(73) Assignee: Emory University, Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/292,957

(22) Filed: Jun. 2, 2014

(65) Prior Publication Data

US 2014/0275529 A1    Sep. 18, 2014

Related U.S. Application Data

(63) Continuation of application No. 13/146,201, filed as application No. PCT/US2010/022439 on Jan. 28, 2010, now Pat. No. 8,822,462.

(60) Provisional application No. 61/147,897, filed on Jan. 28, 2009.

(51) Int. Cl.

| | |
|---|---|
| *C07D 217/16* | (2006.01) |
| *C07D 491/056* | (2006.01) |
| *C07D 409/06* | (2006.01) |
| *C07D 405/06* | (2006.01) |
| *C07D 401/06* | (2006.01) |
| *C07D 413/06* | (2006.01) |
| *C07D 409/04* | (2006.01) |
| *C07D 401/04* | (2006.01) |
| *C07D 277/34* | (2006.01) |
| *C07D 263/58* | (2006.01) |
| *C07D 239/88* | (2006.01) |
| *C07D 215/22* | (2006.01) |
| *C07D 209/08* | (2006.01) |

(52) U.S. Cl.
CPC ......... *C07D 217/16* (2013.01); *C07D 209/08* (2013.01); *C07D 215/22* (2013.01); *C07D 239/88* (2013.01); *C07D 263/58* (2013.01); *C07D 277/34* (2013.01); *C07D 401/04* (2013.01); *C07D 401/06* (2013.01); *C07D 405/06* (2013.01); *C07D 409/04* (2013.01); *C07D 409/06* (2013.01); *C07D 413/06* (2013.01); *C07D 491/056* (2013.01)

(58) Field of Classification Search
CPC ............... C07D 217/16; C07D 409/06; C07D 491/056; C07D 405/06; C07D 277/34; C07D 209/08; C07D 215/22; C07D 239/88; C07D 263/58; C07D 401/04; C07D 401/06; C07D 409/04; C07D 413/06

USPC ............. 544/128; 549/90, 146; 546/90, 146
See application file for complete search history.

(56) References Cited

U.S. PATENT DOCUMENTS

| | | |
|---|---|---|
| 4,522,811 A | 6/1985 | Eppstein et al. |
| 5,880,972 A | 3/1999 | Horlbeck |
| 6,087,186 A | 7/2000 | Cargill et al. |
| 6,184,223 B1 | 2/2001 | Kahn et al. |
| 2002/0143014 A1 | 10/2002 | Beck et al. |
| 2007/0037810 A1 | 2/2007 | Nunes et al. |
| 2008/0234237 A1 | 9/2008 | Maddaford et al. |

FOREIGN PATENT DOCUMENTS

| | | | |
|---|---|---|---|
| WO | 199300123 | 1/1993 | |
| WO | 2005027882 A1 | 3/2005 | |
| WO | WO2005027882 A1 * | 3/2005 | |
| WO | WO 2005027882 A1 * | 3/2005 | ............. A61K 31/00 |
| WO | WO-2005027882 A1 * | 3/2005 | ............. A61K 31/00 |

OTHER PUBLICATIONS

STN Compound CAS Entry Dates.*
RN680604-63-1 (available May 7, 2004).*
RN486427-17-2 (available Feb. 6, 2003).*
RN486427-20-7 (available Feb. 6, 2003).*
RN486426-39-5 (Year: 2003).*
Akazawa et al., (1994), "Differential expression of five N-methyl-D-aspartate receptor subunit mRNAs in the aerebellum of developing and adult rats.", The Journal of Comparative Neurology, 347(1): 150-160.
Akbarian et al., (1996), "Selective alterations in gene expression for NMDA receptor subunits in prefrontal cortex of schizophrenics.", The Journal of Neuroscience, 16(1): 19-30.
Andreasen et al., (1997), "Hypofrontality in schizophrenia: distributed dysfunctional circuits in neuroleptic-naive patients.", The Lancet, 349(9067): 1730-1734.
Arathoon et al., (1981), "Uptake of amino acids and glucose by BHK 21 clone 13 suspension cells during cell growth.", Developments in biological standardization, 50: 145.
Binshtok et al., (2006), "NMDA Receptors in Layer 4 Spiny Stellate Cells of the Mouse Barrel Cortex Contain the NR2C Subunit.", The Journal of Neuroscience, 26(2): 708-715.

(Continued)

*Primary Examiner* — Rachael E Bredefeld
*Assistant Examiner* — Ibrahim D Bori
(74) *Attorney, Agent, or Firm* — Emory Patent Group

(57) ABSTRACT

Provided are compounds, pharmaceutical compositions and methods of treating or preventing disorders associated with NMDA receptor activity, including schizophrenia, Parkinson's disease, cognitive disorders, depression, neuropathic pain, stroke, traumatic brain injury, epilepsy, and related neurologic events or neurodegeneration. Compounds of the general Formulas A-J, and pharmaceutically acceptable salts, esters, prodrugs or derivatives thereof are disclosed.

4 Claims, 4 Drawing Sheets

(56) References Cited

OTHER PUBLICATIONS

Brauner-Osborne et al., (2000), "Ligands for glutamate receptors: design and therapeutic prospects.", Journal of medicinal chemistry, 43(14): 2609-2645.
Buller et al., (1994), "The molecular basis of NMDA receptor subtypes: native receptor diversity is predicted by subunit composition.", The Journal of Neuroscience, 14(9): 5471-5484.
Cao et al., (2007), "Maintenance of superior learning and memory function in NR2B transgenic mice during ageing.", European Journal of Neuroscience, 25(6): 1815-1822.
Colonnese et al., (2005), "NMDA Receptor Currents Suppress Synapse Formation on Sprouting Axons in Vivo.", The Journal of Neuroscience, 25(5): 1291-1303.
Colonnese et al., (2006), "Developmental period for N-methyl-D-aspartate (NMDA) receptor-dependent synapse elimination correlated with visuotopic map refinement.", The Journal of Comparative Neurology, 494(5): 738-751.
Coyle et al., (2003), "Converging Evidence of NMDA Receptor Hypofunction in the Pathophysiology of Schizophrenia.", Annals of the New York Academy of Sciences, 1003(1): 318-327.
Coyle et al., (2004), "The NMDA receptor glycine modulatory site: a therapeutic target for improving cognition and reducing negative symptoms in schizophrenia.", Psychopharmacology, 174(1): 32-38.
Cull-Candy et al., (1998), "NMDA receptor diversity in the cerebellum: identification of subunits contributing to functional receptors.", Neuropharmacology, 37(10-11): 1369-1380.
Depoortere et al., (2005), "Neurochemical, Electrophysiological and Pharmacological Profiles of the Selective Inhibitor of the Glycine Transporter-1 SSR504734, a Potential New Type of Antipsychotic.", Neuropsychopharmacology, 30(11): 1963-1985.
Dingledine et al., (1999), "The Glutamate Receptor Ion Channels.", Pharmacological Reviews, 51(1): 7-62.
Dirnagl et al., (1999), "Pathobiology of ischaemic stroke: an integrated view.", Trends in Neurosciences, 22(9): 391-397.
Dravid et al., (2010), "Structural Determinants of d-Cycloserine Efficacy at the NR1/NR2C NMDA Receptors.", The Journal of Neuroscience, 30(7): 2741-2754.
Dunah et al., (1996), "Regional and Ontogenic Expression of the NMDA Receptor Subunit NR2D Protein in Rat Brain Using a Subunit-Specific Antibody.", Journal of Neurochemistry, 67(6): 2335-2345.
Dunah et al., (1998), "Subunit Composition of N-Methyl-d-aspartate Receptors in the Central Nervous System that contain the NR2D Subunit.", Molecular Pharmacology, 53(3): 429-437.
Dunah et al., (2003), "Subcellular segregation of distinct heteromeric NMDA glutamate receptors in the striatum.", Journal of Neurochemistry, 85(4): 935-943.
Erreger et al., (2005), "Subunit-specific gating controls rat NR1/NR2A and NR1/NR2B NMDA Channel kinetics and synaptic signalling profiles", The Journal of Physiology, 563(2): 345-358.
Erreger et al., (2005). "Mechanism of Partial Agonism at NMDA Receptors for a Conformationally Restricted Glutamate Analog.", The Journal of Neuroscience, 25(34): 7858-7866.
Froemke et al., (2005), "Spike-timing-dependent synaptic plasticity depends on dendritic location.", Nature, 434 (7030): 221-225.
Goff et al., (1999), "A placebo-controlled crossover trial of d-cycloserine added to clozapine in patients with schizophrenia.", Biological Psychiatry, 45(4): 512-514.
Goff et al., (2008), "Once-weekly d-cycloserine effects on negative symptoms and cognition in schizophrenia: An exploratory study", Schizophrenia Research, 106(2-3): 320-327.
Gremmen et al., (2001), "Enantiopure tetrahydroisoquinolines via N-sulfinyl Pictet—Spengler reactions.", Tetrahedron Letters, 42(50): 8885-8888.
Hallett et al., (2004), "Rationale for and use of NMDA receptor antagonists in Parkinson's disease.", Pharmacology & Therapeutics, 102(2): 155-174.
Hansen et al., (2008), "Pharmacological Characterization of Ligands at Recombinant NMDA Receptor Subtypes by Electrophysiological Recordings and Intracellular Calcium Measurements.", Combinatorial Chemistry & High Throughput Screening, 11(4): 304-315.
Heresco-Levy, U., (2005), "Glutamatergic neurotransmission modulators as emerging new drugs for schizophrenia.", Expert Opinion on Emerging Drugs, 10(4): 827-844.
Hofmann et al., (2006), "Augmentation of exposure therapy with d-cycloserine for social anxiety disorder.", Archives of General Psychiatry, 63(3): 298-304.
Hofmann et al., (2006), "Augmentation Treatment of Psychotherapy for Anxiety Disorders with D-Cycloserine.", CNS Drug Reviews, 12(3-4): 208-217.
Horak et al., (2004), "Molecular Mechanism of Pregnenolone Sulfate Action at NR1/NR2B Receptors", The Journal of Neuroscience, 24(46): 10318-10325.
Horak et al., (2006), "Subtype-dependence of N-methyl-d-aspartate receptor modulation by pregnenolone sulfate.", Neuroscience, 137(1): 93-102.
Javitt et al., (1991), "Recent advances in the phencyclidine model of schizophrenia.", Am J Psychiatry, 148(10): 1301-1308.
Javitt et al., (1994), "Amelioration of negative symptoms in schizophrenia by glycine.", The American Journal of Psychiatry, vol. 151(8): 1234-1236.
Javitt, D. C., (2007), "Glutamate and Schizophrenia: Phencyclidine, N-Methyl-d-Aspartate Receptors, and Dopamine—Glutamate Interactions.", International Review of Neurobiology., A. D. Anissa and G. Olivier, Academic Press., vol. 78: 69-108.
Jorgensen et al., (1995), "Outcome and time course of recovery in stroke. Part II: Time course of recovery. The copenhagen stroke study.", Archives of Physical Medicine and Rehabilitation, 76(5): 406-412.
Kampa et al., (2006), "Requirement of dendritic calcium spikes for induction of spike-timing-dependent synaptic plasticity.", The Journal of Physiology, 574(1): 283-290.
Kanemitsu et al., (2006), "Catalytic Asymmetric Synthesis of (R)-(−)-Calycotomine, (S)-(−)-Salsolidine and (S)-(−)-Carnegine.", Synlett, 2006(10): 1595-1597.
Karadottir et al., (2005), "NMDA receptors are expressed in oligodendrocytes and activated in ischaemia.", Nature, 438(7071): 1162-1166.
Krystal et al., (2002), "Effects of nmda receptor antagonists: Implications for the pathophysiology of schizophrenia.", Archives of General Psychiatry, 59(7): 663-664.
Kushner et al., (2007), "D-Cycloserine Augmented Exposure Therapy for Obsessive-Compulsive Disorder.", Biological Psychiatry, 62(8): 835-838.
Labie et al., (2010), "The involvement of the NMDA receptor d-serine/glycine site in the pathophysiology and treatment of schizophrenia.", Neuroscience & Biobehavioral Reviews, 34(3): 351-372.
Langlois et al., (2006), "Traumatic brain injury in the United States: emergency department visits, hospitalizations, and deaths.", Atlanta (GA): Centers for Disease Control and Prevention, National Center for Injury Prevention and Control.
Lau et al., (2003), "Differential expression of N-methyl-d-aspartate receptor subunit messenger ribonucleic acids and immunoreactivity in the rat neostriatum during postnatal development.", Neurochemistry International, 43(1): 47-65.
Lindahl et al., (2004), "Glutamate receptor subunits are altered in forebrain and cerebellum in rats chronically exposed to the NMDA receptor antagonist phencyclidine.", Neuropsychopharmacology : official publication of the American College of Neuropsychopharmacology, 29(11): 2065-2073.
Lisman, J., (2003), "Long-term potentiation: outstanding questions and attempted synthesis.", Philosophical Transactions of the Royal Society of London. Series B: Biological Sciences, 358(1432): 829-842.
Lisman et al., (2008), "Circuit-based framework for understanding neurotransmitter and risk gene interactions in schizophrenia.", Trends in Neurosciences, 31(5): 234-242.
Llansola et al., (2005), "Modulation of NMDA receptors in the cerebellum. 1. Properties of the NMDA receptor that modulate its function.", The Cerebellum, 4(3): 154-161.
Lopez De Armentia et al., (2003), "Development and Subunit Composition of Synaptic NMDA Receptors in the Amygdala:

(56) References Cited

OTHER PUBLICATIONS

NR2B Synapses in the Adult Central Amygdala.", The Journal of Neuroscience, 23(17): 6876-6883.

Luby et al., (1959), "Study of a new schizophrenomimetic drug—sernyl.", A.M.A. Archives of Neurology & Psychiatry, 81(3): 363-369.

Makino et al., (2005). "Identification of single-nucleotide polymorphisms in the human N-methyl-D-aspartate receptor subunit NR2D gene, GRIN2D, and association study with schizophrenia.", Psychiatric genetics 15(3): 215.

Miyabe et al., (1997), "Comparative analysis of brain protection by N-methyl-D-aspartate receptor antagonists after transient focal ischemia in cats.", Critical care medicine, 25(6): 1037.

Miyamoto, E., (2006), "Molecular Mechanism of Neuronal Plasticity: Induction and Maintenance of Long-Term Potentiation in the Hippocampus.", Journal of Pharmacological Sciences, 100(5): 433-442.

Molina et al., (2005), "Hypofrontality in men with first-episode psychosis.", The British Journal of Psychiatry, 186(3): 203-208.

Monyer et al., (1994), "Developmental and regional expression in the rat brain and functional properties of four NMDA receptors.", Neuron, 12(3): 529-540.

Morita; et al., (2007), "A Genetic Variant of the Serine Racemase Gene is Associated with Schizophrenia.", Biological Psychiatry, 61(10): 1200-1203.

Morris et al., (2005), "PCP: from pharmacology to modelling schizophrenia.", Current Opinion in Pharmacology, 5(1): 101-106.

Mullasseril et al., (2010), "A subunit-selective potentiator of NR2C- and NR2D-containing NMDA receptors.", Nat Commun, 1: 90.

Nacher et al., (2006), "The role of N-methyl-D-asparate receptors in neurogenesis,", Hippocampus, 16(3): 267-270.

Olney et al., (1999), "NMDA receptor hypofunction model of schizophrenia.", Journal of Psychiatric Research, 33(6): 523-533.

Paal et al., (2003), "Directed (R)- or (S)-Selective Dynamic Kinetic Enzymatic Hydrolysis of 1,2,3,4-Tetrahydroisoquinoline-1-carboxylic Esters.", European Journal of Organic Chemistry, 2008(31): 5269-5276.

Paquet et al., (1997), "AMPA and NMDA Glutamate Receptor Subunits in Midbrain Dopaminergic Neurons in the Squirrel Monkey: An Immunohistochemical and in Situ Hybridization Study.", The Journal of Neuroscience, 17(4): 1377-1396.

Piwowarczyk et al., (2008), "Enantiomers of ($2R*,3R*$)-1-methyl-5-oxo-2-phenyltetrahydro-1H-pyrrolidine-3-carboxylic acid as novel chiral resolving agents,", Tetrahedron: Asymmetry, 19(3): 309-317.

Preskorn et al., (2008), "An Innovative Design to Establish Proof of Concept of the Antidepressant Effects of the NR2B Subunit Selective N-Methyl-D-Aspartate Antagonist, CP-101,606, in Patients With Treatment-Refractory Major Depressive Disorder.", Journal of clinical psychopharmacology, 28(6): 631-637.

Qian et al., (2002), "Channel gating of NMDA receptors.", Physiology & Behavior, 77(4-5): 577-582.

Ressler et al., (2004), "Cognitive enhancers as adjuncts to psychotherapy: Use of d-cycloserine in phobic individuals to facilitate extinction of fear.", Archives of General Psychiatry, 61(11): 1136-1144.

Rhodes, P., (2006), "The Properties and Implications of NMDA Spikes in Neocortical Pyramidal Cells.", The Journal of Neuroscience, 26(25): 6704-6715.

Rudhard et al., (2003), "Absence of Whisker-Related Pattern Formation in Mice with NMDA Receptors Lacking Coincidence Detection Properties and Calcium Signaling.", The Journal of Neuroscience, 23(6): 2323-2332.

Rudolf et al., (1996), "Expression of N-methyl-d-aspartate glutamate receptor subunits in the prefrontal cortex of the rat.", Neuroscience, 73(2): 417-427.

Salter et al., (2005), "NMDA receptors are expressed in developing oligodendrocyte processes and mediate injury.", Nature, 438(7071): 1167-1171.

Santangelo et al., (2012), "Novel NMDA receptor modulators: an update.", Expert Opinion on Therapeutic Patents, 22(11): 1337-1352.

Schuster et al., (2007), "Synthesis of 1, 2, 3, 4-tetrahydroisoquinoline-1-carboxylic acid derivatives via Ugi reactions.", Letters in Organic Chemistry, 4(2): 102-108.

Scott et al., (1978), "The acidic amino acid transport system of the baby hamster kidney cell line BHK21-C13.", Biochimica et Biophysica Acta (BBA)—Biomembranes, 508(2): 379-383.

Seeman et al., (2006), "Psychosis pathways converge via D2High dopamine receptors.", Synapse, 60(4): 319-346.

Sheinin et al., (2001), "Subunit specificity and mechanism of action of NMDA partial agonist d-cycloserine.", Neuropharmacology, 41(2): 151-153.

Sheinin et al., (2002), "Specificity of putative partial agonist, 1-aminocyclopropanecarboxylic acid, for rat N-methyl-d-aspartate receptor subunits.", Neuroscience Letters, 317(2): 77-80.

Shim et al., (2007), "Potentiation of the NMDA receptor in the treatment of schizophrenia: focused on the glycine site.", European Archives of Psychiatry and Clinical Neuroscience, 258(1): 16-27.

Standaert et al., (1994), "Organization of N-methyl-D-aspartate glutamate receptor gene expression in the basal ganglia of the rat.", The Journal of Comparative Neurology, 343(1): 1-16.

Stern et al., (1992), "Single-Channel Conductances of NMDA Receptors Expressed from Cloned cDNAs: Comparison with Native Receptors.", Proceedings of the Royal Society of London. Series B: Biological Sciences, 250(1329): 271-277.

Tang et al., (1999), "Genetic enhancement of learning and memory in mice.", Nature, 401(6748): 63-69.

Tang et al., (2001), "Differential effects of enrichment on learning and memory function in NR2B transgenic mice.". Neuropharmacology, 41(6): 779-790.

Thompson et al., (2002), "Immunohistochemical localization of N-methyl-d-aspartate receptor subunits in the adult murine hippocampal formation: evidence for a unique role of the NR2D subunit.", Molecular Brain Research, 102(1-2): 55-61.

Thurman et al., (1999), "Traumatic Brain Injury in the United States: A Public Health Perspective.", The Journal of Head Trauma Rehabilitation, 14(6): 602-615.

Traynelis et al., (1995), "Control of proton sensitivity of the NMDA receptor by RNA splicing and polyamines.", Science, 268(5212): 873-876.

Tsai et al., (2002), "Glutamatergic mechanisms in schizophrenia.", Annual review of pharmacology and toxicology, 42: 165-179.

Tsai et al., (2006), "D-Alanine Added to Antipsychotics for the Treatment of Schizophrenia.", Biological Psychiatry, 59(3): 230-234.

Tuominen et al., (2005), "Glutamatergic drugs for schizophrenia: a systematic review and meta-analysis.", Schizophrenia Research, 72(2-3): 225-234.

Vicini et al., (1998), "Functional and Pharmacological Differences Between RecombinantN-Methyl-d-Aspartate Receptors.", Journal of Neurophysiology, 79(2): 555-566.

Walker et al., (2002), "Facilitation of Conditioned Fear Extinction by Systemic Administration or Intra-Amygdala Infusions of d-Cycloserine as Assessed with Fear-Potentiated Startle in Rats.", The Journal of Neuroscience, 22(6): 2343-2351.

Waters et al., (2005), "Role of NMDA receptors in development of respiratory control.", Respiratory Physiology & Neurobiology, 149(1-3): 123-130.

Whetsell Jr, W. O., (1996), "Current concepts of excitotoxicity.", Journal of Neuropathology & Experimental Neurology, 55(1): 1-13.

Wilhelm et al., (2006), "Augmentation of behavior therapy with D-cycloserine for obsessive-compulsive disorder.", American Journal of Psychiatry; 165(3): 335-341.

Williams et al., (1994), "Sensitivity of the N-methyl-D-aspartate receptor to polyamines is controlled by NR2 subunits.", Molecular Pharmacology, 45(5): 603-809.

Wollmuth et al., (2004), "Structure and gating of the glutamate receptorion channel.", Trends in Neurosciences, 27(6): 321-328.

Wyllie et al., (1998), "Single-channel activations and concentration jumps: comparison of recombinant NR1a/NR2A and NR1a/NR2D NMDA receptors.", The Journal of Physiology, 510(1): 1-18.

(56) References Cited

OTHER PUBLICATIONS

Yamada et al., (2005), "Identification of Multiple Serine Racemase (SRR) mRNA Isoforms and Genetic Analyses of SRR and DAO in Schizophrenia and d-Serine Levels.", Biological Psychiatry, 57(12): 1493-1503.

Zhang et al., (1999), "A Simple Statistical Parameter for Use in Evaluation and Validation of High Throughput Screening Assays.", Journal of Biomolecular Screening, 4(2): 67-73.

\* cited by examiner

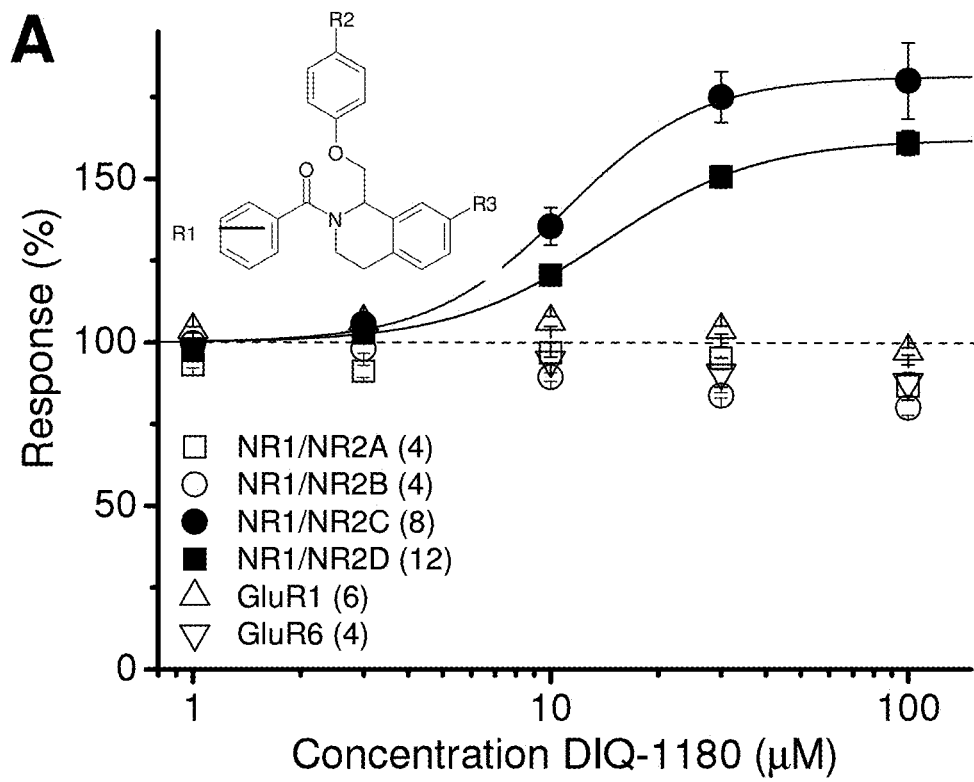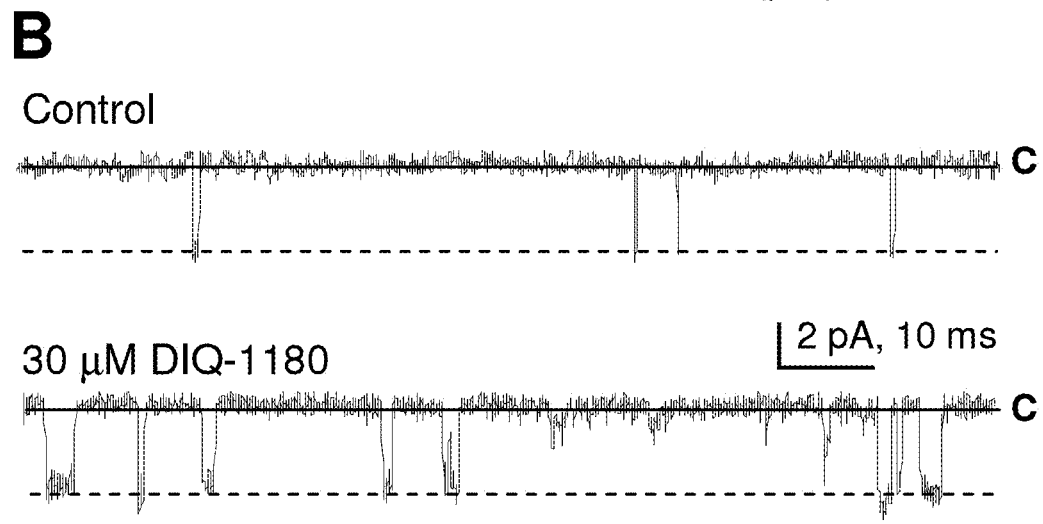
Figs. 2A-B

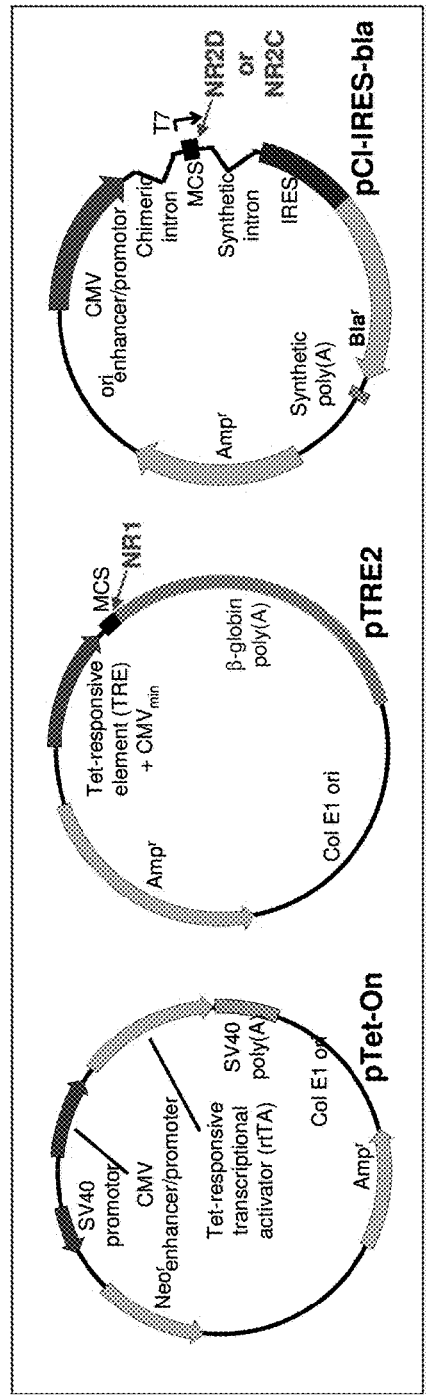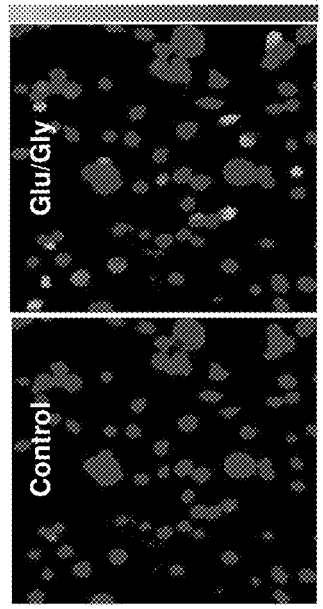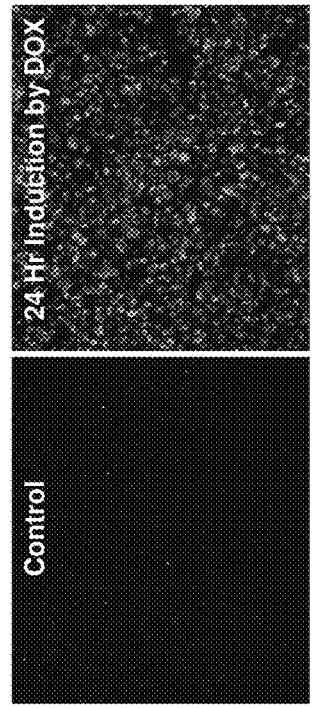
Figs. 4A-C

SUBUNIT SELECTIVE NMDA RECEPTOR POTENTIATORS FOR THE TREATMENT OF NEUROLOGICAL CONDITIONS

CROSS REFERENCE TO RELATED APPLICATIONS

This application is a continuation of U.S. application Ser. No. 13/146,201 filed Sep. 11, 2012, which is a national stage entry of PCT Application Number PCT/US2010/022439 filed Jan. 28, 2010, which claims the benefit of priority to U.S. Provisional Application No. 61/147,897 filed Jan. 28, 2009, all hereby incorporated by reference in their entireties.

STATEMENT REGARDING FEDERALLY FUNDED RESEARCH

This invention was made with government support under Grants NS036654 and NS065371 awarded by the National Institutes of Health. The government has certain rights in the invention.

FIELD OF THE INVENTION

The present invention is in the area of NMDA receptor potentiators that can be used to treat a wide range of neurological diseases and conditions, and includes methods and compositions for the treatment of neurological disorders involving NMDA-receptors.

BACKGROUND OF THE INVENTION

The glutamate receptor gene family encodes ligand-gated ion channels that can be divided into three classes ((AMPA (α-amino-3-hydroxy-5-methyl-4-isoxazolepropionic acid), kainate, and NMDA (N-methyl-D-aspartic acid)) on the basis of agonist pharmacology and molecular structure (Dingledine et al. 1999; Qian & Johnson 2002; Erreger et al 2004; Wollmuth & Sobolevsky 2004). NMDA receptors mediate a slow, $Ca^{2+}$-permeable component of excitatory synaptic transmission in the central nervous system, and have garnered considerable attention because of their prominent role in many normal brain functions, including synaptic plasticity (Lisman 2003; Miyamoto 2006), frequency encoding of information (Froemke et al 2005; Kampa et al 2006; Rhodes 2006), and neuronal development (Rudhard et al 2003; Colonnese et al 2005, 2006; Waters & Machaalani 2005; Nacher & McEwen 2006). In addition, NMDA receptors play an overt role in neuropathology of ischemia and traumatic brain injury (Whetsell 1996; Miyabe et al 1997; Dirnagl et al 1999; Brauner-Osborne et al 2000; Wang & Shuaib 2005). NMDA receptors have been suggested to be involved in a wide range of neurological diseases, including schizophrenia, depression, psychosis, Huntington's disease, Alzheimer's disease, and Parkinson's disease.

NMDA receptors are tetrameric complexes comprised of glycine-binding NR1 subunits, glutamate-binding NR2 subunits, and NR3 (A and B) subunits. The subunit composition determines the functional properties of native NMDA receptors.

Expression of the NR1 subunit alone does not produce a functional receptor. Co-expression of one or more NR2 subunits or one or more NR3 subunits is required to form functional channels. In addition to glutamate, the NMDA receptor requires the binding of a co-agonist, glycine, to allow the receptor to function. A glycine binding site is found on the NR1 and NR3 subunits, whereas the glutamate binding site is found on NR2 subunits. The four NR2 subunits (NR2A, B, C, and D) each endow the receptor with surprisingly divergent single channel conductances, deactivation time courses, and open probabilities (Stern et al 1992; Wyllie et al 1998; Vicini et al 1998; Erreger et al 2004; Erreger et al 2005ab). The increasingly precise anatomical localization of the NR2 subunits (Akazawa et al 1994; Monyer et al 1994; Buller et al 1994; Paquet et al 1997; Dunah et al 1998; Thompson et al 2002; Lau et al 2003; Lopez de Armentia & Sah 2003; Dunah & Standaert 2003; Dunah et al 2003; Hallett & Standaert 2004; Salter & Fern 2005; Karodottir et al 2005) has strengthened the therapeutic rationale for the development of subunit-selective NMDA receptor potentiators, which should target NMDA receptor functions in specific brain regions without engaging NMDA receptors elsewhere. This idea has fueled optimism that NR2 subunit-selective modulators might be well-tolerated therapeutic agents for a wide variety of different indications.

At resting membrane potentials, NMDA receptors are largely inactive due to a voltage-dependent block of the channel pore by magnesium ions. Depolarization releases this channel block and permits passage of calcium as well as other cations. NR2A- and NR2B-containing NMDA receptors are more sensitive to $Mg^{2+}$ blockade than NR2C- and NR2D-containing receptors. The NMDA receptor is modulated by a number of endogenous and exogenous compounds, including, sodium, potassium, and calcium ions that can not only pass through the NMDA receptor channel but also modulate the activity of receptors. Zinc blocks the channel through NR2A- and NR2B-containing receptors in a noncompetitive and voltage-independent manner. Polyamines can also either potentiate or inhibit glutamate-mediated responses (See, for example, McGurk et al., Proc. Nadl. Acad. Sci. USA Vol. 87, pp. 9971-9974, December 1990).

NR2-Subunit Selectivity of Existing NMDA Receptor Modulators

Few NMDA receptor potentiators (or positive modulators) have been described to date in the literature. Perhaps the best known potentiators are naturally occurring polyamines and neurosteroids. Extracellular polyamines such as spermine and spermidine can potentiate with low potency ($EC_{50}$ 100's µM) the function only of NR2B-containing NMDA receptors (Williams et al 1994; Traynelis et al 1995). In addition, various neurosteroids both potentiate and inhibit NR2A/B receptors, depending on concentration and subunit composition. Neurosteroids bind at much higher rates to closed receptors than active receptors (Horak et al 2004, 2006). It is believed that highly subunit-selective drug-like potentiators of heterodimeric NMDA receptors containing NR2A, NR2B, NR2C, or NR2D subunits are heretofore unknown. Experience with non-selective and subunit selective NMDA receptor antagonists suggests that subunit selective potentiators will likely have fewer side effects than non-selective potentiators that act at all NMDA receptors. Moreover, because subunits show differential distribution in the brain, it stands to reason that identifying compounds that target specific subunits may bring about a therapeutically useful effect in one brain region while minimizing effects in brain regions that lack that particular subunit.

Clinical Relevance of NMDA Receptor Potentiators: Learning and Memory

Enhancement of NMDA receptor activity has been proposed to be a useful therapeutic strategy for certain conditions associated with altered cognitive function (Lisman et al., 2008). Overexpression of the NR2B subunit can enhance learning and memory in animal models (Tang et al., 1999, 2001; Cao et al., 2007). In addition, D-cycloserine has been studied as an adjunct to behavioral therapy to promote the extinction of maladaptive associations. This approach is based on the hypothesis that D-cycloserine will augment or enhance therapy-directed learning through potentiation of NMDA receptor-dependent learning. This potentiation is believed to occur through the increased D-serine occupancy of NR1 glycine binding sites. D-cycloserine increased the efficacy of behavioral therapy in clinical trials involving patients suffering acrophobia (Ressler et al., 2004), social anxiety disorder (Hofmann et al., 2006), or obsessive compulsive disorder (Kushner et al., 2007; Wilhelm et al., 2008). The complex multi-subunit composition of NMDA receptors offers further opportunities for pharmacological manipulation for therapeutic gain while minimizing side effects by allowing therapy to be targeted at brain regions expressing specific NR2 subunits.

Clinical Relevance of NMDA Receptor Potentiators for Schizophrenia, Psychoses, Bipolar Disorder, and Depression Schizophrenia and psychosis and other neuropsychiatric disorders arise from changes in neurotransmitter systems, neuronal connectivity, or both. The dopamine hyperactivity hypothesis for schizophrenia, supported by years of clinical experience and neurochemical data, maintains that overactivation of dopamine receptors, such as the D2 subtype, leads to cognitive dysfunction that can be treated by competitive dopaminergic antagonists (Hirsch & Barnes 1995; Seeman et al 2006). The recognition that NMDA inhibitor-induced behavioral effects closely mimic the symptoms of schizophrenia (Javitt and Zukin, 1991; Luby et al., 1959) lead to the hypothesis that NMDA receptor hypofunction may be a causative factor in schizophrenia (Javitt, 2007; Krystal et al., 2002; Olney et al., 1999; Tsai and Coyle, 2002; Yamada et al., 2005; Morita et al., 2007). That is, if blockade of NMDA receptors can reproduce schizophrenic symptoms, it stands to reason that hypofunction of the NMDA receptor system might underlie these symptoms (Coyle et al 2003). This hypothesis led to the proposal that potentiation of NMDA receptor function may have therapeutic benefit in patients suffering from schizophrenia (Heresco-Levy, 2000; Morris et al 2005).

Circuit-based models of schizophrenia have further highlighted the potential role of NMDA receptor hypofunction in interneurons (Lisman et al 2008), which happen to express NR2C and/or NR2D subunits (Monyer et al 1994; Rudolph et al 1996; Thompson et al 2002; Binshtok et al 2006). These models predict that enhancement of interneuron activity (for example by NR2C/D selective potentiators) could be beneficial for patients. Similarly, the ability of certain NR2B-selective antagonists to produce psychosis (Preskorn et al 2008) suggests that potentiation of NMDA receptors containing the NR2B subunit may also be therapeutically beneficial. While not wishing to be bound to a particular theory, such subunit-selective potentiators might bind to a site independent of the agonist recognition site, and enhance the proportion of time the receptor remains open when agonists such as glutamate and glycine bind. Thus, the regional and cell-specific differences in the expression of the NR2C and NR2D subunits in interneurons provides a rationale for the development of NR2C/D-selective potentiators that may improve negative and cognitive symptoms, or influence mood. Additional support for this idea is derived from the observation that enhancement of NMDA receptor function with glycine-site agonists and glycine transport inhibitors may improve negative and cognitive symptoms when used as adjuncts to current antipsychotic therapies (Javitt et al 1994; Depoortere et al 2005). This finding provided rationale for clinical trials of agonists at the glycine site on the NMDA receptor (Coyle and Tsai, 2004; Labrie and Roder, 2009; Shim et al., 2008). Several studies of the use of glycine and D-serine as adjuncts to antipsychotics therapy revealed moderate reduction of negative symptoms and suggested a trend toward a decrease in cognitive symptoms (Tuominen et al., 2005). One subsequent clinical trial suggested a beneficial effect of the glycine site agonist D-alanine on both positive and negative symptoms of schizophrenia (Tsai et al., 2006). D-cycloserine, an antibiotic and glycine site ligand, is a partial agonist at the glycine site and preferentially activates NMDA receptors containing the NR2C subunit (Sheinen et al., 2001; Dravid et al., 2010). Initial clinical studies of D-cycloserine indicated a beneficial effect on negative symptoms (Goff et al., 1999). Because preclinical data suggest the possibility of tachyphylaxis to glycine site ligands, D-cycloserine has been examined with intermittent dosing, which improved negative symptoms in patients suffering schizophrenia (Goff et al., 2008a). Thus, there is general optimism that if allosteric potentiators of NMDA receptor function could be found, such compounds might provide beneficial effects by reducing NMDA receptor hypofunction in psychoses and schizophrenia (Heresco-Levy 2005; Lindsley et al 2006), or perhaps by having antidepressant effects.

Additional circumstantial and correlative data are consistent with a role for NR2C/D subunit in schizophrenia, psychoses, and neuropsychiatric conditions. NR2D subunit mRNA is significantly increased in the prefrontal cortex of schizophrenic patients (Akbarian et al 1996), and NR2D protein expression increases in the frontal cortex of PCP-treated rats (Lindahl & Keifer 2004). Because NMDA receptor hypofunction in frontal and prefrontal cortex correlates with negative symptoms and cognitive impairments (Andreasen et al 1997; Molina et al 2005), an NR2D potentiator might be a useful therapy to treat these symptoms. Interestingly, genetic analysis of polymorphisms suggests that the NR2D gene may be a locus contributing to schizophrenia susceptibility in the Japanese population (Makino et al 2005).

Clinical Relevance of NMDA Receptor Potentiators: Facilitation of Motor Learning During Rehabilitation Of the 1.4 million people who sustain a traumatic brain injury (TBI) each year in the United States, 50,000 die, 235,000 are hospitalized, and 1.1 million are treated and released from an emergency department (Langlois et al., 2006). The Centers for Disease Control and Prevention estimates that at least 5.3 million Americans currently have a long-term or lifelong need for help to perform activities of daily living as a result of a TBI (Thurman et al 1999). On average, every 45 seconds someone in the United States has a stroke, giving rise to 700,000 cases of stroke every year, of which 75% are likely to survive with impaired function requiring rehabilitation (Jorgensen et al., 1995). Millions of stroke and TBI survivors thus suffer from a movement-related problem. Together, stroke and TBI have a greater disability impact than virtually all other neurological conditions and chronic diseases.

The exceptionally large number of patients suffering from disabilities creates a strong need to develop new treatments to facilitate recovery of cortical function following acute neural insults, as occur in ischemic conditions, stroke and traumatic brain injury. Accomplishment of this task has the potential to improve clinical outcomes and quality of life for patients suffering brain injury, stroke, hypoxia, or ischemia. Several recent studies involving NMDA receptors suggest a path towards development of new therapies to enhance cortical motor learning and facilitate recovery from brain insult (See, for example, Nitsche et al., Neuropsychopharmacology (2004) 29, 1573-1578). NMDA receptors require the simultaneous binding of two ligands (glycine, glutamate) before they open to initiate depolarizing current flow into a neuron. A clinically approved partial agonist at the glycine site of the NMDA receptor (D-cycloserine) influences emotional learning, being a potentiator of extinction of conditioned fear in both animal models and human anxiety disorders (Walker et al., 2002; Ressler et al., 2004; Hofmann et al., 2006ab). If motor learning is amenable to pharmacological manipulation in the same manner as emotional learning, this may provide a means to improve rehabilitation of patients suffering neuronal loss as a consequence of stroke or TBI through enhancement of NMDA receptor function during physical therapy.

While the molecular basis for the behavioral effects of D-cycloserine has not been elucidated, several clues exist as to why D-cycloserine might have unique behavioral actions that other partial or full agonists at the either the glycine or glutamate binding site on the NMDA receptor appear to lack. NMDA receptors are comprised of NR1 and NR2 subunits, and D-cycloserine at maximally effective concentrations appears to cause slightly lower responses than maximally effective levels of glycine (the endogenous ligand) at NMDA receptors comprised of NR1/NR2A, NR1/NR2B, and NR1/NR2D subunits. By contrast, a recent study demonstrated that D-cycloserine causes current responses at NR1/NR2C receptors that are nearly twice as large as the endogenous agonist glycine (Sheinin et al., 2002). That is, the agonist D-cycloserine appears to selectively enhance NMDA receptor function when the NR2C subunit is present through its binding to the glycine recognition site on the NR1 subunit. This finding suggests that the unique behavioral effects of D-cycloserine may be related to the potentiation of NR2C-containing NMDA receptors. Implicit in this hypothesis is the idea that enhancement of only NMDA receptors that contain the NR2C subunit may enhance emotional learning.

In cortical structures (hippocampus and neocortex), NR2C subunit mRNA is expressed in subsets of interneurons (Monyer et al., 1994; Binshtock et al., 2006), suggesting that modulation of NR2C function has the potential to sculpt network activity through modulation of interneuronal firing. Thus, NR2C potentiators may be useful as cognitive enhancers, with many potential functions, including treatment and prevention of neurodegenerative diseases associated with cognitive decline. In addition, subunit selective NMDA receptor potentiation may be useful for improving rehabilitation, for example, from stroke and traumatic brain injury.

Clinical Relevance of NMDA Receptor Potentiators: Modulation of Motor Function

NMDA receptors containing the NR2C subunit are highly expressed in cerebellum (Monyer et al 1994; Lansola et al., 2005), a structure well known to be important for sculpting motor function, in particular coordination and fine motor movement. NR2C is particularly abundant at the mossy-fiber-granule cell synapse, and thus modulators of NR2C may have effects on cerebellar function through actions at this synapse, which ultimately gives rise to the input to Purkinje cells via the parallel fibers. In addition, NR2D subunits have been proposed to be expressed by neurons of the deep cerebellar nuclei (Cull-Candy et al., 1998), providing another target for influencing cerebellar function. Thus, NR2C/D-selective NMDA receptor potentiators may control information processing within the cerebellum, and thus have useful effects on motor function, coordination, motor learning, or movement control. Therefore, NR2C/D potentiators can be used to treat a wide range of neurological diseases associated with impaired motor function.

Clinical Relevance of NMDA Receptor Potentiators: Epilepsy

Interneurons typically utilize the inhibitory neurotransmitter GABA and contact a large number of cells. Interneuron firing thus has the ability to hyperpolarize large numbers of neurons. In this way, interneurons can have far-reaching effects on neuronal excitability and signal processing in the central nervous system. Epilepsy is a disorder associated with hypersynchronous and excessive neuronal firing, giving rise to both electrographic and motor seizures. Interneuron inhibition is thought to limit excessive tissue excitability, and a number of compounds that enhance GABA receptor function (e.g. phenobarbital, benzodiazepine) are useful as anticonvulsant agents in some settings. Because NR2C- and NR2D-containing receptors are expressed in hippocampal and cortical inhibitory interneurons but not excitatory principle cells (Monyer et al 1994; Rudolph et al 1996; Thompson et al 2002; Binshtok et al 2006), modulators that selectively enhance NR2C and NR2D receptor function should depolarize interneurons, and thereby increase firing of GABAergic interneurons. As interneurons fire more action potentials, the resulting release of GABA onto excitatory principle cells exerts an inhibitory effect that can be anticonvulsant. Thus, NR2C and NR2D potentiators can be used for their anticonvulsant properties.

Treatment of Bone Disorders

NMDA receptors of the NR2D subtype are found in the osteoblasts, and therefore, compounds which have activity at these receptors can be useful in treating bone disorders.

The bone-remodeling cycle occurs at particular areas on the surfaces of bones. Osteoclasts which are formed from appropriate precursor cells within bones resorb portions of bone; new bone is then generated by osteoblastic activity. Osteoblasts synthesise the collagenous precursors of bone matrix and also regulate its mineralization. The dynamic activity of osteoblasts in the bone remodelling cycle to meet the requirements of skeletal growth and matrix and also regulate its maintenance and mechanical function is thought to be influenced by various factors, such as hormones, growth factors, physical activity and other stimuli. Osteoblasts are thought to have receptors for parathyroid hormone and estrogen. Ostoeclasts adhere to the surface of bone undergoing resorption and are thought to be activated by some form of signal from osteoblasts.

Irregularities in one or more stages of the bone-remodelling cycle (e.g. where the balance between bone formation and resorption is lost) can lead to bone remodelling dirorders, or metabolic bone diseases. Examples of such diseases are osteoporosis, Paget's disease and rickets. Some of these diseases are caused by over-activity of one half of the bone-remodelling cycle compared with the other, i.e. by osteoclasts or osteoblasts. In osteoporosis, for example, there is a relative increase in osteoclastic activity which may cause a reduction in bone density and mass. Osteoporosis is the most common of the metabolic bone diseases and may be either a primary disease or may be secondary to another disease or other diseases.

Post-menopausal osteoporosis is currently the most common form of osteoporosis. Senile osteoporosis afflicts elderly patients of either sex and younger individuals occasionally suffer from osteoporosis.

Osteoporosis is characterized generally by a loss of bone density. Thinning and weakening of the bones leads to increased fracturing from minimal trauma. The most prevalent fracturing in post-menopausal osteoporotics is of the wrist and spine. Senile osteoporosis, is characterized by a higher than average fracturing of the femur.

The tight coupling between the osteoblastic and osteoclastic activities of the bone remodeling cycle make the replacement of bone already lost an extremely difficult challenge. Consequently, research into treatments for prevention or prophylaxis of osteoporosis (as opposed to replacement of already-lost bone) has yielded greater results to date.

Estrogen deficiency has been considered to be a major cause of post-menopausal osteoporosis. Indeed steroids including estrogen have been used as therapeutic agents (New Eng. J. Med., 303, 1195 (1980)). However, recent studies have concluded that other causes must exist (J. Clin. Invest., 77, 1487 (1986)).

Other bone diseases can be caused by an irregularity in the bone-remodeling cycle whereby both increased bone resorption and increased bone formation occur. Paget's disease is one such example.

There remains a need for improved neuroprotective compounds and methods for the treatment of neuropathologies that have reduced toxicity. There is also a need for improved treatments for neuropathic pain, inflammatory pain, stroke, traumatic brain injury, global ischemia, hypoxia, spinal cord trauma, epilepsy, addiction, depression, schizophrenia, motor disorders, and neurodegenerative diseases and disorders.

It would be advantageous to have compounds, compositions including the compounds, and methods of treatment using the compounds to treat these disorders. The present invention provides such compounds, compositions, and methods of treatment.

SUMMARY OF THE INVENTION

NMDA receptor potentiators, including NMDA receptor potentiators of Formulas A-J, and pharmaceutically acceptable salts, esters, prodrugs and derivatives thereof, are provided. Also provided are compositions and methods of using these compounds to treat or prevent a variety of neurological disorders, to provide neuroprotection, to prevent neurodegeneration, to treat neuropathic pain, to control addiction, to ease the symptoms of drug withdrawal, to improve cognition, and to treat schizophrenia, psychoses, depression, and the like. The compounds can be used to treat motor disorders, including tardive diskinesia, to treat bipolar and other neuropsychiatric disorders, including anxiety and depression, and can provide cognitive enhancement. The compounds can be used in patients with normal NMDA receptor expression, so long as the disorder involves the NMDA receptors, and the disorders are not limited to those involving neurodegeneration.

In certain embodiments, the compounds are used for treating schizophrenia, depression, bipolar disorder, obsessive compulsive disorder, neuropathic and inflammatory pain, stroke, traumatic brain injury, epilepsy, other neurologic events or neurodegeneration whose onset or subsequent effects involve NMDA receptor activation, Parkinson's disease, Alzheimer's disease, Huntington's chorea, ALS, and other neurodegenerative conditions known in the art or predicted to be responsive to treatment using NMDA receptor potentiators. In particular embodiments, the compounds are used for the prophylaxis of schizophrenia, depression, neuropathic or inflammatory pain, stroke, traumatic brain injury, epilepsy, other neurologic events or neurodegeneration resulting from NMDA receptor activation, Parkinson's disease, Alzheimer's disease, Huntington's chorea, ALS, and other neurodegenerative conditions. The compounds can be administered on a prophylactic basis to a patient at risk of a disorder associated with NMDA receptor hypofunction. In particular embodiments, the compounds can act as neuroprotective agents by acting on multiple neurons to alter the overall balance of circuit activity.

Osteoblasts have a relatively high concentration of NMDA 2D receptor subtype, but not other receptor subtypes. The compounds described herein which are specific for the NMDA 2D receptor subtype can be used to treat bone disorders, by turning on or turning off bone formation. The compounds described herein can thus enhance bone formation and bone density and have beneficial effects on the activity and differentiation of bone cells.

Accordingly, in one embodiment, the present invention relates to a method for enhancing bone formation in a mammal in need thereof, such as a human, comprising administering to the mammal an effective amount of a compound described herein that is specific for the NMDA 2D receptor subtype. The mammal may have a bone deficit or be at risk of developing a bone deficit, or have a bone remodeling disorder or is at risk of developing such disorder. Examples of bone remodeling disorders include osteoporosis, Paget's disease, osteoarthritis, rheumatoid arthritis, achondroplasia, osteochodrytis, hyperparathyroidism, osteogenesis imperfecta, congenital hypophosphatasia, fribromatous lesions, fibrous displasia, multiple myeloma, abnormal bone turnover, osteolytic bone disease and periodontal disease. In one aspect of this embodiment, the bone remodeling disorder is osteoporosis, including primary osteoporosis, secondary osteoporosis, post-menopausal osteoporosis, male osteoporosis and steroid-induced osteoporosis.

The compounds can also be used to enhance bone formation in a mammal having a bone deficit which does not result from a bone remodeling disorder. Such bone deficits may result, for example, from a bone fracture, bone trauma, or a condition associated with post-traumatic bone surgery, post-prosthetic joint surgery, post-plastic bone surgery, post-dental surgery, bone chemotherapy treatment or bone radiotherapy treatment. The present invention also provides a method for increasing bone density, stimulating osteoblast differentiation, inhibiting osteoclast differentiation, activating the bone formation activity of differentiated osteoblasts, simultaneously stimulating osteoblast differentiation and inhibiting osteoclast differentiation.

The compounds can be administered in combination with at least one bone enhancing agent. Examples of suitable bone enhancing agents include a synthetic hormone, a natural hormone, oestrogen, calcitonin, tamoxifen, a bisphosphonate, a bisphosphonate analog, vitamin D, a vitamin D analog, a mineral supplement, a statin drug, a selective oestrogen receptor modulator and sodium fluoride.

The compounds can be administered alone, or in combination or alternation with other compounds useful for treating or preventing other neurologic events or neurodegeneration resulting from NMDA receptor activation, Parkinson's disease, Alzheimer's disease, Huntington's chorea, ALS, and other neurodegenerative or neurological conditions known to the art to be responsive to treatment using NMDA receptor potentiators

BRIEF DESCRIPTION OF THE FIGURES

FIG. 2A shows two electrode voltage clamp recordings of recombinant NMDA, AMPA, and kainate receptors activated by maximally effective concentrations of glutamate and glycine (100, 50 µM). Values are mean±SEM (n=14-20). FIG. 2B shows how a specific dihydroisoquinoline compound, herein referred to as DIQ-1180, which is a potentiator of NR2C/D-containing NMDA receptors, increased the opening frequency of recombinant NR1/NR2D single channel currents in outside-out patches activated by a maximally effective concentration of glutamate/glycine. C is the closed level; broken line is the open level.

FIG. 4A is a chart showing the construct design for the NR2D-expressing BHK cell line used in Example 8. FIG. 4B is a series of photographs showing that induction of NR1 was visualized using the monoclonal mAb 54.1. The control is black, as there is no fluorescence. The 24 hour induction by DOX produces spots, which in a color photograph would appear as green dots indicating immunofluorescence. FIG. 4C is a series of photographs showing Fura-2 based imaging of a BHK cell line expressing NR1/NR2D during challenge with 100 µM glutamate plus 30 µM glycine. Ratio images are shown for 340/380 nm excitation (510 nm emission) for Fura-2 before and after challenge with glutamate plus glycine.

DETAILED DESCRIPTION

Figure 1:
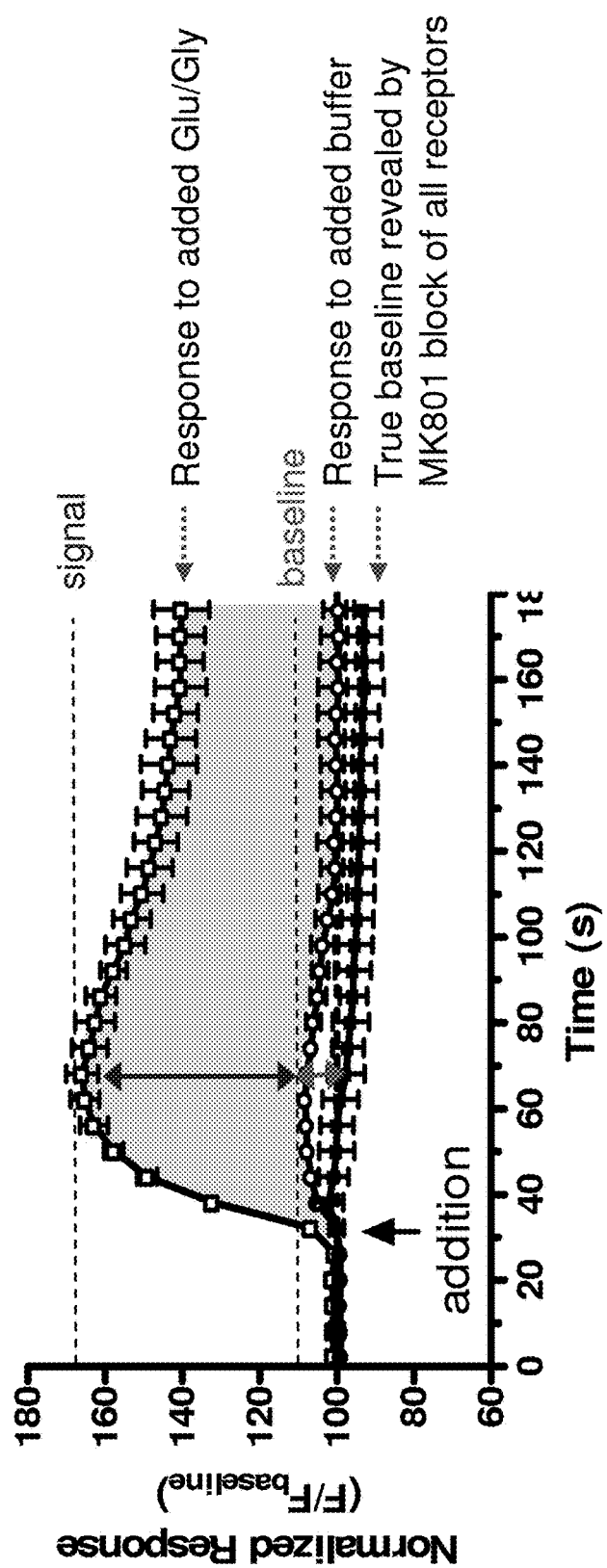
FIG. 1 is a chart showing time course of fluorescence responses of the NR1/NR2D cell line; data points are displayed as $F/F_{BASELINE}$, where F is the fluorescence measured after addition of glutamate/glycine, buffer, or 1 µM MK801 to the well. Data points are mean±SD of 4-5 wells. Final agonist concentrations were 100 µM glutamate/1 mM glycine in the presence of 30 µM of the competitive glycine antagonist 7-Cl-kynurenate.

It has been discovered that certain NMDA receptor potentiators are useful for treating or preventing a wide variety of central nervous system disorders. The potentiators, pharmaceutical compositions including the potentiators, methods for their synthesis, and methods of treatment using the potentiators, are described in detail below.

The present invention will be better understood with reference to the following definitions:

Definitions

Whenever a term in the specification is identified as a range (i.e. $C_{1-4}$ alkyl), the range independently refers to each element of the range. As a non-limiting example, $C_{1-4}$ alkyl means, independently, $C_1$, $C_2$, $C_3$ or $C_4$ alkyl. Similarly, when one or more substituents are referred to as being "independently selected from" a group, this means that each substituent can be any element of that group, and any combination of these groups can be separated from the group. For example, if $R^1$ and $R^2$ can be independently selected from X, Y and Z, this separately includes the groups $R^1$ is X and $R^2$ is X; $R^1$ is X and $R^2$ is Y; $R^1$ is X and $R^2$ is Z; $R^1$ is Y and $R^2$ is X; $R^1$ is Y and $R^2$ is Y; $R^1$ is Y and $R^2$ is Z; $R^1$ is Z and $R^2$ is X; $R^1$ is Z and $R^2$ is Y; and $R^1$ is Z and $R^2$ is Z.

The term "NMDA receptor" as used herein means a postsynaptic receptor which is stimulated, at a minimum, by the excitatory amino acids glutamate and glycine. It is a ligand-gated receptor with a strychnine-insensitive glycine site.

The term "potentiator" as used herein means any compound that increases the flow of current through the NMDA receptor when the agonists required for activity are bound to the receptor. That is, a potentiator enhances the response of NMDA receptors by binding to a site other than the agonist binding site.

The term "co-agonist" as used herein means any pair of compounds (for example glutamate and glycine) that bind to the same receptor complex at different sites and for which binding by both molecules is required to activate the receptor.

The term "antagonist" as used herein means any compound which reduces the flow of current through the NMDA receptor either by blocking the binding of an agonist or co-agonist, blocking the channel, causing channel closure, or binding to a site separate from the agonist binding sites and channel pore that, when occupied, inhibits receptor function.

The term "ligand" as used herein means any compound which binds to a site on the NMDA receptor.

The term "halogen" or "halo" as used herein refers to fluorine, chlorine, bromine, and iodine atoms.

The term "hydroxyl" as used herein means C—OH.

The term "lower alkoxy" as used herein means lower alkyl-O—.

The term "oxo" as used herein means a C=O group.

The term "mercapto" as used herein means a C—SH group.

The term "aryl" as used herein means an organic radical derived from an aromatic hydrocarbon, e.g., phenyl from benzene.

The term "amino" as used herein means —$NH_2$.

The term "alkyl" is used herein, unless otherwise specified, refers to a substituted or unsubstituted, saturated, straight, branched, or cyclic (also identified as cycloalkyl), primary, secondary, or tertiary hydrocarbon, including but not limited to those of C1 to C6. Illustrative examples of alkyl groups are methyl, ethyl, propyl, isopropyl, cyclopropyl, butyl, sec-butyl, isobutyl, tert-butyl, cyclobutyl, 1-methylbutyl, 1,1-dimethylpropyl, pentyl, cyclopentyl, isopentyl, neopentyl, cyclopentyl, hexyl, isohexyl, and cyclohexyl. Unless otherwise specified, the alkyl group can be unsubstituted or substituted with one or more moieties selected from the group consisting of alkyl, halo, haloalkyl, hydroxyl, carboxyl, acyl, acyloxy, amino, amido, carboxyl derivatives, alkylamino, dialkylamino, arylamino, alkoxy, aryloxy, nitro, cyano, thio, sulfonyl, ester, carboxylic acid, amide, phosphonyl, phosphinyl, thioether, oxime, or any other viable functional group that does not inhibit the pharmacological activity of this compound, either unprotected, or protected as necessary, as known to those skilled in the art, for example, as taught in Greene, et al., Protective Groups in Organic Synthesis, John Wiley and Sons, Third Edition, 2002. In certain embodiments, alkyl may be optionally substituted by one or more fluoro, chloro, bromo, iodo, hydroxy, heterocyclic, heteroaryl, carboxy, alkoxy, nitro, $NH_2$, N(alkyl)$_2$, NH(alkyl), alkoxycarbonyl, —N(H or alkyl)C(O)(H or alkyl), —N(H or alkyl)C(O)N(H or alkyl)$_2$, —N(H or alkyl)C(O)O(H or alkyl), —OC(O)N(H or alkyl)$_2$, —S(O)$_n$—(H or alkyl), —C(O)—N(H or alkyl)$_2$, cyano, alkenyl, cycloalkyl, acyl, hydroxyalkyl, heterocyclic, heteroaryl, aryl, aminoalkyl, oxo, carboxyalkyl, —C(O)—$NH_2$, —C(O)—N(H)O(H or alkyl), —S(O)$_2$—NH$_2$, —S(O)$_n$—N(H or alkyl)$_2$ and/or —S(O)$_2$—N(H or alkyl)$_2$, where n in this instance is 1 or 2.

The term "lower alkyl" as used herein means an alkyl radical having 1-9 carbon atoms, which may be straight or branched, including, for example, methyl, ethyl, propyl, isopropyl, butyl, isobutyl, tert-butyl, amyl, isoamyl, hexyl, heptyl, octyl, nonyl, or the like.

The term "cycloalkyl" is used herein, unless otherwise specified, refers to a substituted or unsubstituted, saturated cyclic hydrocarbon, including but not limited to those of $C_3$ to $C_{12}$. Illustrative examples of cycloalkyl groups are cyclopropyl, cyclobutyl, cyclopentyl, and cyclohexyl. Unless otherwise specified, the cycloalkyl group can be unsubstituted or substituted with one or more moieties selected from the group consisting of alkyl, halo, haloalkyl, hydroxyl, carboxyl, acyl, acyloxy, amino, amido, carboxyl derivatives, alkylamino, dialkylamino, arylamino, alkoxy, aryloxy, nitro, cyano, thio, sulfonyl, ester, carboxylic acid, amide, phosphonyl, phosphinyl, thioether, oxime, or any other viable functional group that does not inhibit the pharmacological activity of this compound, either unprotected, or protected as necessary, as known to those skilled in the art, for example, as taught in Greene, et al., Protective Groups in Organic Synthesis, John Wiley and Sons, Third Edition, 2002. In certain embodiments, the cycloalkyl may be optionally substituted by one or more fluoro, chloro, bromo, iodo, hydroxy, heterocyclic, heteroaryl, carboxy, alkoxy, nitro, NH$_2$, N(alkyl)$_2$, NH(alkyl), alkoxycarbonyl, —N(H or alkyl)C(O)(H or alkyl), —N(H or alkyl)C(O)N(H or alkyl)$_2$, —N(H or alkyl)C(O)O(H or alkyl), —OC(O)N(H or alkyl)$_2$, —S(O)$_n$—(H or alkyl), —C(O)—N(H or alkyl)$_2$, cyano, alkenyl, cycloalkyl, acyl, hydroxyalkyl, heterocyclic, heteroaryl, aryl, aminoalkyl, oxo, carboxyalkyl, —C(O)—NH$_2$, —C(O)—N(H)O(H or alkyl), —S(O)$_2$—NH$_2$, —S(O)$_n$—N(H or alkyl)$_2$ and/or —S(O)$_2$—N(H or alkyl)$_2$.

The term "heterocyclic" refers to a non-aromatic or aromatic cyclic group wherein there is at least one heteroatom, such as oxygen, sulfur, nitrogen, or phosphorus in the ring. The term "heteroaryl" or "heteroaromatic," refers to an aromatic that includes at least one sulfur, oxygen, nitrogen or phosphorus in the aromatic ring. Nonlimiting examples of heteroaryl and heterocyclic groups include furyl, furanyl, pyridyl, pyrimidyl, thienyl, isothiazolyl, imidazolyl, tetrazolyl, pyrazinyl, benzofuranyl, benzothiophenyl, quinolyl, isoquinolyl, benzothienyl, isobenzofuryl, pyrazolyl, indolyl, isoindolyl, benzimidazolyl, purinyl, carbazolyl, oxazolyl, thiazolyl, isothiazolyl, 1,2,4-thiadiazolyl, pyrrolyl, quinazolinyl, cinnolinyl, phthalazinyl, xanthinyl, hypoxanthinyl, thiophene, furan, pyrrole, isopyrrole, pyrazole, imidazole, 1,2,3-triazole, 1,2,4-triazole, tetrazole, oxazole, isoxazole, thiazole, isothiazole, pyrimidine or pyridazine, pteridinyl, aziridines, thiazole, isothiazole, oxadiazole, thiazine, pyridine, pyrazine, piperazine, piperidine, pyrrolidine, oxaziranes, phenazine, phenothiazine, morpholinyl, pyrazolyl, pyridazinyl, pyrazinyl, quinoxalinyl, xanthinyl, hypoxanthinyl, pteridinyl, 5-azacytidinyl, 5-azauracilyl, triazolopyridinyl, imidazolopyridinyl, pyrrolopyrimidinyl, pyrazolopyrimidinyl, adenine, N6-alkylpurines, N6-benzylpurine, N6-halopurine, N6-vinypurine, N6-acetylenic purine, N6-acyl purine, N6-hydroxyalkyl purine, N6-thioalkyl purine, thymine, cytosine, 6-azapyrimidine, 2-mercaptopyrimidine, uracil, N5-alkylpyrimidines, N5-benzylpyrimidines, N5-halopyrimidines, N5-vinylpyrimidines, N5-acetylenic pyrimidine, N5-acyl pyrimidine, N5-hydroxyalkyl purine, N6-thioalkyl purine, and isoxazolyl. The heteroaromatic or heterocyclic group can be optionally substituted with one or more substituents selected from halogen, haloalkyl, alkyl, alkoxy, hydroxy, carboxyl derivatives, amido, amino, alkylamino, dialkylamino. The heteroaromatic can be partially or totally hydrogenated as desired. Nonlimiting examples include dihydropyridine and tetrahydrobenzimidazole. In some embodiment, the heteroaryl may be optionally substituted by one or more fluoro, chloro, bromo, iodo, hydroxy, thiol, ether, thioether, heterocyclic, heteroaryl, carboxy, alkoxy, nitro, NH$_2$, N(alkyl)$_2$, NH(alkyl), alkoxycarbonyl, —N(H or alkyl)C(O)(H or alkyl), —N(H or alkyl)C(O)N(H or alkyl)$_2$, —N(H or alkyl)C(O)O(H or alkyl), —OC(O)N(H or alkyl)$_2$, —S(O)$_n$—(H or alkyl), —C(O)—N(H or alkyl)$_2$, cyano, alkenyl, cycloalkyl, acyl, hydroxyalkyl, heterocyclic, heteroaryl, aryl, aminoalkyl, oxo, carboxyalkyl, —C(O)—NH$_2$, —C(O)—N(H)O(H or alkyl), —S(O)$_2$—NH$_2$, —S(O)$_n$—N(H or alkyl)$_2$ and/or —S(O)$_2$—N(H or alkyl)$_2$. Functional oxygen and nitrogen groups on the heteroaryl group can be protected as necessary or desired. Suitable protecting groups are well known to those skilled in the art, and include trimethylsilyl, dimethylhexylsilyl, t-butyldimethylsilyl, and t-butyldiphenylsilyl, trityl or substituted trityl, alkyl groups, acyl groups such as acetyl and propionyl, methanesulfonyl, and p-tolylsulfonyl.

The term "aryl," unless otherwise specified, refers to a carbon based aromatic ring, including phenyl, biphenyl, or naphthyl. The aryl group can be optionally substituted with one or more moieties selected from the group consisting of hydroxyl, acyl, amino, halo, alkylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al. Protective Groups in Organic Synthesis, John Wiley and Sons, Third Edition, 2002. In certain embodiments, the aryl group is optionally substituted by one or more fluoro, chloro, bromo, iodo, hydroxy, heterocyclic, heteroaryl, carboxy, alkoxy, nitro, NH$_2$, N(alkyl)$_2$, NH(alkyl), alkoxycarbonyl, —N(H or alkyl)C(O)(H or alkyl), —N(H or alkyl)C(O)N(H or alkyl)$_2$, —N(H or alkyl)C(O)O(H or alkyl), —OC(O)N(H or alkyl)$_2$, —S(O)$_n$—(H or alkyl), —C(O)—N(H or alkyl)$_2$, cyano, alkenyl, cycloalkyl, acyl, hydroxyalkyl, heterocyclic, heteroaryl, aryl, aminoalkyl, oxo, carboxyalkyl, —C(O)—NH$_2$, —C(O)—N(H)O(H or alkyl), —S(O)$_2$—NH$_2$, —S(O)$_n$—N(H or alkyl)$_2$ and/or —S(O)$_2$—N(H or alkyl)$_2$.

The term "aralkyl," unless otherwise specified, refers to an aryl group as defined above linked to the molecule through an alkyl group as defined above. The term "alkaryl," unless otherwise specified, refers to an alkyl group as defined above linked to the molecule through an aryl group as defined above. Other groups, such as acyloxyalkyl, alkoxyalkyl, alkoxycarbonyl, alkoxycarbonylalkyl, alkylaminoalkyl, alkylthioalkyl, amidoalkyl, aminoalkyl, carboxyalkyl, dialkylaminoalkyl, haloalkyl, heteroaralkyl, heterocyclic-alkyl, hydroxyalkyl, sulfonamidoalkyl, sulfonylalkyl and thioalkyl are named in a similar manner.

The term "alkoxy" or "aryloxy" unless otherwise specified, refers to a moiety of the structure —OR$^1$, where R$^1$ is (although defined elsewhere as including H), an alkyl, aryl, alkaryl or aralkyl group, or substituted alkyl, aryl, aralkyl or alkaryl group, as such groups are defined herein.

The term "acyl," refers to a group of the formula C(O)R' or "alkyl-oxy", wherein R' is an alkyl, aryl, alkaryl or aralkyl group, or substituted alkyl, aryl, aralkyl or alkaryl.

The term "alkenyl" The term "alkenyl" means a monovalent, unbranched or branched hydrocarbon chain having one or more double bonds therein. The double bond of an alkenyl group can be unconjugated or conjugated to another unsaturated group. Suitable alkenyl groups include, but are not limited to $(C_2-C_8)$alkenyl groups, such as vinyl, allyl, butenyl, pentenyl, hexenyl, butadienyl, pentadienyl, hexadienyl, 2-ethylhexenyl,2-propyl-2-butenyl,4-(2-methyl-3-butene)-pentenyl. An alkenyl group can be unsubstituted or substituted with one or two suitable substituents.

The term "carbonyl" refers to a functional group composed of a carbon atom double-bonded to an oxygen atom: —C═O. Similarly, C(O) or C(═O) refers to a carbonyl group.

The term "amino" refers to —NH$_2$, —NH(alkyl) or —N(alkyl)$_2$.

The term "thio" indicates the presence of a sulfur group. The prefix thio- denotes that there is at least one extra sulfur atom added to the chemical. The prefix 'thio-' can also be placed before the name of a compound to mean that an oxygen atom in the compound has been replaced by a sulfur atom. The terms 'thio' and 'thiol' are used interchangeably, unless otherwise indicated.

The term "amido" indicates a group (H or alkyl)-C(O)—NH—.

The term "carboxy" designates the terminal group —C(O)OH.

The term "sulfonyl" indicates an organic radical of the general formula (H or alkyl)-S(═O)$_2$—(H or alkyl'), where there are two double bonds between the sulfur and oxygen.

The term "pharmaceutically acceptable salt" refers to salts or complexes that retain the desired biological activity of the compounds of the present invention and exhibit minimal undesired toxicological effects. Nonlimiting examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalacturonic acid; (b) base addition salts formed with metal cations such as zinc, calcium, bismuth, barium, magnesium, aluminum, copper, cobalt, nickel, cadmium, sodium, potassium, and the like, or with a cation formed from ammonia, N,N-dibenzylethylenediamine, D-glucosamine, tetraethylammonium, or ethylenediamine; or (c) combinations of (a) and (b); e.g., a zinc tannate salt or the like. Also included in this definition are pharmaceutically acceptable quaternary salts known by those skilled in the art, which specifically include the quaternary ammonium salt of the formula —NR$^+$A$^-$, wherein R is H or alkyl and A is a counterion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate).

The term "protected" as used herein and unless otherwise defined refers to a group that is added to an oxygen, nitrogen, or phosphorus atom, or on an acetylenic carbon (i.e., a trimethylsilyl group in place of an acetylenic proton) to prevent its further reaction or for other purposes. A wide variety of oxygen, nitrogen, phosphorus, and acetylenic protecting groups are known to those skilled in the art of organic synthesis, and described in Greene and Wuts, Protective Groups in Organic Synthesis, supra.

It should be understood that the various possible stereoisomers of the groups mentioned above and herein are within the meaning of the individual terms and examples, unless otherwise specified.

As an illustrative example, "1-methyl-butyl" exists in both (R) and the (S) form, thus, both (R)-1-methyl-butyl and (S)-1-methyl-butyl is covered by the term "1-methyl-butyl", unless otherwise specified.

I. Compounds

The compounds typically have one of the following Formulas A-J, as shown below. The compounds typically have EC$_{50}$ values in the range of 0.01 to 10 μM, 0.01 to 9 μM, 0.01 to 8 μM, 0.01 to 7 μM, 0.01 to 6 μM, 0.01 to 5 μM, 0.01 to 4 μM, 0.01 to 3 μM, 0.01 to 2 μM, 0.01 to 1 μM, 0.05 to 7 μM, 0.05 to 6 μM, 0.05 to 5 μM, 0.05 to 4 μM, 0.05 to 3 μM, 0.05 to 2 μM, 0.05 to 1 μM, 0.05 to 0.5 μM, 0.1 to 7 μM, 0.1 to 6 μM, 0.1 to 5 μM, 0.1 to 4 μM, 0.1 to 3 μM, 0.1 to 2 μM, 0.1 to 1 μM, 0.1 to 0.5 μM, 0.1 to 0.4 μM, 0.1 to 0.3 μM, or 0.1 to 0.2 μM.

Formulas A and B are provided below:

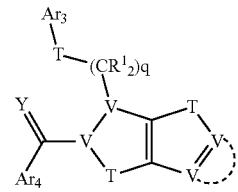

Formula A

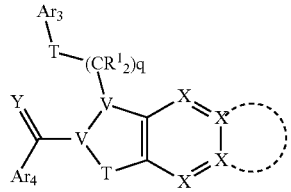

Formula B wherein for Formulas A and B,

Ar$_3$=

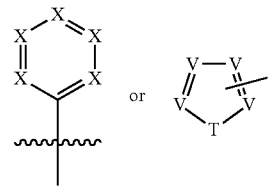

Ar$_4$=

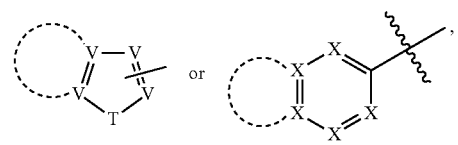

X is, independently, N or C bonded to H or a substituent, J, with the proviso that no more than three of X are N;

Y is independently selected from O, S, NR$^1$, CH$_2$, and CR$^1_2$;

R$^1$ and R$^2$ are, independently, selected from H, alkyl, substituted alkyl, alkenyl, substituted alkenyl, aryl, substituted aryl, heteroaryl, substituted heteroaryl, and hydroxy, and, when $R^1$ is attached to a carbon atom, it can be halo or cyano, T is, independently, $CHR^1$, $CR^1{}_2$, O, S, or $NR^1$, V is, independently, N, or C bonded to H or a substituent J, J is a non-hydrogen substituent selected from the group consisting of halo (—F, —Cl, —Br, —I), nitro, amino ($NR^1R^2$), $OR^1$, $SR^1$, —$R^1$, —$CF_3$, —CN, —$C_2R^1$, —$SO_2CH_3$, —C(=O)$NR^1R^2$—$NR^1{}'C$(=O)$R^1$, —C(=O)$R^1$, —C(=O)$OR^1$, —$(CH_2)_qOR^1$, —OC(=O)$R^1$, —OC(=O)$NR^1R^2$, —$NR^1$(C=Y)—$NR^1R^2$, —$NR^1$(C=Y)—OH, —$NR^1$(C=Y)—SH, sulfonyl, sulfinyl, phosphoryl, and azo, and q is 0-5.

In one embodiment, the aryl ring moiety $Ar_4$ is replaced with a saturated ring.

Representative structures within Formula A and B (also referred to herein as the 1180 class of compounds) include:

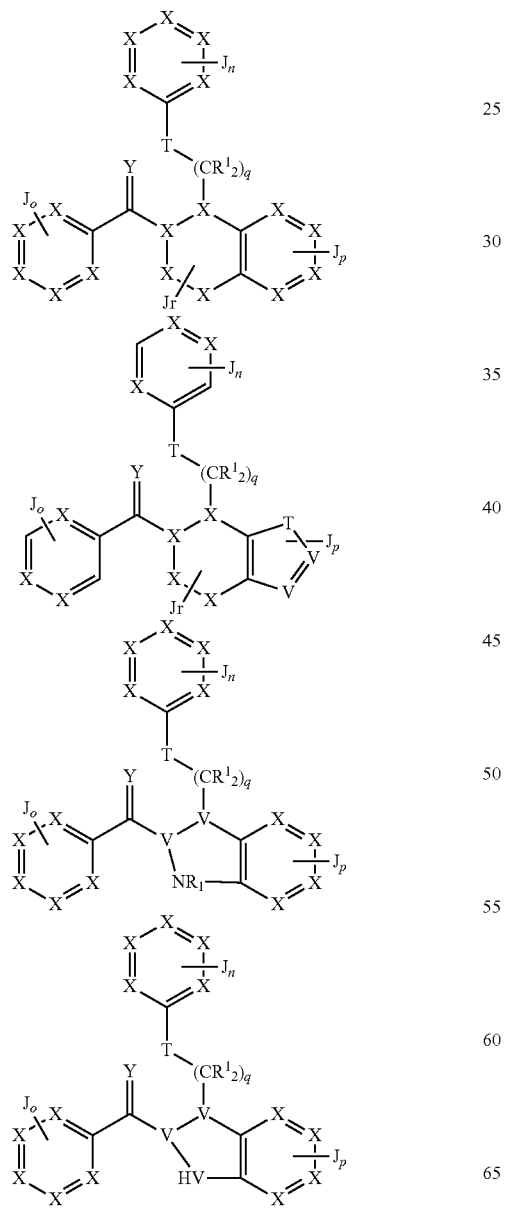

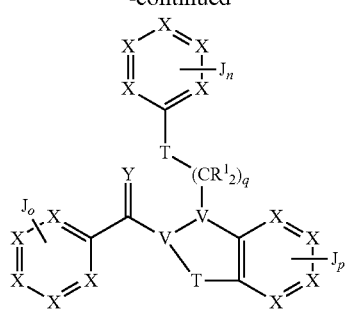

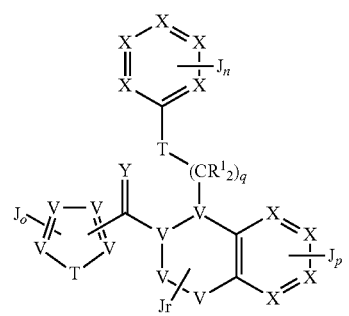

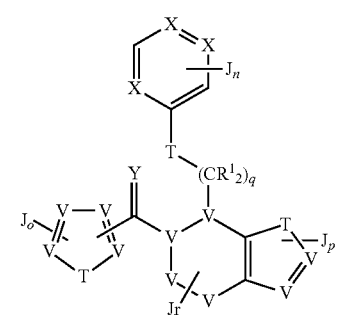

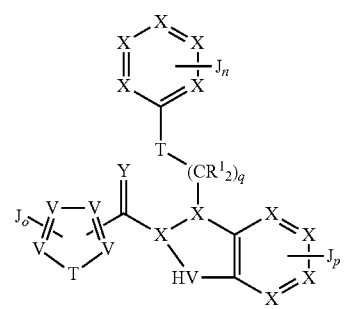

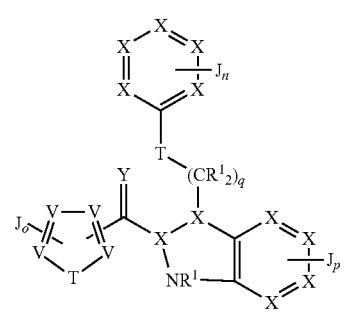

-continued
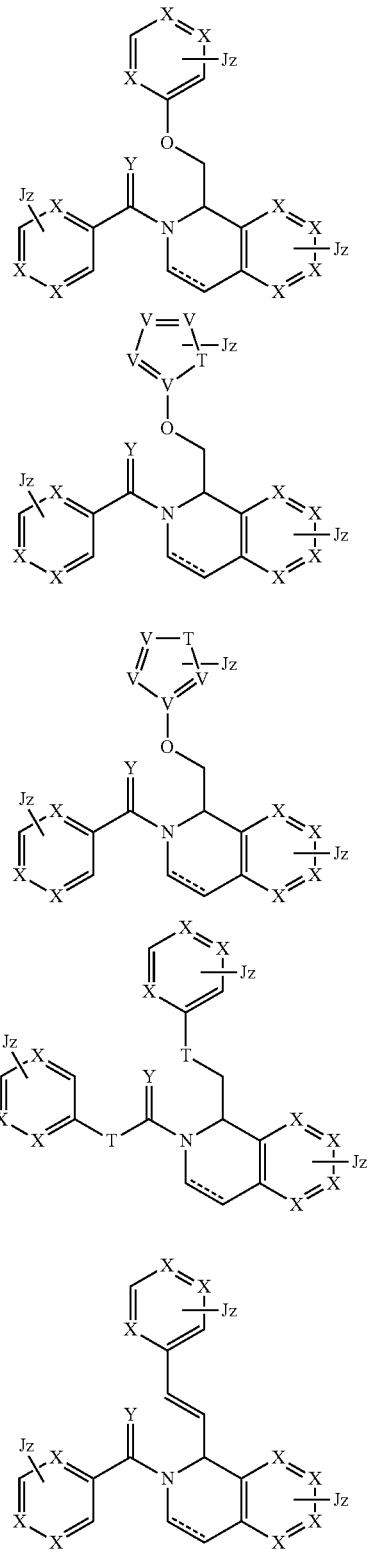
wherein J, T, V, X, and Y are defined above, and n, o, p, and q, are from 0-3.
Other representative structures falling within the scope of Formulas A and B are as follows:

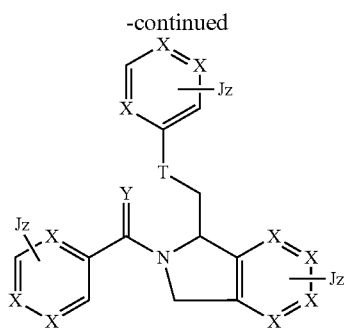

wherein

X is, independently, N or C bonded to H or a substituent, J, with the proviso that no more than three of X are N;

T is, independently, $C(R^1)_2$, $NR^1$, O or S,

V is, independently, N, or C bonded to H or a substituent J,

Y is selected from O, S, $NR^1$, $CH_2$, and $CR^1_2$;

$R^1$ and $R^2$ are independently selected from H, alkyl, substituted alkyl, alkenyl, substituted alkenyl, aryl, substituted aryl, heteroaryl, substituted heteroaryl, and hydroxy, $R^1$ and $R^2$ can optionally join to form a $C_{3-10}$ heterocyclic moiety, which heterocyclic moiety can optionally include a second heteroatom selected from O, S, and N, z is an integer from 0 to 3 and

J is a non-hydrogen substituent selected from the group consisting of halo (—F, —Cl, —Br, —I), nitro, amino ($NR^1R^2$), $OR^1$, $SR^1$, —$R^1$, —$CF_3$, —CN, —$C_2R^1$, —$SO_2CH_3$, —C(=O)$NR^1R^2$—$NR'C(=O)R^1$, —C(=O)$R^1$, —C(=O)$OR^1$, —$(CH_2)_qOR^1$, —OC(=O)$R^1$, —OC(=O)$NR^1R^2$, —$NR^1(C=Y)$—$NR^1R^2$, —$NR^1(C=Y)$—OH, —$NR^1(C=Y)$—SH, sulfonyl, sulfinyl, phosphoryl, and azo.

wherein any double bond can be in the cis or trans (or E or Z) configuration, and wherein the dashed line is an optional double bond.

Representative compounds falling with the scope of Formula A include:

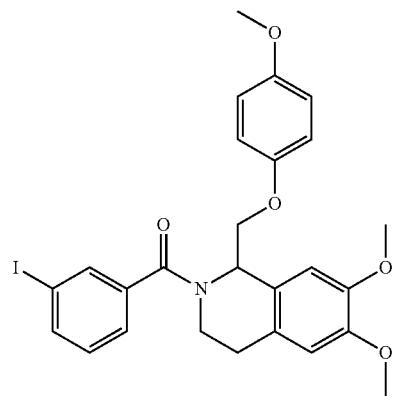

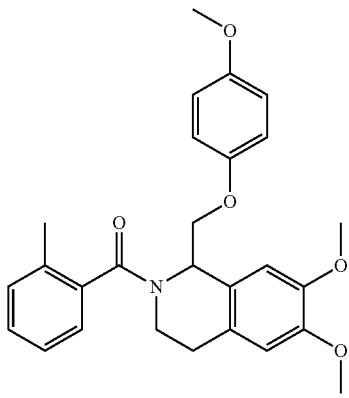

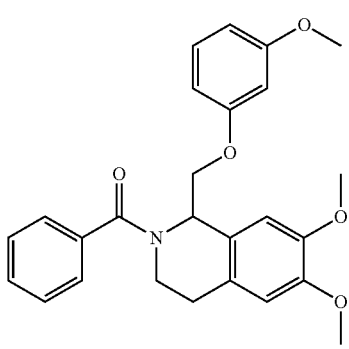

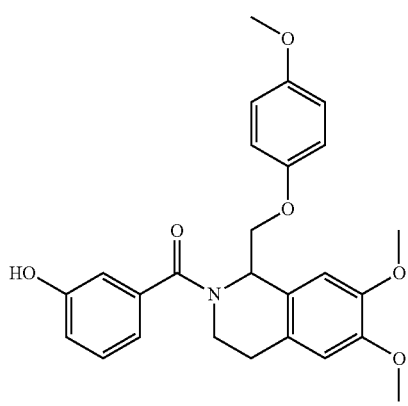

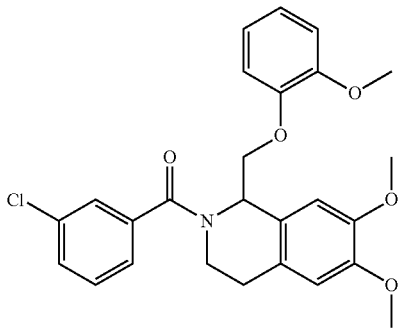

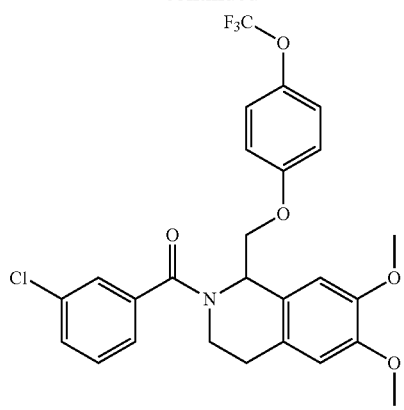
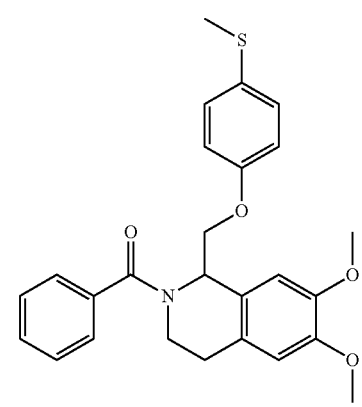
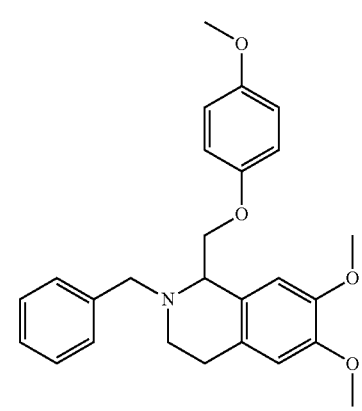
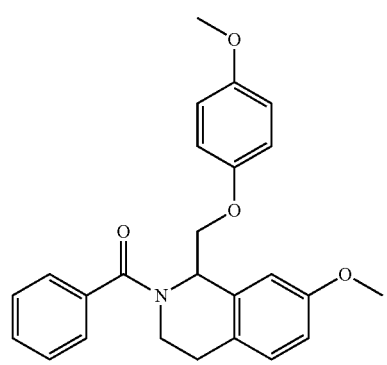
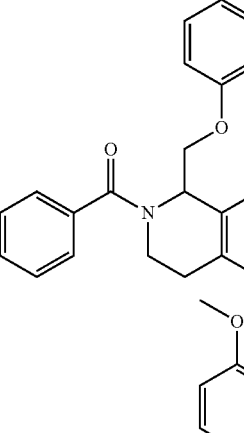
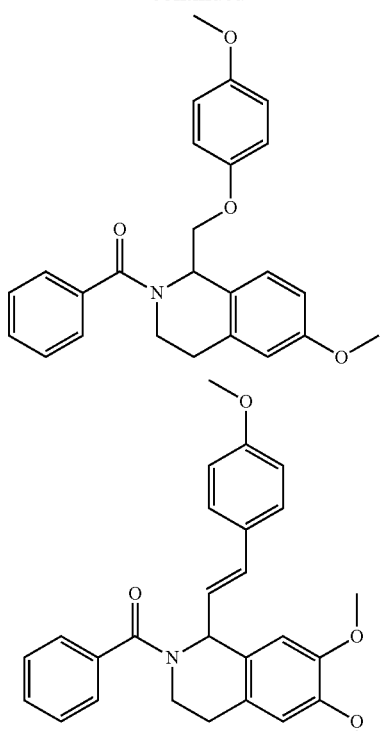
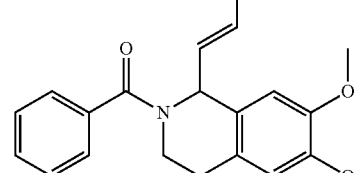
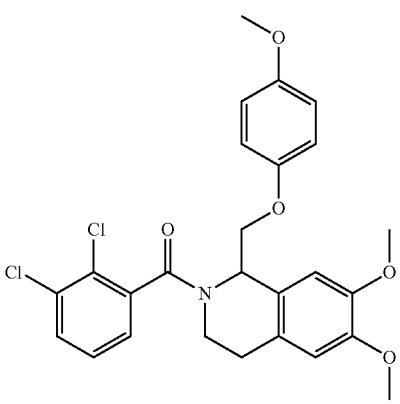
The following specific compounds are also intended to be encompassed:
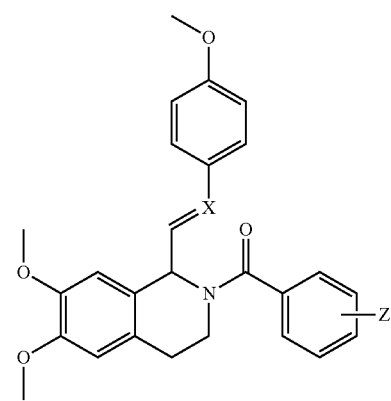

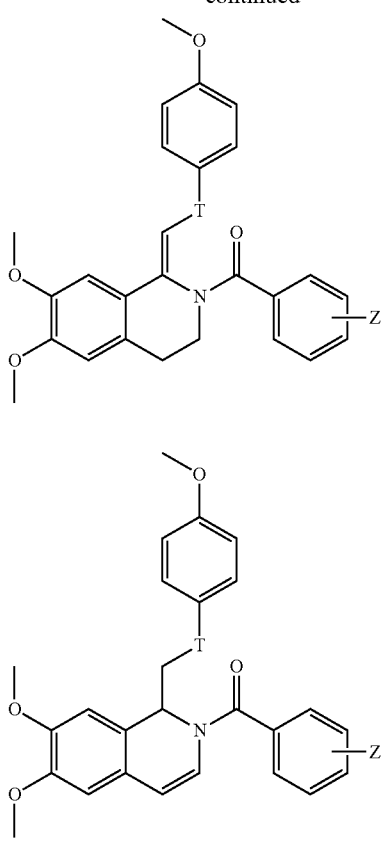
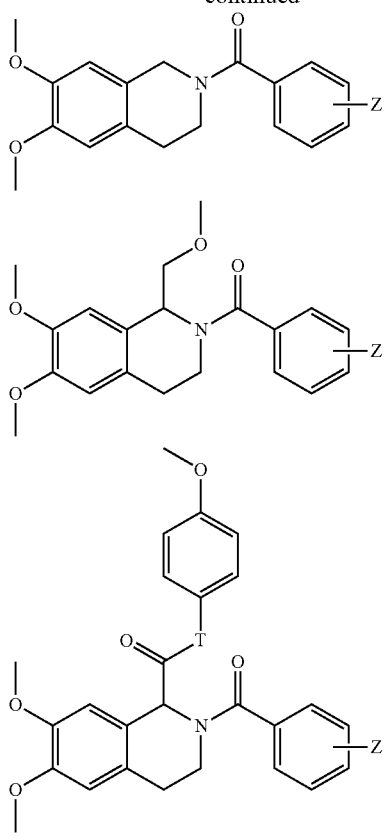
where X, T, and Z are as defined elsewhere, and Ar includes the heteroaryl groups in both Ar$_3$ and Ar$_4$ as defined elsewhere.
Specific compounds within the scope of Formula A also include:
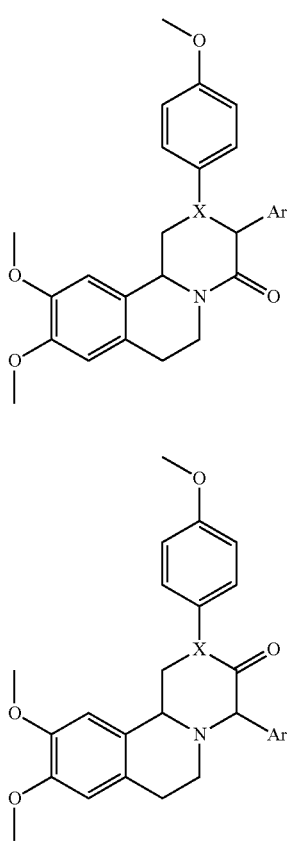
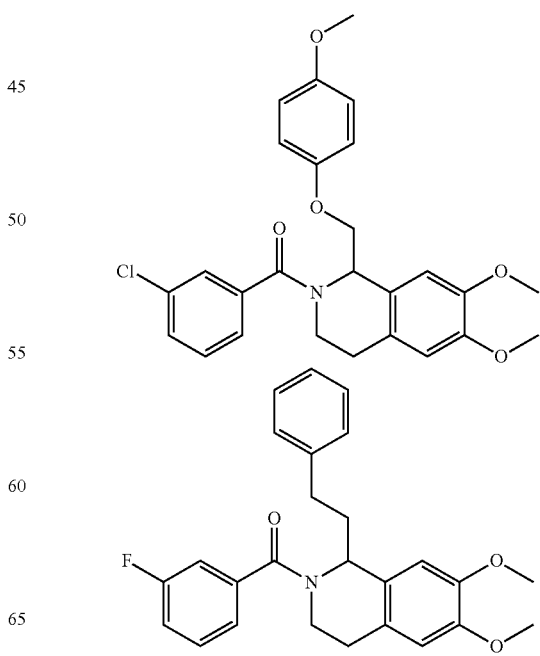

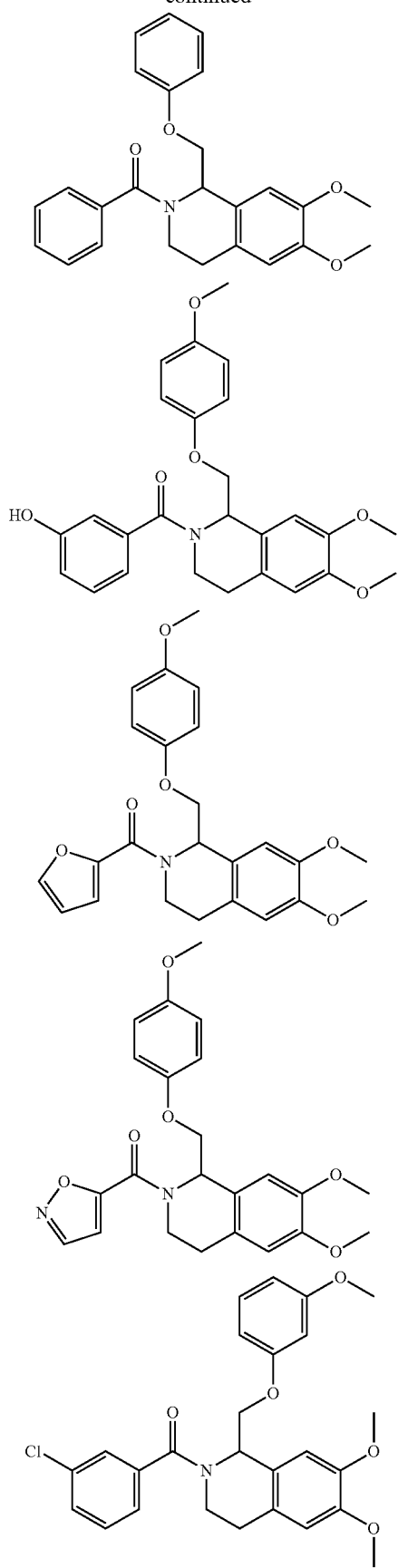
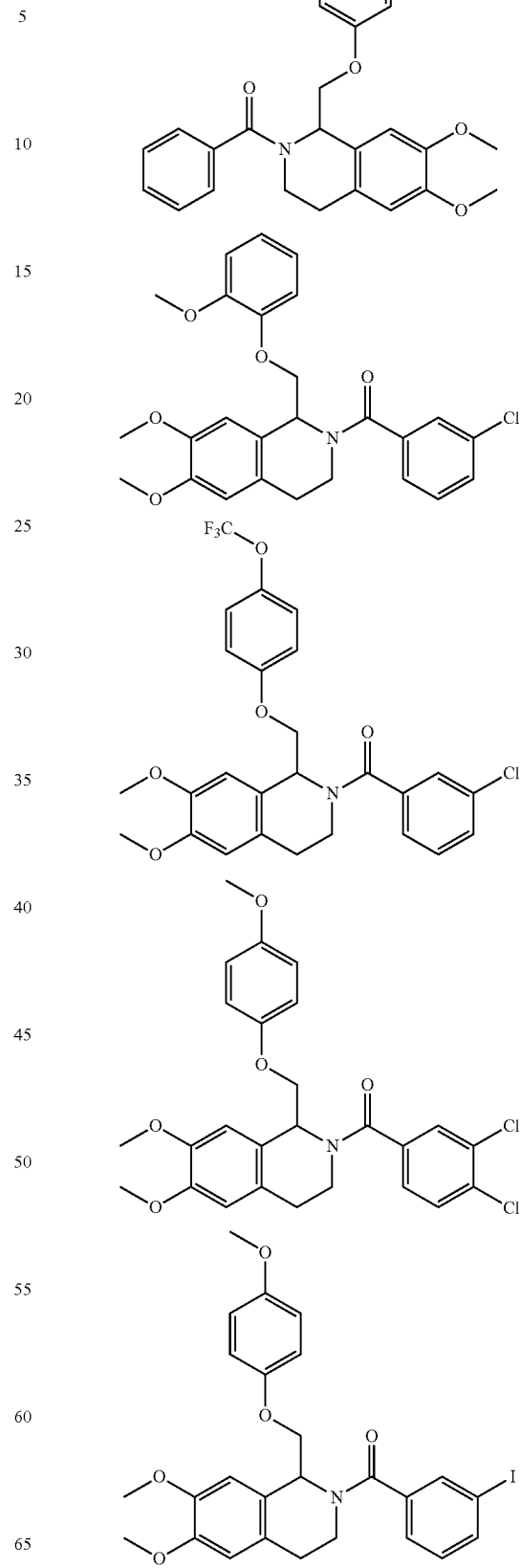

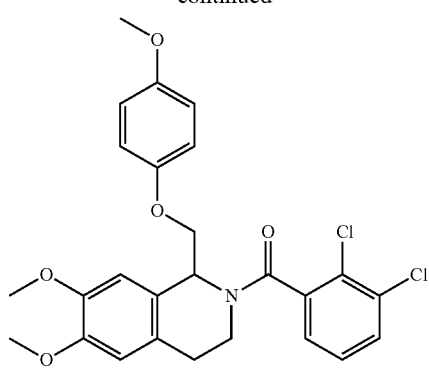
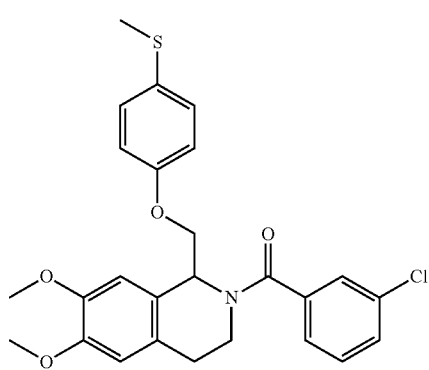
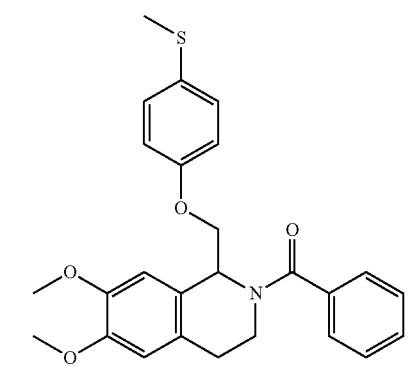
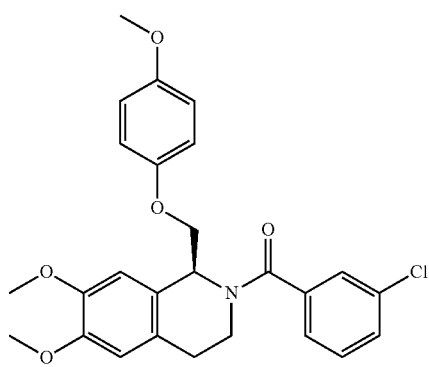
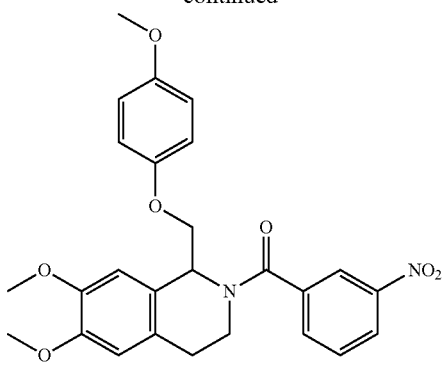
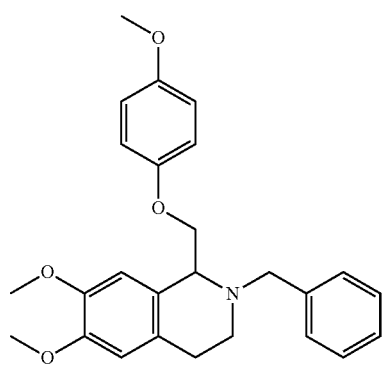
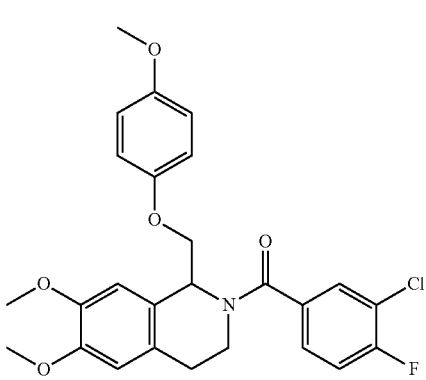
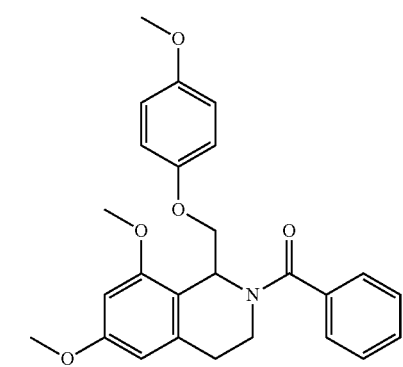

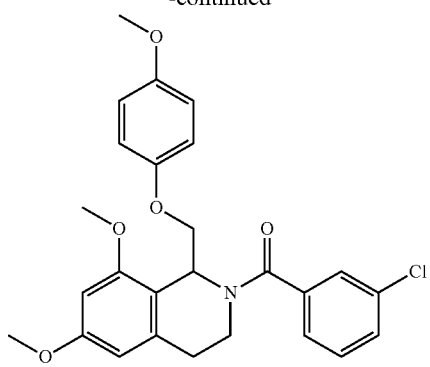
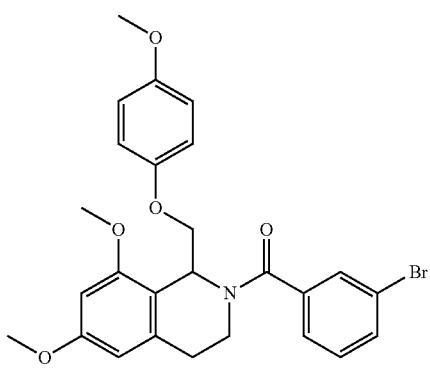
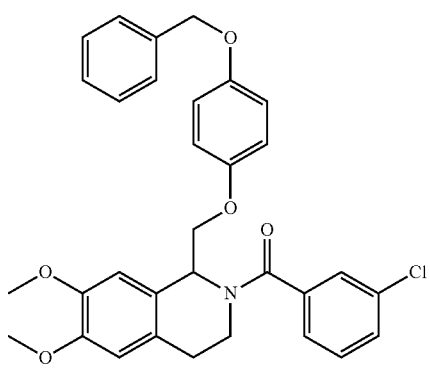
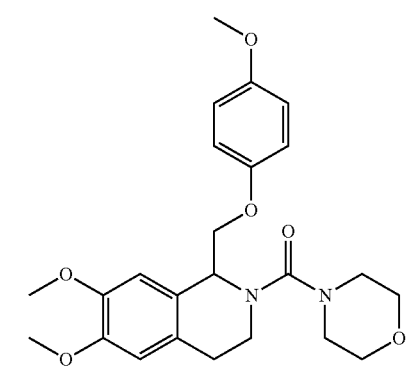
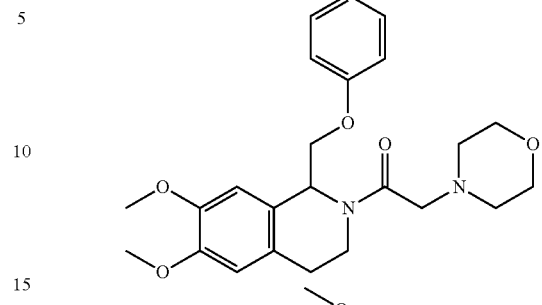
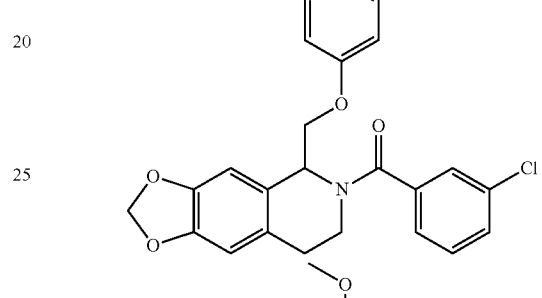
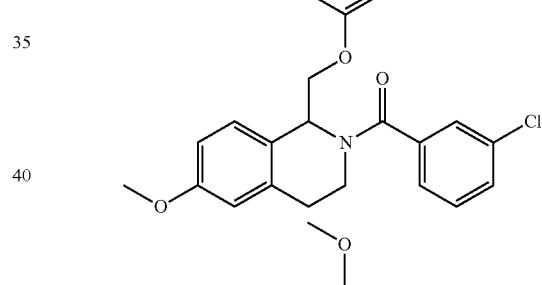
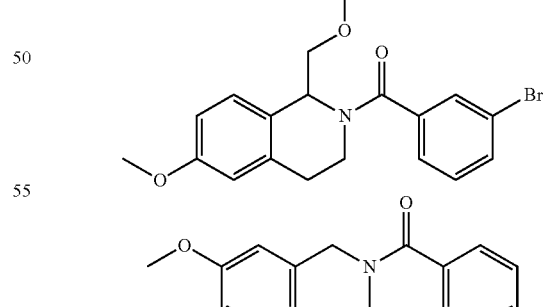
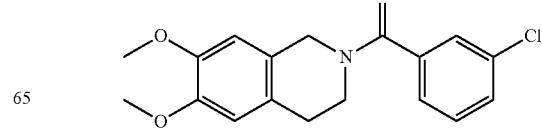

-continued
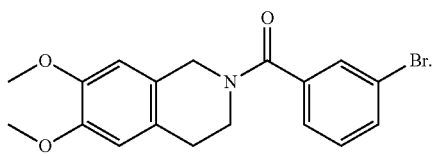 [SMILES: COc1cc2c(cc1OC)CN(C(=O)c1cccc(Br)c1)CC2]
Additional compounds within the scope of Formula A include the following:
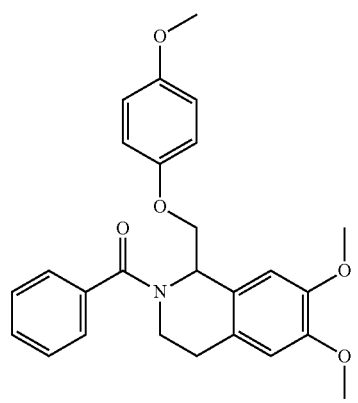 [SMILES: COc1ccc(OCC2c3cc(OC)c(OC)cc3CCN2C(=O)c2ccccc2)cc1]
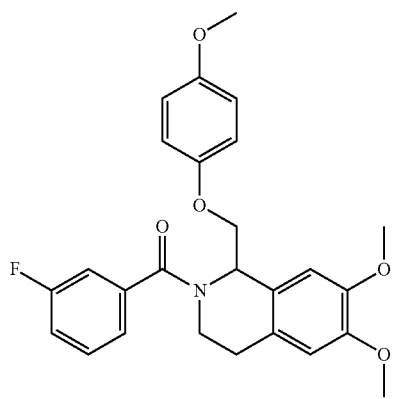 [SMILES: COc1ccc(OCC2c3cc(OC)c(OC)cc3CCN2C(=O)c2cccc(F)c2)cc1]
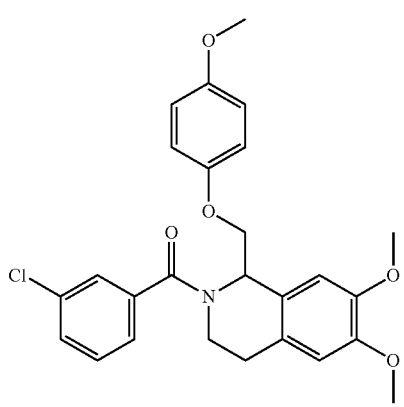
-continued
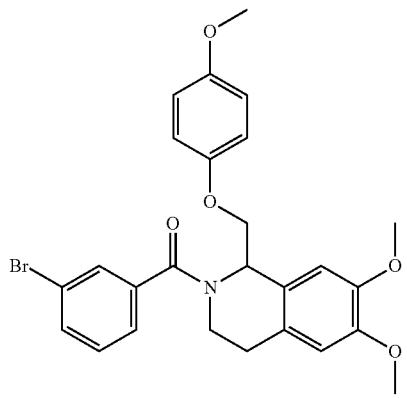 [SMILES: COc1ccc(OCC2c3cc(OC)c(OC)cc3CCN2C(=O)c2cccc(Cl)c2)cc1]
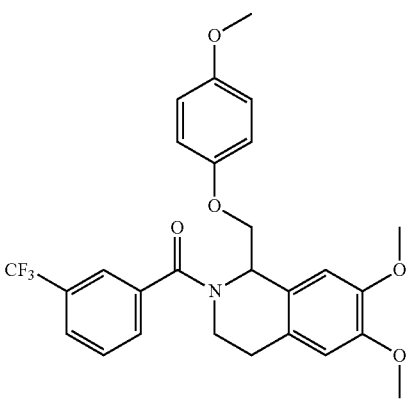 [SMILES: COc1ccc(OCC2c3cc(OC)c(OC)cc3CCN2C(=O)c2cccc(C(F)(F)F)c2)cc1]
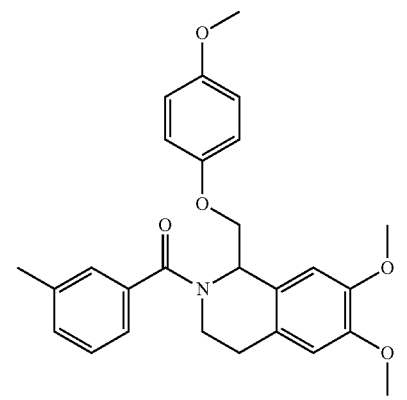
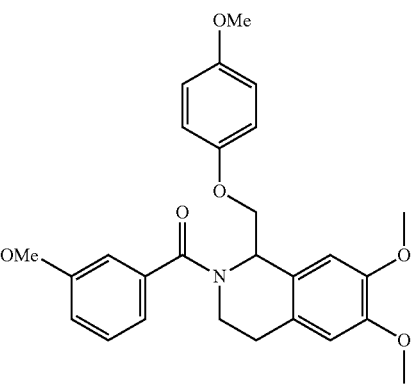 [SMILES: COc1ccc(OCC2c3cc(OC)c(OC)cc3CCN2C(=O)c2cccc(OC)c2)cc1]

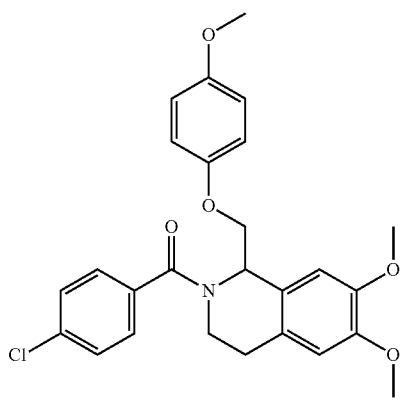 [SMILES: COc1ccc(OCC2c3cc(OC)c(OC)cc3CCN2C(=O)c2ccc(Cl)cc2)cc1]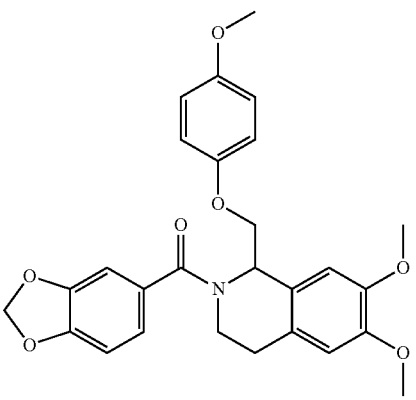 [SMILES: COc1ccc(OCC2c3cc(OC)c(OC)cc3CCN2C(=O)c2ccc3c(c2)OCO3)cc1]

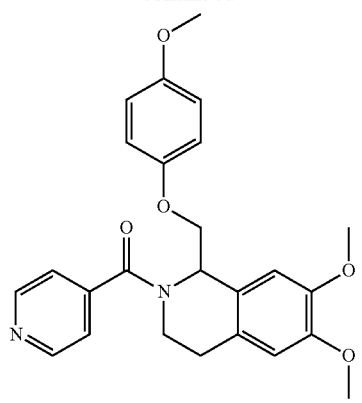 [SMILES: COc1ccc(OCC2c3cc(OC)c(OC)cc3CCN2C(=O)c2ccncc2)cc1]
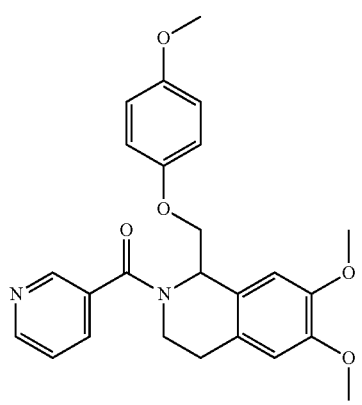 [SMILES: COc1ccc(OCC2c3cc(OC)c(OC)cc3CCN2C(=O)c2cccnc2)cc1]
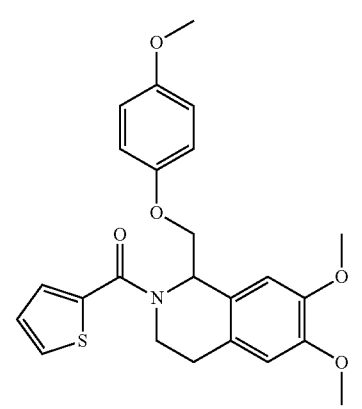 [SMILES: COc1ccc(OCC2c3cc(OC)c(OC)cc3CCN2C(=O)c2cccs2)cc1]
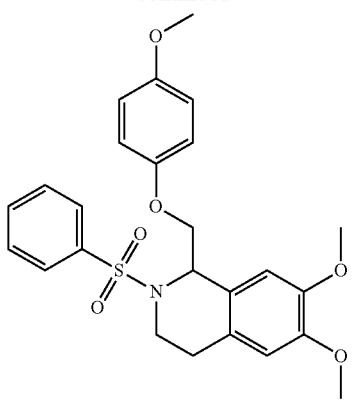 [SMILES: COc1ccc(OCC2c3cc(OC)c(OC)cc3CCN2S(=O)(=O)c2ccccc2)cc1]
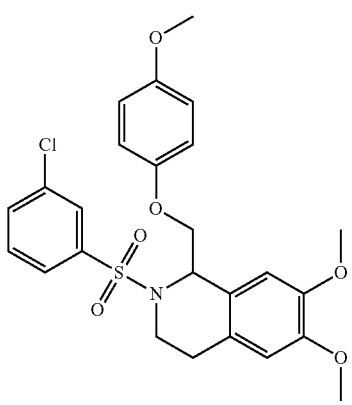 [SMILES: COc1ccc(OCC2c3cc(OC)c(OC)cc3CCN2S(=O)(=O)c2cccc(Cl)c2)cc1]
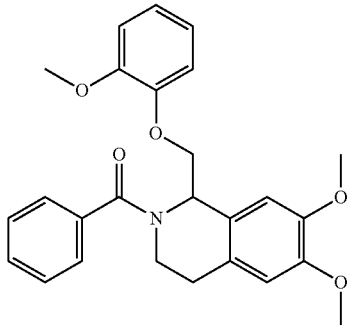

-continued
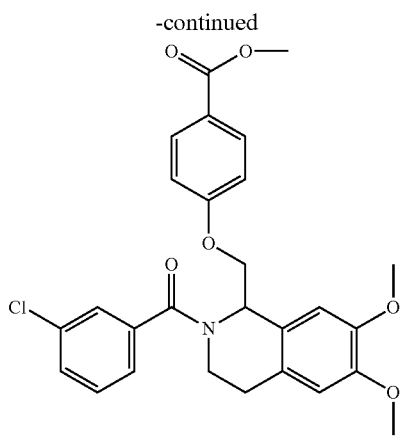
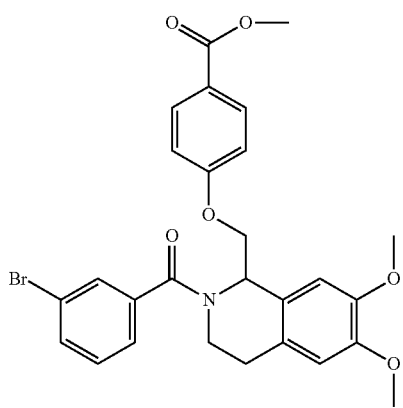 [SMILES: COC(=O)c1ccc(OCC2c3cc(OC)c(OC)cc3CCN2C(=O)c2cccc(Cl)c2)cc1]
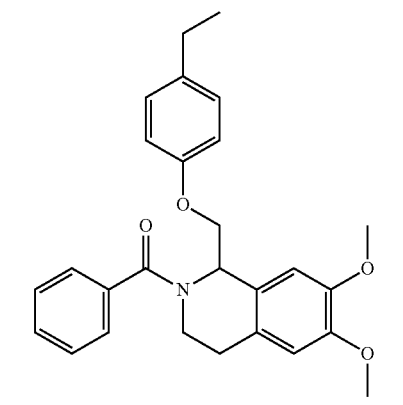
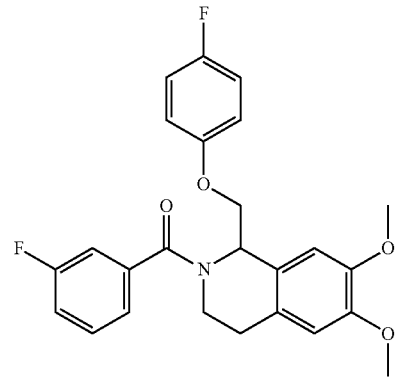 [SMILES: COc1cc2c(cc1OC)C(COc1ccc(F)cc1)N(C(=O)c1cccc(F)c1)CC2]
-continued
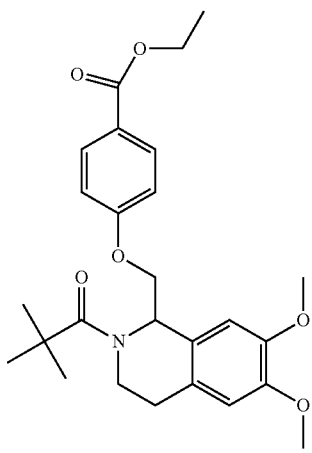
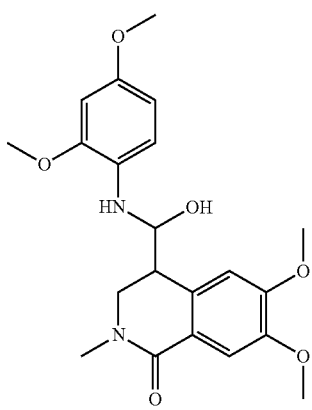
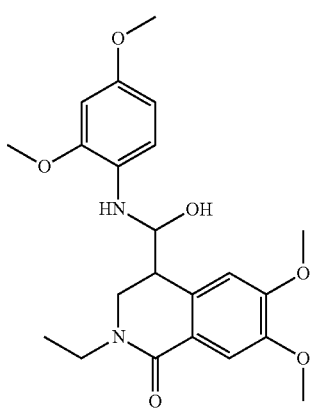
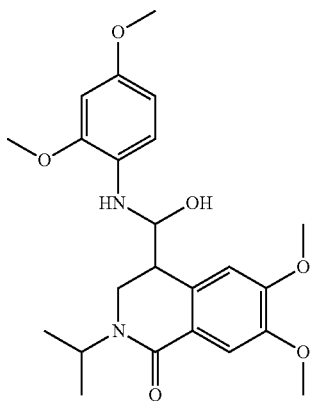

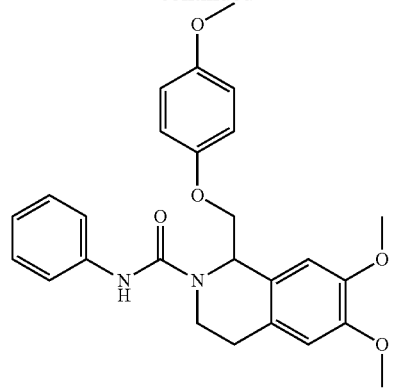 [SMILES: COc1ccc(OCC2c3cc(OC)c(OC)cc3CCN2C(=O)Nc2ccccc2)cc1]
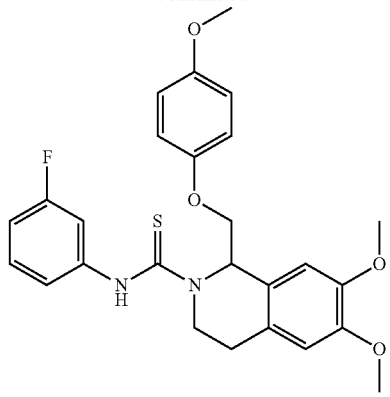
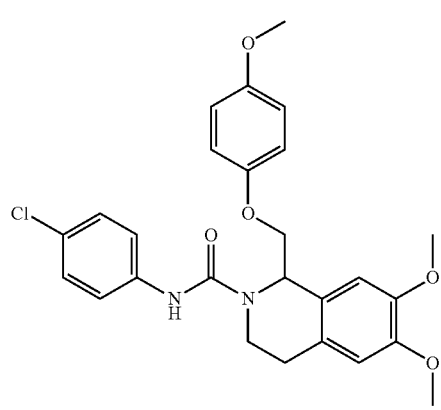 [SMILES: COc1ccc(OCC2c3cc(OC)c(OC)cc3CCN2C(=O)Nc2ccc(Cl)cc2)cc1]
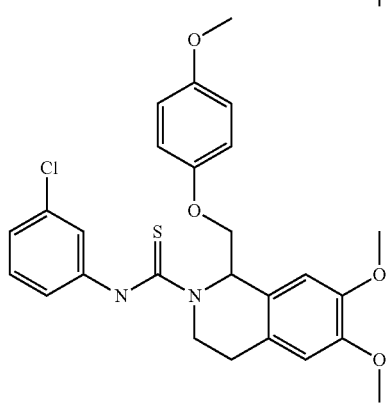
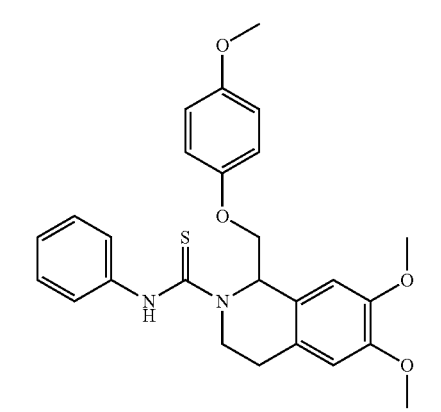 [SMILES: COc1ccc(OCC2c3cc(OC)c(OC)cc3CCN2C(=S)Nc2ccccc2)cc1]
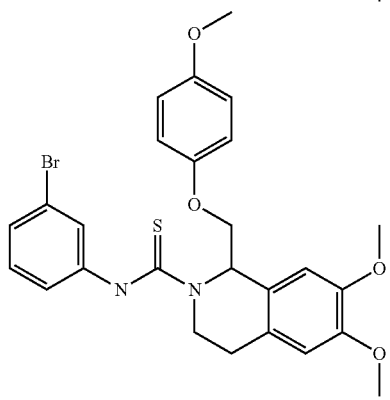
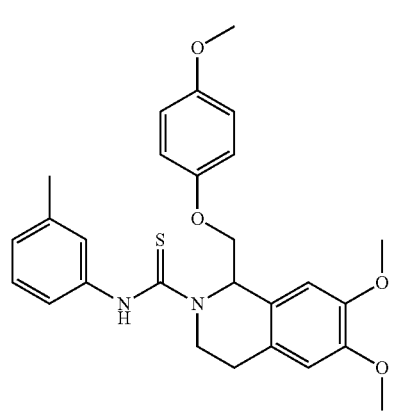
Formulas C-E are shown below:
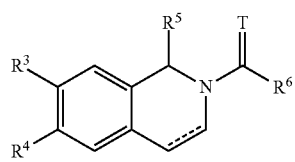
Formula C
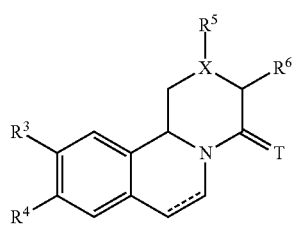
Formula D -continued

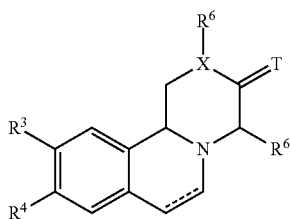

Formula E wherein, for Formulas C-E, $R^3$ and $R^4$ are, individually, H or a substituent J, $R^5$ is selected from H, —$CH_2OCH_3$, —$C(R^1)$=X—$R^6$, or is a double bond attached to the ring, to a hydrogen, and to CH-T-$R^6$, $R^6$ is an aryl or five or six membered ring heteroaryl, optionally substituted with from one to three substituents, J, as defined above, X is $CR^1$ or N, and T is $C(R^1)_2$, $NR^1$, O or S, wherein any double bond can be in the cis or trans (or E or Z) configuration, and wherein the dashed line is an optional double bond.

Formulas F-H are shown below

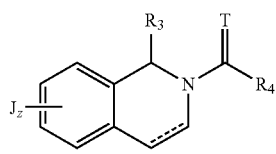

Formula F

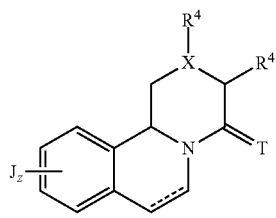

Formula G

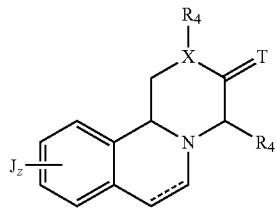

Formula H wherein $R^3$ is selected from —$CH_2OCH_3$, —$C(R^1)$=X—$R^4$, —$CH_2OR^4$—$CH_2$—$R^4$ or is a double bond attached to the ring, to a hydrogen, and to -T-$R^4$, $R^4$ is an aryl or five or six membered ring heteroaryl, optionally substituted with from one to three substituents, J, is a non-hydrogen substituent selected from the group consisting of halo (—F, —Cl, —Br, —I), nitro, amino ($NR^1R^2$), $OR^1$, $SR^1$, —$R^1$, —$CF_3$, —CN, —$C_2R$, —$SO_2CH_3$, —C(=O)$NR^1R^2$—$NR'C$(=O)$R^1$, —C(=O)$R^1$, —C(=O)$OR^1$, —$(CH_2)_qOR^1$, —OC(=O)$R^1$, —OC(=O)$NR^1R^2$, —$NR^1$(C=Y)—$NR^1R^2$, —$NR^1$(C=Y)—OH, —$NR^1$(C=Y)—SH, sulfonyl, sulfinyl, phosphoryl, and azo.

X is $CR^1$ or N (where $R^1$ is defined above), and

T is, independently, $C(R^1)_2$, $NR^1$, O or S, wherein any double bond can be in the cis or trans configuration, and wherein the dashed line is an optional double bond.

Formulas I and J are shown below:

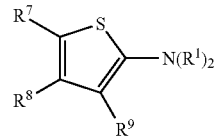

Formula I wherein $R^1$ is as defined above, $R^7$ is selected from the group consisting of H, —$C_{1-6}$ alkyl, —$C_{1-6}$ substituted alkyl, —$C_{6-10}$ aryl, —$C_{6-10}$ substituted aryl, —$C_{6-10}$ heteroaryl, —$C_{6-10}$ substituted heteroaryl, —C(O)-alkyl, —C(O)-substituted alkyl, —C(O)-aryl, —C(O)-substituted aryl, —C(O)-arylalkyl, C(O)-substituted arylalkyl, —C(O)-alkylaryl, —C(O)-substituted alkylaryl-CN, $N_3$, $NO_2$, —OH, —$NH_2$, —SH, —$OR^1$, —$NHR^1$, —$N(R)_2$, —$SR^1$, —OC(O)$R^1$, NHC(O)$R^1$, —SC(O)$R^1$, —OC(O)$OR^1$, —NHC(O)$R^1$, —$CH_2OH$, —$CH_2CN$, —$CH_2N_3$, —$CO_2R^1$, —CON($R^1)_2$, —C(O)-alkyl, —C(O)-substituted alkyl, —C(O)-aryl, —C(O)-substituted aryl, —C(O)-heteroaryl, and —C(O)— substituted heteroaryl, $R^{8-9}$ are, individually, H, OH, —$NH_2$, —SH, —$OR^1$, —$NHR^1$, —$N(R^1)_2$, —$SR^1$, —OC(O)$R^1$, NHC(O)$R^1$, —$C_{1-6}$ alkyl, —$C_{1-6}$ substituted alkyl, —$C_{6-10}$ aryl, —$C_{6-10}$ substituted aryl, —$C_{6-10}$ heteroaryl, —$C_{6-10}$ substituted heteroaryl,

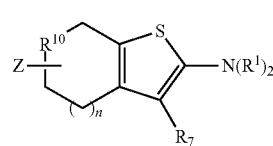

Formula J wherein $R^1$ is as defined above, $R^1$ is as defined above, $R^7$ is selected from the group consisting of H, —$C_{1-6}$ alkyl, —$C_{1-6}$ substituted alkyl, —$C_{6-10}$ aryl, —$C_{6-10}$ substituted aryl, —$C_{6-10}$ heteroaryl, —$C_{6-10}$ substituted heteroaryl, —C(O)-alkyl, —C(O)-substituted alkyl, —C(O)-aryl, —C(O)-substituted aryl, —C(O)-arylalkyl, C(O)-substituted arylalkyl, —C(O)-alkylaryl, —C(O)-substituted alkylaryl-CN, $N_3$, $NO_2$, —OH, —$NH_2$, —SH, —$OR^1$, —$NHR^1$, —$N(R)_2$, —$SR^1$, —OC(O)$R^1$, NHC(O)$R^1$, —SC(O)$R^1$, —OC(O)$OR^1$, —NHC(O)$R^1$, —$CH_2OH$, —$CH_2CN$, —$CH_2N_3$, —$CO_2R^1$, —CON($R)_2$, —C(O)-alkyl, —C(O)-substituted alkyl, —C(O)-aryl, —C(O)-substituted aryl, —C(O)-heteroaryl, and —C(O)— substituted heteroaryl, $R^{10}$ is —$CH_2$—, —S—, —O—, —$NHR^1$—, —$N(R^1)_2$—, —C(O)—, —C(S)—, —$C(NR^1)_2$—, N is 0-4, and Z is a substituent as defined elsewhere herein.

Specific compounds within formulas I and J are provided below:
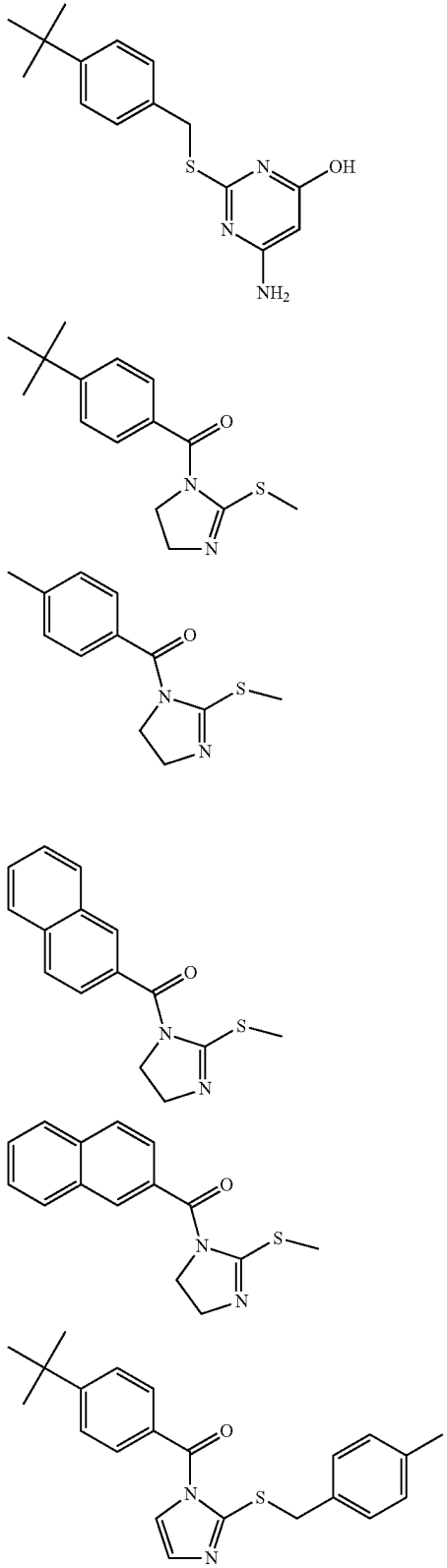
Further specific compounds include:
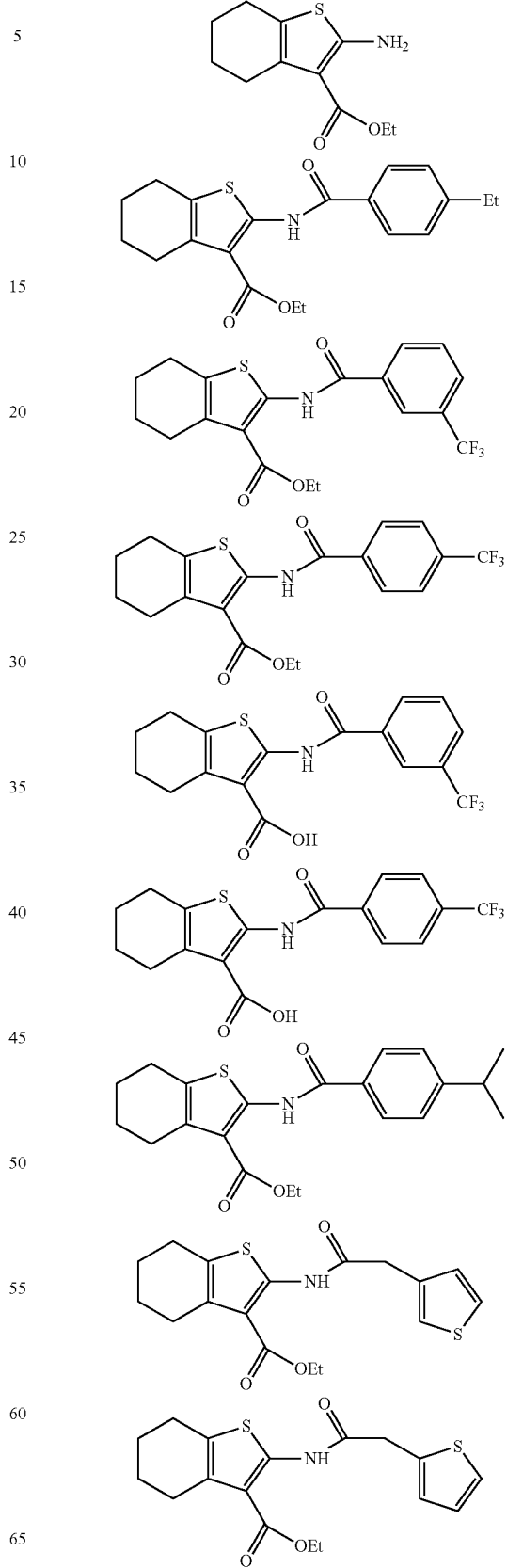

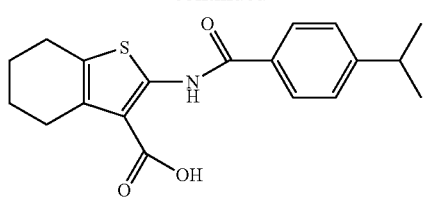
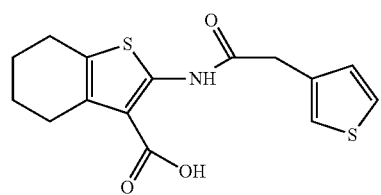
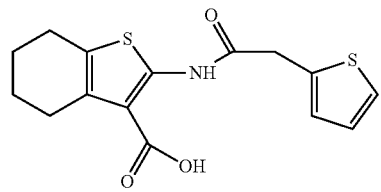
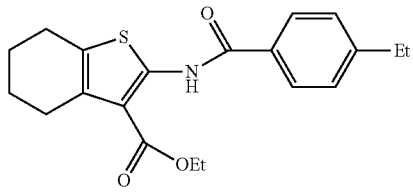
Still further additional compounds include the following:
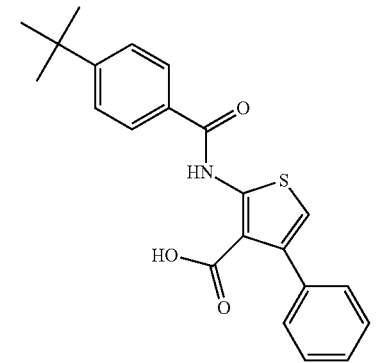
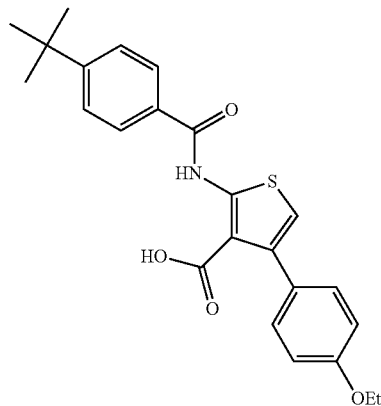
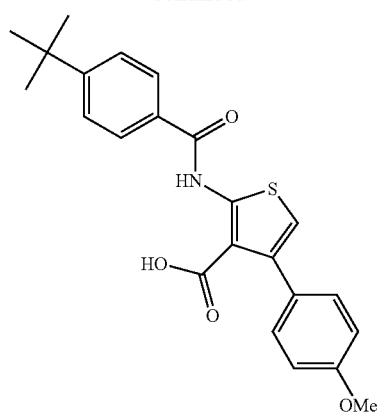
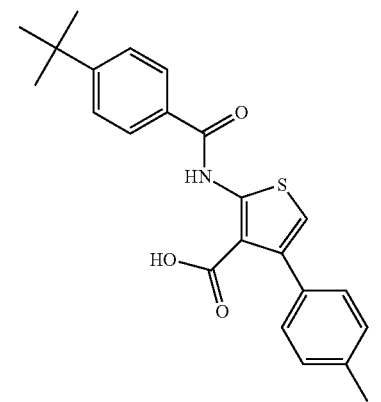
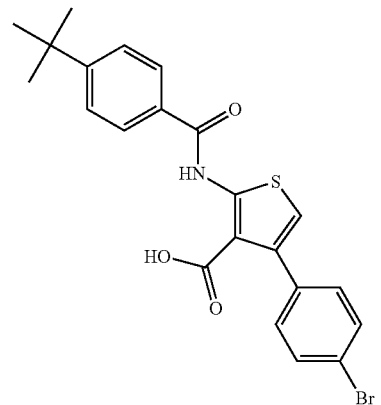
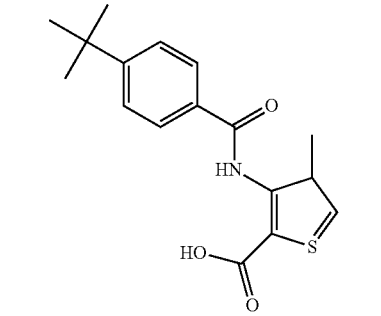

47
-continued
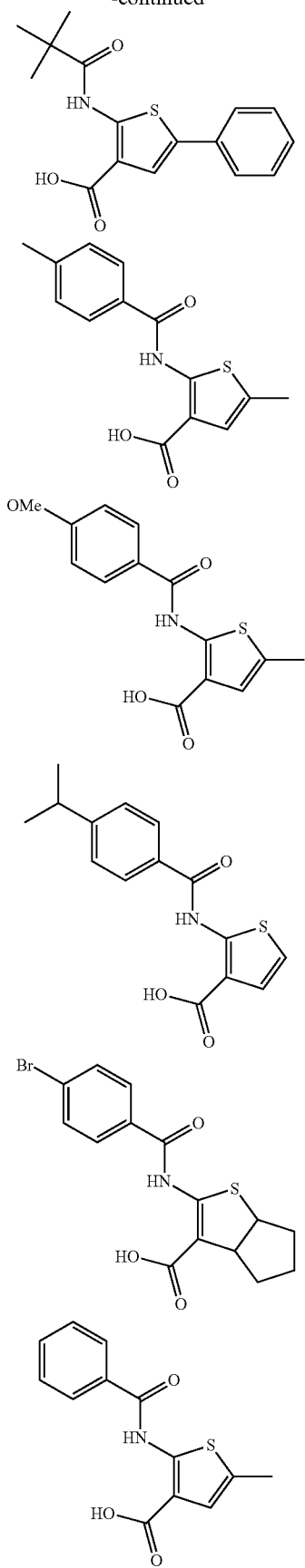
48
-continued
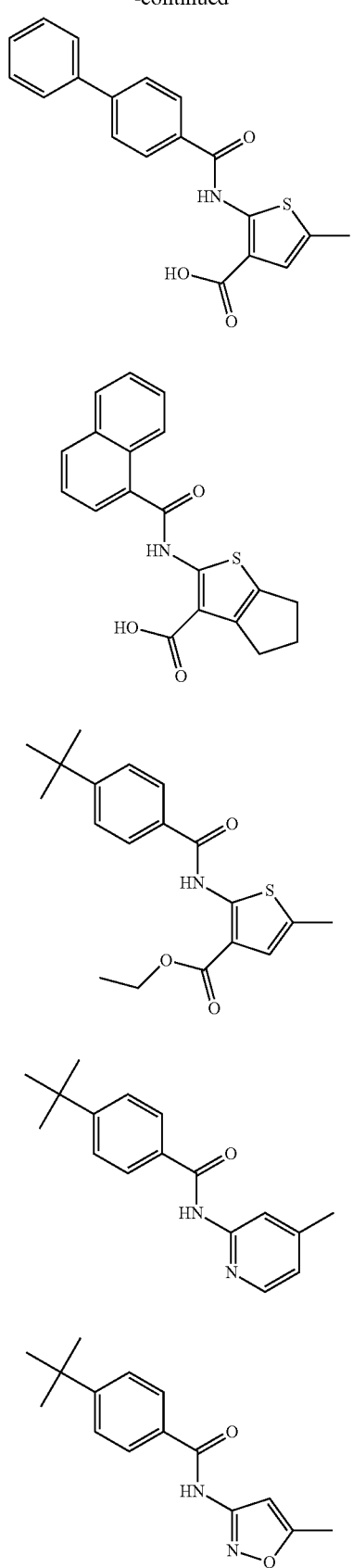

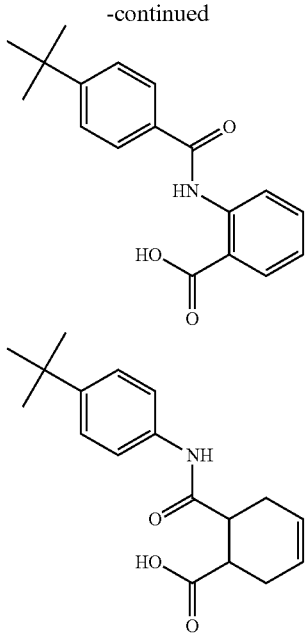

Enantiomers

The compounds described herein may have asymmetric centers and occur as racemates, racemic mixtures, individual diastereomers or enantiomers, with all isomeric forms being included in the present invention. Compounds of the present invention having a chiral center can exist in and be isolated in optically active and racemic forms. Some compounds can exhibit polymorphism. The present invention encompasses racemic, optically-active, polymorphic, or stereoisomeric forms, or mixtures thereof, of a compound of the invention, which possess the useful properties described herein.

In certain embodiments, the compounds are present as enantiomers. In one embodiment, the compound is provided as an enantiomer or mixture of enantiomers. In a particular embodiment, the compound is present as a racemic mixture. The enantiomer can be named by the configuration at the chiral center, such as R or S. In certain embodiments, the compound is present as a racemic mixture of R- and S-enantiomers. In certain embodiments, the compound is present as a mixture of two enantiomers. In one embodiment, the mixture has an enantiomeric excess in R. In one embodiment, the mixture has an enantiomeric excess in S. In certain other embodiments, the compound is in an enantiomeric excess of the R- or S-enantiomer. The enantiomeric excess can be 51% or more, such as 51% or more, 55% or more, 60% or more, 65% or more, 70% or more, 75% or more, 80% or more, 85% or more, 90% or more, 95% or more, 98% or more, or 99% or more in the single enantiomer. The enantiomeric excess can be 51% or more, such as 51% or more, 55% or more, 60% or more, 65% or more, 70% or more, 75% or more, 80% or more, 85% or more, 90% or more, 95% or more, 98% or more, or 99% or more in the R enantiomer. The enantiomeric excess can be 51% or more, such as 51% or more, 55% or more, 60% or more, 65% or more, 70% or more, 75% or more, 80% or more, 85% or more, 90% or more, 95% or more, 98% or more, or 99% or more in the S enantiomer.

In other embodiments, the compound is substantially in the form of a single enantiomer, such as the R or S enantiomer. The phrase "substantially in the form of a single enantiomer" is intended to mean at least 70% or more in the form of a single enantiomer, for example 70% or more, 75% or more, 80% or more, 85% or more, 90% or more, 95% or more, 98% or more, or 99% or more in either the R or S enantiomer.

The enantiomer can be named by the direction in which it rotates the plane of polarized light. If it rotates the light clockwise as seen by the viewer towards whom the light is traveling, the isomer can be labeled (+) and if it rotates the light counterclockwise, the isomer can be labeled (−). In certain embodiments, the compound is present as a racemic mixture of (+) and (−) isomers. In certain embodiments, the compound is present as a mixture of two isomers. In one embodiment, the mixture has an excess in (+). In one embodiment, the mixture has an excess in (−). In certain other embodiments, the compound is in an excess of the (+) or (−) isomer. The isomeric excess can be 51% or more, such as 51% or more, 55% or more, 60% or more, 65% or more, 70% or more, 75% or more, 80% or more, 85% or more, 90% or more, 95% or more, 98% or more, or 99% or more in the (+) isomer. The enantiomeric excess can be 51% or more, such as 51% or more, 55% or more, 60% or more, 65% or more, 70% or more, 75% or more, 80% or more, 85% or more, 90% or more, 95% or more, 98% or more, or 99% or more in the (−) isomer.

In other embodiments, the compound is substantially in the form of a single optical isomer, such as the (+) or (−) isomer. The phrase "substantially in the form of a single optical isomer" is intended to mean at least 70% or more in the form of a single isomer, for example 70% or more, 75% or more, 80% or more, 85% or more, 90% or more, 95% or more, 98% or more, or 99% or more of either the (+) or (−) isomer.

The optically active forms can be prepared by, for example, resolution of the racemic form by recrystallization techniques, by synthesis from optically-active starting materials, by chiral synthesis, or by chromatographic separation using a chiral stationary phase or by enzymatic resolution.

Optically active forms of the compounds can be prepared using any method known in the art, including but not limited to by resolution of the racemic form by recrystallization techniques, by synthesis from optically-active starting materials, by chiral synthesis, or by chromatographic separation using a chiral stationary phase.

Examples of methods to obtain optically active materials include at least the following.

i) physical separation of crystals: a technique whereby macroscopic crystals of the individual enantiomers are manually separated. This technique can be used if crystals of the separate enantiomers exist, i.e., the material is a conglomerate, and the crystals are visually distinct;

ii) simultaneous crystallization: a technique whereby the individual enantiomers are separately crystallized from a solution of the racemate, possible only if the latter is a conglomerate in the solid state;

iii) enzymatic resolutions: a technique whereby partial or complete separation of a racemate by virtue of differing rates of reaction for the enantiomers with an enzyme;

iv) enzymatic asymmetric synthesis: a synthetic technique whereby at least one step of the synthesis uses an enzymatic reaction to obtain an enantiomerically pure or enriched synthetic precursor of the desired enantiomer;

v) chemical asymmetric synthesis: a synthetic technique whereby the desired enantiomer is synthesized from an achiral precursor under conditions that produce asymmetry (i.e., chirality) in the product, which can be achieved using chiral catalysts or chiral auxiliaries;

vi) diastereomer separations: a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations: a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

viii) kinetic resolutions: this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors: a synthetic technique whereby the desired enantiomer is obtained from non-chiral starting materials and where the stereochemical integrity is not or is only minimally compromised over the course of the synthesis;

x) chiral liquid chromatography: a technique whereby the enantiomers of a racemate are separated in a liquid mobile phase by virtue of their differing interactions with a stationary phase (including but not limited to via chiral HPLC). The stationary phase can be made of chiral material or the mobile phase can contain an additional chiral material to provoke the differing interactions;

xi) chiral gas chromatography: a technique whereby the racemate is volatilized and enantiomers are separated by virtue of their differing interactions in the gaseous mobile phase with a column containing a fixed non-racemic chiral adsorbent phase;

xii) extraction with chiral solvents: a technique whereby the enantiomers are separated by virtue of preferential dissolution of one enantiomer into a particular chiral solvent;

xiii) transport across chiral membranes: a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane that allows only one enantiomer of the racemate to pass through.

Chiral chromatography, including but not limited to simulated moving bed chromatography, is used in one embodiment. A wide variety of chiral stationary phases are commercially available.

II. Methods of Preparing the Compounds

General synthetic methods for preparing the compounds described herein are provided below. These synthetic methods are not intended to be limiting. Those of skill in the art are well aware of means for providing various functional groups, derivatives, and protecting groups on aromatic rings and other moieties, and can readily adapt these general methods to synthesize the compounds described herein.

Synthesis of Compounds of Formula A

The compounds of Formula A (also referred to herein as the 1180 class) are members of the class of substituted tetrahydroisoquinolines. Synthesis of these compounds can proceed via two routes. Scheme 5 outlines the synthetic route proceeding through a Bischler-Napieralski cyclization. An appropriately derivatized phenethylamine (1) (or variation thereof with a 5- or 6-membered ring heteroaryl ring in place of the aryl ring) is allowed to react with carboxylic acid 2, or activated derivative thereof, such as an acid halide, to form the corresponding amide (3).

The amide formed is then subjected to a dehydrating agent, such as POCl$_3$ and/or P$_2$O$_5$ to form a dihydroisoquinoline (4) through a Bischler-Napieralski reaction. The newly-formed dihydroisoquinoline can then be reduced with an appropriate hydride source, such as NaBH$_4$, to the subsequent tetrahydroisoquinoline (5). An appropriate chiral hydride source could provide access to optically-enriched or optically-pure product. Alternatively, enantiomers can be obtained using a variety of resolution techniques that are well known to those skilled in the art. The tetrahydroisoquinoline is then allowed to react with an appropriately substituted acyl chloride, activated carboxylic acid, or alkyl halide.

Although the aryl rings in Scheme 1 are shown as phenyl, the chemistry works with other aryl and heteroaryl rings, as described herein, so long as the J substituents either do not react with the functional groups involved in the coupling chemistry, or the J substituents are suitably protected so that they do not so interfere.

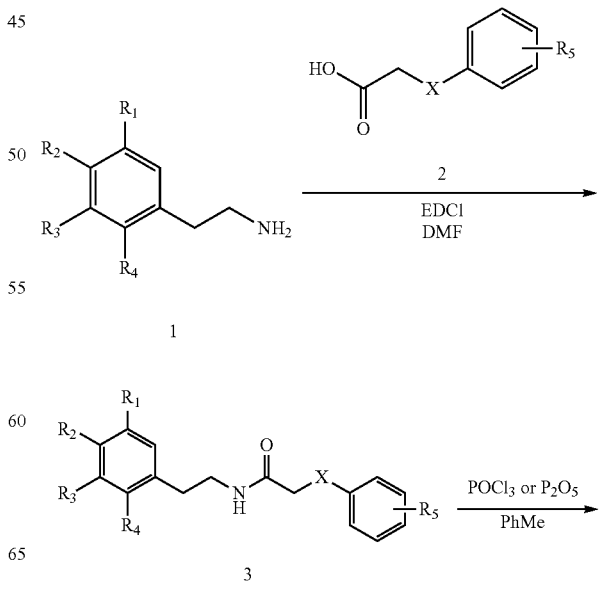

Scheme 1. Synthesis of 1180 series analogues—Route 1

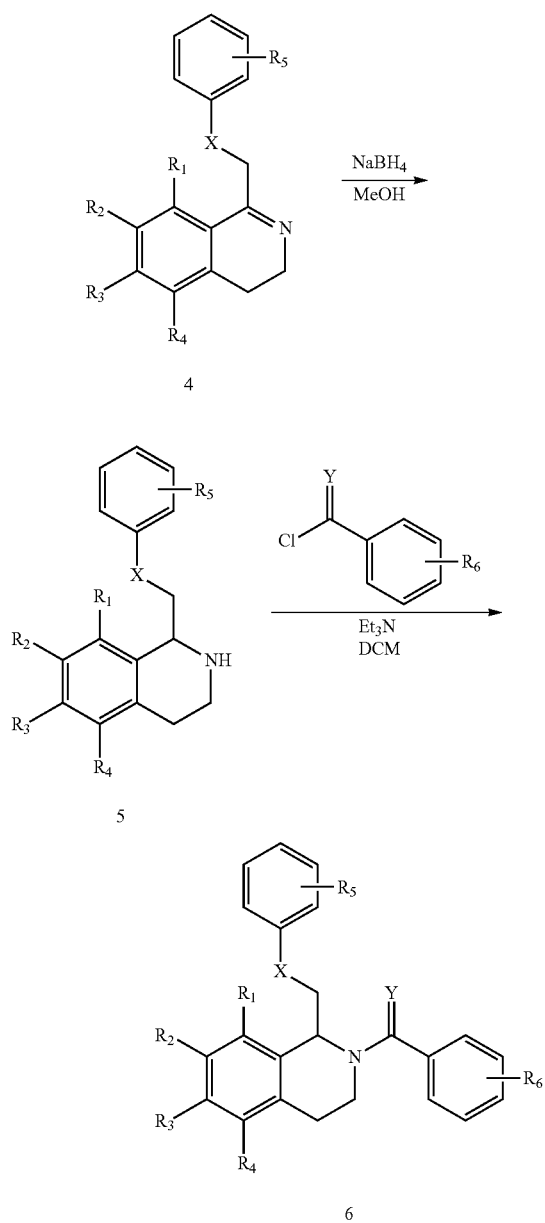

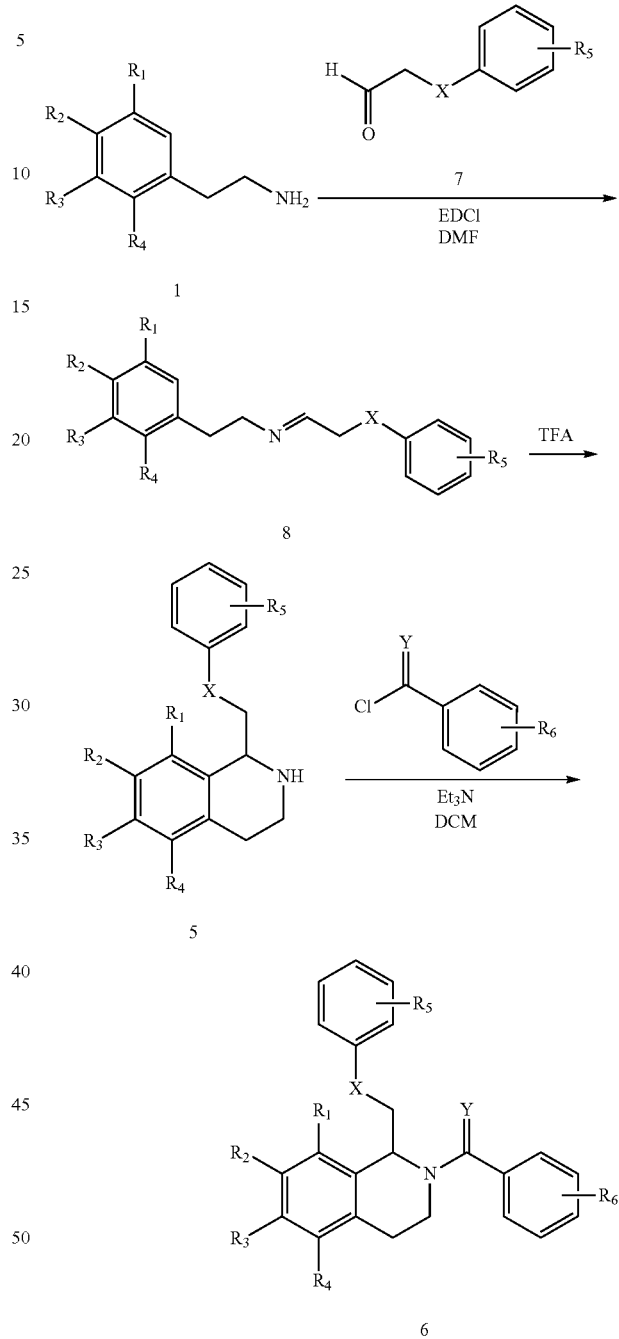

Scheme 2. Synthesis of 1180 series analogues.—Route 2

In Scheme 1, $R_1$-$R_6$ are independently H, OMe, OH, SH, SMe, Cl, F, I, Br, $C_{1-6}$ alkyl, $C_{6-10}$ aryl, alkylaryl, and arylalkyl, and substituted versions of the alkyl, aryl, aralkyl, and alkylaryl moieties, as defined herein, X=NH, NR where R is an alkyl or aryl substituent, O, S, CH2, or CHR where R is $C_{1-6}$ alkyl, $C_{6-10}$ aryl, alkylaryl, and arylalkyl, and substituted versions of the alkyl, aryl, aralkyl, and alkylaryl moieties, as defined herein, Y=S, NH, NR (where R is same as above), CH2, CR2, CHR, or O.

In Scheme 2, an appropriately functionalized phenethylamine (1) is allowed to react with an aldehyde (7) to form the imine 8. The imine is then cyclized via Pictet-Spengler reaction conditions to form the tetrahydroisoquinoline 5. The tetrahydroisoquinoline is then allowed to react with an appropriately substituted acid chloride, activated carboxylic acid, or alkyl halide.

The various substituents in Scheme 2 are defined in the same manner as in Scheme 1.

Representative syntheses of compounds of Formulas I and J are shown below:

Cyclic ketones 1 are reacted with ethyl cyanoacetate 2 and sulfur with a catalytic amount of morpholine in ethanol to give amino thiophenes 3 in generally moderate to good yields. Compounds 3 will be reacted with acyl chlorides to give amides 4 in moderate to excellent yields. Ester hydrolysis

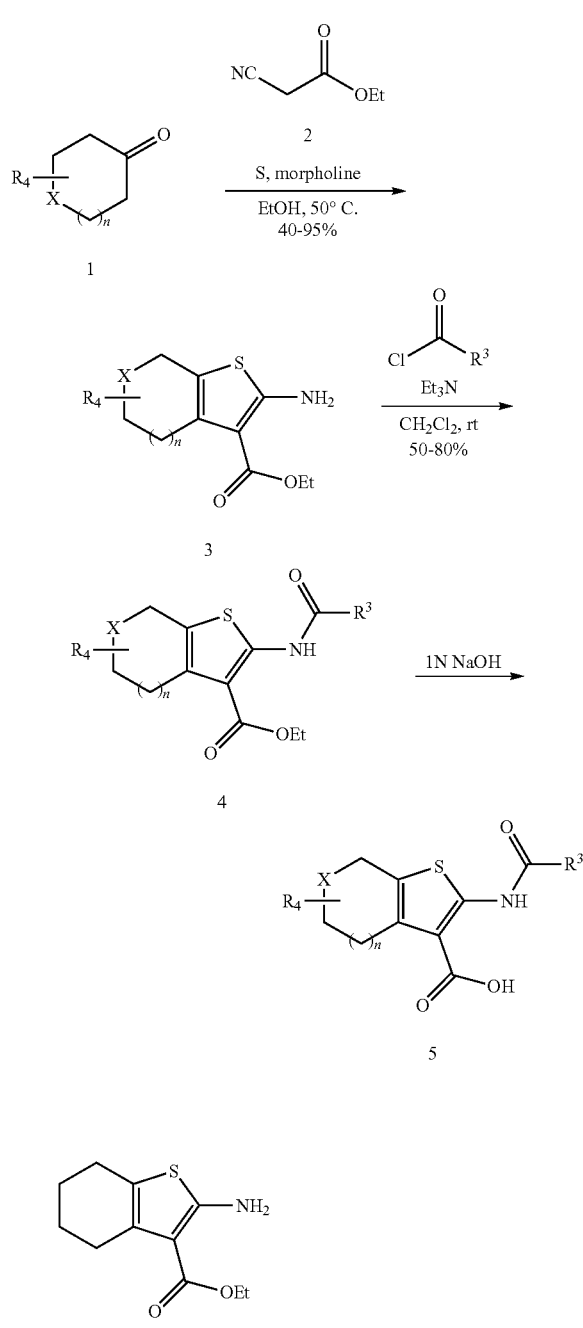

Ethyl 2-amino-4,5,6,7-tetrahydrobenzo[b]thiophene-3-carboxyate

Andersen, H. S.; Olsen, O. H.; Iversen, L. F.; Sørensen, A. L. P.; Mortensen, S. B.; Christensen, M. S.; Branner, S.; Hansen, T. K.; Lau, J. F.; Jeppesen, L.; Moran, E. J.; Su, J.; Bakir, F.; Judge, L.; Shahbaz, M.; Collins, T.; Vo, T.; Newman, M. J.; Ripka, W. C.; Møller, N. P. H. *J. Med. Chem.* 2002, 45, 4443-4459.

To a solution of cyclohexanone (5.0 g, 51 mmol), ethylcyanoacetate (5.96 mL, 56 mmol, 1.1 equiv) and sulfur (1.80 g, 56 mmol, 1.1 equiv) in absolute ethanol (150 mL), was added morpholine (6.7 mL, 76 mmol, 1.5 equiv). The yellow mixture was heated to 50° C. for 16 h. The brownish solution was evaporated and the resulting solid was dissolved in ethyl acetate (100 mL), washed with water (2×50 mL) and brine (2×50 mL) and dried over magnesium sulfate. The solvent was evaporated and the crude product was subjected to purification by chromatography on silica gel column, using hexanes/ethyl acetate 10:1 v/v as the eluent. The expected compound was isolated as an off-white powder (10.40 g, 91%).

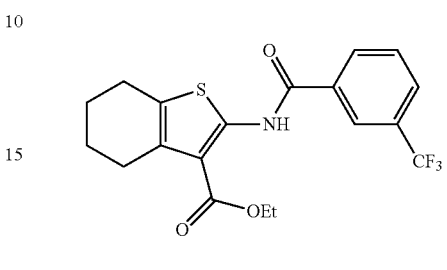

Ethyl 2-(3-(trifluoromethyl)benzamido)-4,5,6,7-tetrahydrobenzo[b]thiophene-3-carboxylate Pittallá, V; Modica, M.; Romeo, G.; Materia, L.; Salerno, L.; Siracusa, M.; Cagnotto, A.; Merghetti, I.; Russo, F. *Il Farmaco* 2005, 60, 711-720

A solution of 3-trifluorobenzoyl chloride (0.300 g, 1.33 mmol), ethyl 2-amino-4,5,6,7-tetrahydrobenzo[b]thiophene-3-carboxylate (200 mL, 1.33 mmol, 1 equiv) and triethylamine (260 mL, 1.86 mmol, 1.4 equiv) in dichloromethane (5.4 mL) was stirred for 2 h at room temperature. The reaction mixture was then diluted with dichloromethane. The organic layer was washed with an aqueous 1N solution of sodium hydroxide (3×10 mL) and brine (10 mL), dried over magnesium sulfate, filtered and evaporated under reduced pressure. The crude product was purified by silica gel chromatography using hexanes/ethyl acetate 10:1 v/v as the eluent. The expected compound was obtained as a yellow solid (0.455 g, 86%).

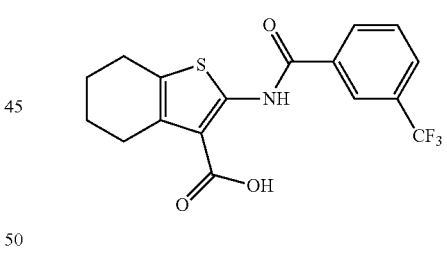

2-(3-(Trifluoromethyl)benzamido)-4,5,6,7-tetrahydrobenzo[b]thiophene-3-carboxylic acid Pittallá, V; Modica, M.; Romeo, G.; Materia, L.; Salerno, L.; Siracusa, M.; Cagnotto, A.; Merghetti, L; Russo, F. *Il Farmaco* 2005, 60, 711-720

A solution of the previous ethyl ester (0.300 g, 0.75 mmol) was added to a 2N aqueous solution of sodium hydroxide (1.6 mL) in ethanol (8 mL). The mixture was heated at 90° C. for 2 h. After cooling, the mixture was acidified with concentrated aqueous hydrochloric acid and the precipitate was filtered and washed with cold water to afford the expected product as a white solid (0.170 g, 61%).

The intention of this application is to encompass all existing stereoisomers of all compounds present. Methods to prepare or resolve, isolate and evaluate the individual isomers are well known by those skilled in the art. These approaches include the use of chiral auxiliaries, chiral catalysts, kinetic resolution, chiral high-performance liquid chromatography (HPLC), classical resolution, and the like (Gremmen et al 2001; Kanemitsu et al 2006; Paal et al 2008; Piwowarczyk et al 2008; Schuster et al 2007).

III. Pharmaceutical Compositions Including the Compounds

Mammals, and specifically humans, suffering from schizophrenia, Parkinson's disease, depression, neuropathic pain, stroke, traumatic brain injury, epilepsy, and other neurologic events or neurodegeneration involving NMDA receptor activation, or any of the above-described conditions, can be treated by either targeted or systemic administration, via oral, inhalation, topical, trans- or sub-mucosal, subcutaneous, parenteral, intramuscular, intravenous or transdermal administration of a composition comprising an effective amount of the compounds described herein or a pharmaceutically acceptable salt, ester or prodrug thereof, optionally in a pharmaceutically acceptable carrier. The compounds or composition is typically administered by oral administration. Alternatively, compounds can be administered by inhalation. In another embodiment, the compound is administered transdermally (for example via a slow release patch), or topically. In yet another embodiment, the compound is administered subcutaneously, intravenously, intraperitoneally, intramuscularly, parenterally, or submucosally. In any of these embodiments, the compound is administered in an effective dosage range to treat the target condition.

In one embodiment, compounds of the present invention are administered orally. Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition.

When the compound is administered orally in the form of a dosage unit such as a tablets, pills, capsules, troches and the like, these can contain any of the following ingredients, or compounds of a similar nature: a binder (such as microcrystalline cellulose, gum tragacanth or gelatin); an excipient (such as starch or lactose), a disintegrating agent (such as alginic acid, Primogel, or corn starch); a lubricant (such as magnesium stearate or Sterotes); a glidant (such as colloidal silicon dioxide); a sweetening agent (such as sucrose or saccharin); and/or a flavoring agent (such as peppermint, methyl salicylate, or orange flavoring). When the dosage unit form is a capsule, it can contain, in addition to material of the above type, a liquid carrier (such as a fatty oil). In addition, dosage unit forms can contain various other materials which modify the physical form of the dosage unit, for example, coatings of sugar, shellac, or other enteric agents. The compound or its salts can also be administered orally as a component of an elixir, suspension, syrup, wafer, chewing gum or the like. A syrup may contain, in addition to the active compounds, a sweetening agent (such as sucrose, saccharine, etc.) and preservatives, dyes and colorings and flavors.

The compounds of the invention may be also administered in specific, measured amounts in the form of an aqueous suspension by use of a pump spray bottle. The aqueous suspension compositions of the present invention may be prepared by admixing the compounds with water and other pharmaceutically acceptable excipients. The aqueous suspension compositions according to the present invention may contain, inter alia, water, auxiliaries and/or one or more of the excipients, such as: suspending agents, e.g., microcrystalline cellulose, sodium carboxymethylcellulose, hydroxpropyl-methyl cellulose; humectants, e.g. glycerin and propylene glycol; acids, bases or buffer substances for adjusting the pH, e.g., citric acid, sodium citrate, phosphoric acid, sodium phosphate as well as mixtures of citrate and phosphate buffers; surfactants, e.g. Polysorbate 80; and antimicrobial preservatives, e.g., benzalkonium chloride, phenylethyl alcohol and potassium sorbate. In a separate embodiment, the compounds of the invention are in the form of an inhaled dosage. In this embodiment, the compounds may be in the form of an aerosol suspension, a dry powder or liquid particle form. The compounds may be prepared for delivery as a nasal spray or in an inhaler, such as a metered dose inhaler. Pressurized metered-dose inhalers ("MDI") generally deliver aerosolized particles suspended in chlorofluorocarbon propellants such as CFC-11, CFC-12, or the non-chlorofluorocarbons or alternate propellants such as the fluorocarbons, HFC-134A or HFC-227 with or without surfactants and suitable bridging agents. Dry-powder inhalers can also be used, either breath activated or delivered by air or gas pressure such as the dry-powder inhaler disclosed in the Schering Corporation International Patent Application No. PCT/US92/05225, published 7 Jan. 1993 as well as the Turbuhaler™ (available from Astra Pharmaceutical Products, Inc.) or the Rotahaler™ (available from Allen & Hanburys) which may be used to deliver the aerosolized particles as a finely milled powder in large aggregates either alone or in combination with some pharmaceutically acceptable carrier e.g. lactose; and nebulizers. Solutions or suspensions used for parenteral, intradermal, subcutaneous, or topical application can include at least some of the following components: a sterile diluent (such as water for injection, saline solution, fixed oils, polyethylene glycols, glycerine, propylene glycol or other synthetic solvents); antibacterial agents (such as benzyl alcohol or methyl parabens); antioxidants (such as ascorbic acid or sodium bisulfite); chelating agents (such as ethylenediaminetetraacetic acid); buffers (such as acetates, citrates or phosphates); and/or agents for the adjustment of tonicity (such as sodium chloride or dextrose). The pH of the solution or suspension can be adjusted with acids or bases, such as hydrochloric acid or sodium hydroxide.

A parenteral preparation can be enclosed in ampoules, disposable syringes or multiple dose vials made of glass or plastic.

Suitable vehicles or carriers for topical application can be prepared by conventional techniques, such as lotions, suspensions, ointments, creams, gels, tinctures, sprays, powders, pastes, slow-release transdermal patches, suppositories for application to rectal, vaginal, nasal or oral mucosa. In addition to the other materials listed above for systemic administration, thickening agents, emollients, and stabilizers can be used to prepare topical compositions. Examples of thickening agents include petrolatum, beeswax, xanthan gum, or polyethylene, humectants such as sorbitol, emollients such as mineral oil, lanolin and its derivatives, or squalene.

If administered intravenously, carriers can be physiological saline, bacteriostatic water, Cremophor EL™ (BASF, Parsippany, N.J.) or phosphate buffered saline (PBS). In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) are also preferred as pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the compound is then introduced into the container. The container is then swirled by hand to free lipid material from the sides of the container and to disperse lipid aggregates, thereby forming the liposomal suspension.

Dosing

The compound is administered for a sufficient time period to alleviate the undesired symptoms and the clinical signs associated with the condition being treated. In one embodiment, the compounds are administered less than three times daily. In one embodiment, the compounds are administered in one or two doses daily. In one embodiment, the compounds are administered once daily. In some embodiments, the compounds are administered in a single oral dosage once a day. The active compound is included in the pharmaceutically acceptable carrier or diluent in an amount sufficient to deliver to a patient a therapeutic amount of compound in vivo in the absence of serious toxic effects. An effective dose can be readily determined by the use of conventional techniques and by observing results obtained under analogous circumstances. In determining the effective dose, a number of factors are considered including, but not limited to: the species of patient; its size, age, and general health; the specific disease involved; the degree of involvement or the severity of the disease; the response of the individual patient; the particular compound administered; the mode of administration; the bioavailability characteristics of the preparation administered; the dose regimen selected; and the use of concomitant medication.

Typical systemic dosages for the herein described conditions are those ranging from 0.01 mg/kg to 1500 mg/kg of body weight per day as a single daily dose or divided daily doses. Preferred dosages for the described conditions range from 0.5-1500 mg per day. A more particularly preferred dosage for the desired conditions ranges from 5-750 mg per day. Typical dosages can also range from 0.01 to 1500, 0.02 to 1000, 0.2 to 500, 0.02 to 200, 0.05 to 100, 0.05 to 50, 0.075 to 50, 0.1 to 50, 0.5 to 50, 1 to 50, 2 to 50, 5 to 50, 10 to 50, 25 to 50, 25 to 75, 25 to 100, 100 to 150, or 150 or more mg/kg/day, as a single daily dose or divided daily doses. In one embodiment, the daily dose is between 10 and 500 mg/day. In another embodiment, the dose is between about 10 and 400 mg/day, or between about 10 and 300 mg/day, or between about 20 and 300 mg/day, or between about 30 and 300 mg/day, or between about 40 and 300 mg/day, or between about 50 and 300 mg/day, or between about 60 and 300 mg/day, or between about 70 and 300 mg/day, or between about 80 and 300 mg/day, or between about 90 and 300 mg/day, or between about 100 and 300 mg/day, or about 200 mg/day. In one embodiment, the compounds are given in doses of between about 1 to about 5, about 5 to about 10, about 10 to about 25 or about 25 to about 50 mg/kg. Typical dosages for topical application are those ranging from 0.001 to 100% by weight of the active compound.

The concentration of active compound in the drug composition will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the dosage ranges set forth herein are exemplary only and are not intended to limit the scope or practice of the claimed composition. The active ingredient may be administered at once, or may be divided into a number of smaller doses to be administered at varying intervals of time.

Combination Treatment

The compound can also be mixed with other active materials which do not impair the desired action, or with materials that supplement the desired action. The active compounds can be administered in conjunction, i.e. combination or alternation, with other medications used in the treatment or prevention schizophrenia, Parkinson's disease, depression, neuropathic pain, stroke, traumatic brain injury, epilepsy, as well as other neurologic events, neurological disorders, or neurodegenerative conditions. In another embodiment, the compounds can be administered in conjunction (combination or alternation) with other medications used in treatment or prophylaxis of inflammatory conditions. In certain embodiments, the combination can be synergistic although in other embodiments the combination is not synergistic.

IV. Methods of Treatment Using the Compounds

In one embodiment, the compounds are used in a method of treatment or prophylaxis of schizophrenia, bipolar disorder, depression, anxiety, neuropsychiatric or mood disorders, obsessive-compulsive disorder, neurocognitive disorders, pre-senile dementia, motor dysfunction or motor disorders, tardive dyskinesia, neuropathic pain, inflammatory pain, Parkinson's disease, Alzheimer's disease, amyolateral sclerosis (ALS), Huntington's chorea, epilepsy, traumatic brain injury, ischemic and hemorrhagic stroke, subarachnoid hemorrhage, cerebral vasospasm, ischemia, hypoxia, or neurodegeneration involving NMDA receptor activation comprising administering to a host in need thereof an effective amount of a compound of any of Claims 1-9, optionally in a pharmaceutically acceptable carrier. The compounds can be administered, alone or in a pharmaceutically-acceptable carrier, to treat, prevent, or reduce the symptoms of the various disorders.

The compounds described herein can also generally be used to treat neurologic events and neurodegeneration, whether or not such neurologic event or neurodegeneration is associated with NMDA receptor activation.

The compounds described herein can also generally be used to treat patients who are under the actions of an NMDA receptor antagonists such as PCP or ketamine.

In some embodiments, the compounds are used to treat or prevent stroke or stroke damage, and can be administered under emergency care for a stroke, for maintenance treatment of stroke, and/or for rehabilitation of stroke.

In other embodiments, the compounds are used to provide cognitive enhancement, in normal or cognitively deficient individuals.

In another embodiment, the compounds are used to improve rehabilitative training after stroke, head injury, ischemia, hypoxia, or any acute brain injury.

In one embodiment, methods are provided to treat patients with ischemic injury or hypoxia, or prevent or treat the neuronal toxicity associated with ischemic injury or hypoxia, by administering a compound or composition described herein. In one aspect of this embodiment, the ischemic injury is vasospasm after subarachnoid hemorrhage.

A subarachnoid hemorrhage refers to an abnormal condition in which blood collects beneath the arachnoid mater, a membrane that covers the brain. This area, called the subarachnoid space, normally contains cerebrospinal fluid. The accumulation of blood in the subarachnoid space and the vasospasm of the vessels which results from it can lead to stroke, seizures, and other complications. The methods and compounds described herein can be used to treat patients experiencing a subarachnoid hemorrhage. In one embodiment, the methods and compounds described herein can be used to limit the toxic effects of the subarachnoid hemorrhage, including, for example, stroke and/or ischemia that can result from the subarachnoid hemorrhage. In a particular embodiment, the methods and compounds described herein can be used to treat patients with traumatic subarachnoid hemorrhage. On one embodiment, the traumatic subarachnoid hemorrhage can be due to a head injury. In another embodiment, the patients can have a spontaneous subarachnoid hemorrhage.

In other embodiments, the ischemic injury is selected from, but not limited to, one of the following: traumatic brain injury, cognitive deficit after traumatic brain injury or cerebral ischemia, cognitive deficit after cerebral hypoxia, cognitive deficit after bypass surgery, cognitive deficit after carotid angioplasty; and cognitive deficit after neonatal ischemia following hypothermic circulatory arrest.

In another embodiment, methods are provided to treat patients with brain tumors, such as gliomas, by administering a compound selected according to the methods or processes described herein.

Further, the methods described herein can be used prophylactically to prevent or protect against such diseases or neurological conditions, such as those described herein. In one embodiment, patients with a predisposition for an ischemic event, such as a genetic predisposition, can be treated prophylactically with the methods and compounds described herein. In another embodiment, patients that exhibit vasospasms can be treated prophylactically with the methods and compounds described herein. In a further embodiment, patients that have undergone cardiac bypass surgery can be treated prophylactically with the methods and compounds described herein.

In one embodiment, methods are provided to treat patients with ischemic injury or hypoxia, or prevent or treat the neuronal toxicity associated with ischemic injury or hypoxia, by administering a compound selected according to the methods or processes described herein.

In another embodiment, methods are provided to treat patients with inflammatory pain or neuropathic pain or related disorders by administering a compound selected according to the methods or processes described herein. In certain embodiments, the neuropathic pain or related disorder can be selected from the group including, but not limited to: peripheral diabetic neuropathy, postherpetic neuralgia, complex regional pain syndromes, peripheral neuropathies, chemotherapy-induced neuropathic pain, cancer neuropathic pain, neuropathic low back pain, HIV neuropathic pain, trigeminal neuralgia, and/or central post-stroke pain.

Neuropathic pain can be associated with signals generated ectopically and often in the absence of ongoing noxious events by pathologic processes in the peripheral or central nervous system. This dysfunction can be associated with common symptoms such as allodynia, hyperalgesia, intermittent abnormal sensations, and spontaneous, burning, shooting, stabbing, paroxysmal or electrical-sensations, paresthesias, hyperpathia and/or dysesthesias, which can also be treated by the compounds and methods described herein. Further, the compounds and methods described herein can be used to treat neuropathic pain resulting from peripheral or central nervous system pathologic events, including, but not limited to trauma, ischemia; infections or from ongoing metabolic or toxic diseases, infections or endocrinologic disorders, including, but not limited to, diabetes mellitus, diabetic neuropathy, amyloidosis, amyloid polyneuropathy (primary and familial), neuropathies with monoclonal proteins, vasculitic neuropathy, HIV infection, herpes zoster—shingles and/or postherpetic neuralgia; neuropathy associated with Guillain-Barre syndrome; neuropathy associated with Fabry's disease; entrapment due to anatomic abnormalities; trigeminal and other CNS neuralgias; malignancies; inflammatory conditions or autoimmune disorders, including, but not limited to, demyelinating inflammatory disorders, rheumatoid arthritis, systemic lupus erythematosus, Sjogren's syndrome; and cryptogenic causes, including, but not limited to idiopathic distal small-fiber neuropathy. Other causes of neuropathic pain that can be treated according to the methods and compositions described herein include, but are not limited to, exposure to toxins or drugs (such as aresnic, thallium, alcohol, vincristine, cisplatinum and dideoxynucleosides), dietary or absorption abnormalities, immuno-globulinemias, hereditary abnormalities and amputations (including mastectomy). Neuropathic pain can also result from compression of nerve fibers, such as radiculopathies and carpal tunnel syndrome.

The compounds can also be used to treat the following diseases or neurological conditions, including, but not limited to: chronic nerve injury, chronic pain syndromes, such as, but not limited to ischemia following transient or permanent vessel occlusion, seizures, spreading depression, restless leg syndrome, hypocapnia, hypercapnia, diabetic ketoacidosis, fetal asphyxia, spinal cord injury, status epilepticus, concussion, migraine, hypocapnia, hyperventilation, lactic acidosis, fetal asphyxia during parturition, and/or retinopathies by administering a compound selected according to the methods or processes described herein.

In one embodiment, the use of the compounds of the invention reduces symptoms of neuropathic pain, stroke, traumatic brain injury, epilepsy, and other neurologic events or neurodegeneration resulting from NMDA receptor activation.

Alzheimer's Disease

Senile dementia of the Alzheimer's type (SDAT) is a debilitating neurodegenerative disease, mainly afflicting the elderly, characterized by a progressive intellectual and personality decline, as well as a loss of memory, perception, reasoning, orientation and judgment. One feature of the disease is an observed decline in the function of cholinergic systems, and specifically, a severe depletion of cholinergic neurons (i.e., neurons that release acetylcholine, which is believed to be a neurotransmitter involved in learning and memory mechanisms). See, for example, Jones et al., Intern. J. Neurosci. 50:147 (1990); Perry, Br. Med. Bull. 42:63 (1986); and Sitaram et al., Science 201:274 (1978).

A dysfunction of glutamatergic neurotransmission is hypothesized to be involved in the etiology of Alzheimer's disease. Targeting the glutamatergic system, specifically NMDA receptors, offers a novel approach to treatment in view of the limited efficacy of existing drugs targeting the cholinergic system. Cacabelos R, Takeda M, Winblad B (January 1999). "The glutamatergic system and neurodegeneration in dementia: preventive strategies in Alzheimer's disease". Int J Geriatr. Psychiatry 14 (1):3-47. By binding to the NMDA receptor the NMDA receptor potentiators described herein are able to enhance the prolonged influx of $Ca^{2+}$ ions which forms the basis of neuronal plasticity, and is thought to be involved in learning and memory. In addition, glutamate receptors are intimately involved in the molecular substrates of cognition, learning and memory formation. Glutamate receptor modulators have been hypothesized to be capable of influencing cognition and memory formation. Thus, manipulation of the glutamate system by subunit-selective NMDA receptor potentiators described here could provide beneficial relief to patients suffering from Alzheimer's, other forms of dementia, as well as other neurological conditions that involve impaired judgment, memory, or cognition.

Parkinson's Disease

Parkinson's disease (PD) is a debilitating neurodegenerative disease, presently of unknown etiology, characterized by tremors, muscular rigidity. A feature of the disease appears to involve the progressive degeneration of dopaminergic neurons (i.e., which secrete dopamine). One symptom of the disease has been observed to be a concomitant loss of nicotinic receptors which are associated with such dopaminergic neurons, and which are believed to modulate the process of dopamine secretion. See Rinne et al., Brain Res. 54:167 (1991) and Clark et al., Br. J. Pharm. 85:827 (1985).

N-Methyl-D-aspartate (NMDA) glutamate receptors are a class of excitatory amino acid receptors, which have several important functions in the motor circuits of the basal ganglia, and are viewed as important targets for the development of new drugs to prevent or treat Parkinson's disease (PD). NMDA receptors are ligand-gated ion channels composed of multiple subunits, each of which has distinct cellular and regional patterns of expression. They have complex regulatory properties, with both agonist and co-agonist binding sites and regulation by phosphorylation and protein-protein interactions. They are found in all of the structures of the basal ganglia, although the subunit composition in the various structures is different. NMDA receptors present in the striatum are crucial for dopamine-glutamate interactions. The abundance, structure, and function of striatal receptors are altered by the dopamine depletion and further modified by the pharmacological treatments used in PD. Given the expression of NR2C and NR2D subunits on key neurons such as the dopamine releasing substantia nigra pars compacta neurons, it is possible that the subunit-selective NMDA receptor potentiators described here could find some use in cognitive effects of Parkinson's disease, or in the enhancement of dopamine signalling.

Tardive Diskinesia and Other Motor Disorders

In one embodiment, the invention relates to a method of treating tardive dyskinesia in humans.

In one aspect, the invention reduces involuntary movements or hyperkinesia characteristic of patients with tardive movement disorders, including tardive dyskinesia, by administering an NMDA receptor potentiator as defined herein. The NMDA receptor potentiators could also be useful for the treatment of other motor disorders ranging from resting tremor to various dyskinesias. The NR2C subunit is abundantly expressed in the cerebellum, a structure that is involved in fine motor coordination. Thus, the compounds described here that act on the NR2C subunit could enhance motor function in a beneficial way for a large number of patients.

By enhancing cognition and memory, the compounds described here that alter the NR2C and NR2D subunit activity could be beneficial in facilitating rehabilitation after brain injury of any type. Such compounds might enhance motor reprogramming during physical therapy, thereby increasing functionality and speeding recovery.

In all of these embodiments, the methods involve administering to a host in need thereof an effective amount of a compound of any of the formulas described herein, or a pharmaceutically acceptable salt, ester, or derivative thereof, or a pharmaceutical composition thereof.

Side Effects

In an additional aspect of the methods and processes described herein, the compound does not exhibit substantial toxic an/or psychotic side effects. Toxic side effects include, but are not limited to, agitation, hallucination, confusion, stupor, paranoia, delirium, psychotomimetic-like symptoms, rotorod impairment, amphetamine-like stereotyped behaviors, stereotypy, psychosis memory impairment, motor impairment, anxiolytic-like effects, increased blood pressure, decreased blood pressure, increased pulse, decreased pulse, hematological abnormalities, electrocardiogram (ECG) abnormalities, cardiac toxicity, heart palpitations, motor stimulation, psychomotor performance, mood changes, short-term memory deficits, long-term memory deficits, arousal, sedation, extrapyramidal side-effects, ventricular tachycardia, and lengthening of cardiac repolarization, ataxia, cognitive deficits and/or schizophrenia-like symptoms.

In one embodiment, the compound is a selective NR1/NR2C NMDA receptor and/or a NR1/NR2D NMDA receptor potentiator. In one particular embodiment, the compounds can bind to the NR2C or NR2D subunits of the NMDA receptor regardless of the other subunits that are present. In another particular embodiment, the compounds are selective for the NR2C or NR2D subunits of the NMDA receptor. In a further additional or alternative embodiment, the compound has a therapeutic index equal to or greater than at least 2:1, at least 3:1, at least 4:1, at least 5:1, at least 6:1, at least 7:1, at least 8:1, at least 9:1, at least 10:1, at least 15:1, at least 20:1, at least 25:1, at least 30:1, at least 40:1, at least 50:1, at least 75:1, at least 100:1 or at least 1000:1. The therapeutic index can be defined as the ratio of the dose required to produce toxic or lethal effects to dose required to produce therapeutic responses. It can be the ratio between the median toxic dose (the dosage at which 50% of the group exhibits the adverse effect of the drug) and the median effective dose (the dosage at which 50% of the population respond to the drug in a specific manner). The higher the therapeutic index, the more safe the drug is considered to be. It simply indicates that it would take a higher dose to invoke a toxic response that it does to cause a beneficial effect.

The side effect profile of compounds can be determined by any method known to those skilled in the art. In one embodiment, motor impairment can be measured by, for example, measuring locomotor activity and/or rotorod performance. Rotorod experiments involve measuring the duration that an animal can remain on an accelerating rod. In another embodiment, memory impairment can be assessed, for example, by using a passive avoidance paradigm; Sternberg memory scanning and paired words for short-term memory, or delayed free recall of pictures for long-term memory. In a further embodiment, anxiolytic-like effects can be measured, for example, in the elevated plus maze task. In other embodiments, cardiac function can be monitored, blood pressure and/or body temperature measured and/or electrocardiograms conducted to test for side effects. In other embodiments, psychomotor functions and arousal can be measured, for example by analyzing critical flicker fusion threshold, choice reaction time, and/or body sway. In other embodiments, mood can be assessed using, for example, self-ratings. In further embodiments, schizophrenic symptoms can be evaluated, for example, using the PANSS, BPRS, and CGI, side-effects were assessed by the HAS and the S/A scale.

In one embodiment, the compound does not exhibit substantial toxic side effects, such as, for example, motor impairment or cognitive impairment. In a particular embodiment, the compound has a therapeutic index equal to or greater than at least 2. In another embodiment, the compound is at least 10 times more selective for binding to an NMDA receptor than any other glutamate receptor. In certain embodiments, the compound interacts with hERG channels at an $EC_{50}$ at least 10 times the $EC_{50}$ for potentiation of an NMDA receptor.

Use of NMDA Receptor Potentiators to Inhibit Drug Tolerance and Dependence and Assist with Withdrawal, Including Smoking Cessation and Opiate Withdrawal Potentiators of the NMDA receptor, i.e., compounds that increase the current flow through the channel, can modify cognitive function and potentially enhance certain forms of learning. By using the compounds described herein, one can treat tolerance and dependence induced by opiate analgesics, and assist with smoking cessation, without producing unwanted side effects such as schizophrenia-like symptoms, loss of normal NMDA receptor-mediated synaptic plasticity (which can possibly affect learning and memory), amnesia, confusional states, and muscle relaxation caused by the non-selective NMDA antagonists of the prior art. Thus, the compounds can be used along with opiates to manage chronic pain in severely ill patients and alleviate the pain of withdrawal both in legitimate and illegitimate drug users.

Use of NMDA Receptor Potentiators with Specificity for the NMDA 2D Subtype in Treating Bone Disorders Bone formation, or osteogenesis, refers to the creation of new bone mass. This includes the process whereby new bone structure grows or the density of existing bone is increased. Osteoblasts form bone by producing extracellular organic matrix, or osteoid and then mineralizing the matrix to form bone. The main mineral component of bone is crystalline hydroxyapetite, which comprises much of the mass of normal adult bone.

In an embodiment of the invention the mammal is a human in need of enhanced bone formation. In one aspect, the human in need has a bone deficit, which means that they will have less bone than desirable or that the bone will be less dense or strong than desired. A bone deficit may be localized, such as that caused by a bone fracture or systemic, such as that caused by osteoporosis. Bone deficits may result from a bone remodeling disorder whereby the balance between bone formation and bone resorption is shifted, resulting in a bone deficit. Examples of such bone remodeling disorders include osteoporosis, Paget's disease, osteoarthritis, rheumatoid arthritis, achondroplasia, osteochodrytis, hyperparathyroidism, osteogenesis imperfecta, congenital hypophosphatasia, fribromatous lesions, fibrous displasia, multiple myeloma, abnormal bone turnover, osteolytic bone disease and periodontal disease. Bone remodelling disorders includes metabolic bone diseases which are characterised by disturbances in the organic matrix, bone mineralization, bone remodelling, endocrine, nutritional and other factors which regulate skeletal and mineral homeostasis. Such disorders may be hereditary or acquired and generally are systemic affecting the entire skeletal system.

In one aspect, the mammal may have a bone remodeling disorder. Bone remodeling as used herein refers to the process whereby old bone is being removed and new bone is being formed by a continuous turnover of bone matrix and mineral that involves bone resorption by osteoclasts and bone formation by osteoblasts.

Osteoporosis is a common bone remodelling disorder characterised by a decrease in bone density of normally mineralised bone, resulting in thinning and increased porosity of bone cortices and trabeculae. The skeletal fragility caused by osteoporosis predisposes sufferers to bone pain and an increased incidence of fractures. Progressive bone loss in this condition may result in a loss of up to 50% of the initial skeletal mass.

Primary osteoporosis includes idiopathic osteoporosis which occurs in children or young adults with normal gonadal function, Type I osteoporosis, also described as post-menauposal osteoporosis, and Type II osteoporosis, senile osteoporosis, occurs mainly in those persons older than 70 years of age. Causes of secondary osteoporosis may be endocrine (e.g. glucocorticoid excess, hyperparathyroidism, hypoganodism), drug induced (e.g. corticosteroid, heparin, tobaco) and miscellanous (e.g. chronic renal failure, hepatic disease and malabsorbtion syndrome osteoporosis). The phrase "at risk of developing a bone deficit"; as used herein, is intended to embrace mammals and humans having a higher than average predisposition towards developing a bone deficit. As an example, those susceptible towards osteoporosis include post-menopausal women, elderly males (e.g. those over the age of 65) and those being treated with drugs known to cause osteoporosis as a side-effect (e.g. steroid-induced osteoporosis). Certain factors are well known in the art which may be used to identify those at risk of developing a bone deficit due to bone remodelling disorders like osteoporosis. Important factors include low bone mass, family history, life style, estrogen or androgen deficiency and negative calcium balance. Postmenopausal women are particularly at risk of developing osteoporosis. Hereinafter, references to treatment of bone diseases are intended to include management and/or prophylaxis except where the context demands otherwise.

The methods described herein can also be used to enhance bone formation in conditions where a bone deficit is caused by factors other than bone remodeling disorders. Such bone deficits include fractures, bone trauma, conditions associated with post-traumatic bone surgery, post-prosthetic joint surgery, post plastic bone surgery, post dental surgery, bone chemotherapy, post dental surgery and bone radiotherapy. Fractures include all types of microscopic and macroscopic fractures. Examples of fractures includes avulsion fracture, comminuted fracture, transverse fracture, oblique fracture, spiral fracture, segmental fracture, displaced fracture, impacted fracture, greenstick fracture, torus fracture, fatigue fracture, intraarticular fracture (epiphyseal fracture), closed fracture (simple fracture), open fracture (compound fracture) and occult fracture.

As previously mentioned, a wide variety of bone diseases may be treated in accordance with the present invention, for example all those bone diseases connected with the bone-remodeling cycle. Examples of such diseases include all forms of osteoporosis, osteomalacia, rickets and Paget's disease. Osteoporosis, especially of the post-menopausal, male and steroid-induced types, is of particular note. In addition, the compounds can be used as antiresorption agents generally, as bone promotion agents and as anabolic bone agents. Such uses form another aspect of the present invention.

In many bone remodeling disorders, including osteoporosis, the bone deficit may be attributed to excess bone resorption by differentiated osteoclasts. The methods and compositions of the invention may be employed to inhibit osteoclast differentiation, thus inhibiting bone resorption.

If desired, the lanthanum compound may be administered simultaneously or sequentially with other active ingredients. These active ingredients may, for example include other medicaments or compositions capable of interacting with the bone remodeling cycle and/or which are of use in fracture repair. Such medicaments or compositions may, for example, be those of use in the treatment of osteoarthritis or osteoporosis.

Bone enhancing agents, known in the art to increase bone formation, bone density or bone mineralisation, or to prevent bone resorption may be used in the methods and pharmaceutical compositions of the invention. Suitable bone enhancing agents include natural or synthetic hormones, such as estrogens, androgens, calcitonin, prostaglandins and parathormone; growth factors, such as platelet-derived growth factor, insulin-like growth factor, transforming growth factor, epidermal growth factor, connective tissue growth factor and fibroblast growth factor; vitamins, particularly vitamin D; minerals, such as calcium, aluminum, strontium and fluoride; statin drugs, including pravastatin, fluvastatin, simvastatin, lovastatin and atorvastatin; agonsists or antagonsist of receptors on the surface of osteoblasts and osteoclasts, including parathormone receptors, estrogen receptors and prostaglandin receptors; bisphosphonate and anabolic bone agents.

V. Cell-Based Assay

High throughput screening is a recent technology that has been developed primarily within the pharmaceutical industry. It has emerged in response to the profusion of new biological targets and the need of the pharmaceutical industry to generate novel drugs rapidly in a changed commercial environment. Its development has been aided by the invention of new instrumentation, by new assay procedures, and by the availability of databases that allow huge numbers of data points to be managed effectively. High throughput screening combined with combinatorial chemistry, rational design, and automation of laboratory procedures has led to a significantly accelerated drug discovery process compared to the traditional one-compound-at-a-time approach. Screens may be performed manually, however robotic screening of the compound libraries is preferred as a time- and labor-saving device.

One critical aspect of the drug discovery process is the identification of potent lead compounds. A purely random selection of compounds for testing is unlikely to yield many active compounds against a given receptor. Typically, pharmaceutical companies screen 100,000 or more compounds per screen to identify approximately 100 potential lead compounds. On average, only one or two of these compounds actually produce lead compound series. Therefore, companies have been assaying larger and larger data sets in the search for useful compounds. Compound accessibility then becomes an issue: historical compound collections are limited in size and availability. In contrast, large combinatorial chemistry libraries can be synthesized on demand, but at significant technical difficulty and cost. As the library sizes expand, the difficulty becomes selecting the desired compounds from these very large combinatorial libraries. When literally hundreds of thousands of compounds are screened, it makes characterizing the candidate lead compounds an expensive and time-consuming process, particularly when many of the "hits" turn out to be false positives. The multi-step approach to the drug discovery process described here provides a solution to many of these problems.

A high throughput bioassay to identify modulators that are selective for NR2C- or NR2D-containing receptors is also disclosed. High throughput screening typically involves lead generation, followed by lead optimization. NR2C/D-containing recombinant NMDA receptors show little desensitization and are $Ca^{+2}$ permeable—two properties that renders them amenable to optical assays that measure agonist-induced $Ca^{+2}$ accumulation in mammalian cells using multi-well formats.

The assay involves using a cell line that expresses the NR1 subunit together with either NR2C or NR2D. These cell lines can be prepared by transfecting a cell line with an appropriate vector that includes the DNA encoding the NR2C or NR2D receptors. One suitable cell line is BHK-1 (Syrian hamster kidney BHK-21 is a subclone (clone 13) of the parental line established from the kidneys of five unsexed, one-day-old hamsters in 1961).

The NR2D receptor cDNA has also been cloned, for example, in 293T cells (Glover et al., "Interaction of the N-Methyl-D-Aspartic Acid Receptor NR2D Subunit with the c-Abl Tyrosine Kinase*," *J. Biol. Chem.*, Vol. 275, Issue 17, 12725-12729, Apr. 28, 2000). The cDNA for NR2D is also described in this reference.

An NR2D cDNA (clone designation pNR2D422) is also disclosed in Arvanian, et al., "Viral Delivery of NR2D Subunits Reduces Mg2+ Block of NMDA Receptor and Restores NT-3-Induced Potentiation of AMPA-Kainate Responses in Maturing Rat Motoneurons," *J Neurophysiol* 92: 2394-2404, 2004.

The cDNA for the NR2C is described, for example, in Lin, Y. J., Bovetto, S, Carver, J. M., and Giordano, T., "Cloning of the cDNA for the human NMDA receptor NR2C subunit and its expression in the central nervous system and periphery, *Molecular Brain Research,* 1996, vol. 43, no 1-2, pp. 57-64 (41 ref.). Lin et al. describe several overlapping cDNA clones containing 3995 nucleotides of the human 2C NMDA receptor subunit (NR2C) that were isolated from human hippocampal and cerebellar cDNA libraries. The predicted protein sequence is 1233 amino acids long. Lin et al. noted that readily detectable levels of NR2C are present in the hippocampus, amygdala, caudate nucleus, corpus callosum, subthalamic nuclei and thalamus, as well as the heart, skeletal muscle and pancreas, demonstrating a widespread expression pattern of the NR2C gene, both in the CNS and in the periphery.

In one embodiment, the high throughput bioassay uses commercially-available BHK-21 cell lines expressing NR1 under control of the Tet-On system (Clontech) (Hansen et al (2008), and which constitutively express either NR2C or NR2D. FIG. 4A illustrates vector design for the NR2D cell line. A similar strategy can be used for the NR2C cell line, except that the NR2C cDNA is used in place of NR2D cDNA.

Stable expression of NMDA receptor subunits is cytotoxic. To avoid this toxicity, the culture media can be supplemented with NMDA receptor antagonists, for example, DL-APV and 7Cl-kynurenate. Functional NR1 expression can be induced by doxycyclin before the assay.

Fura-2 $Ca^{+2}$ imaging of the functional response of the NR1/NR2D cell line can be used to produce a glutamate $EC_{50}$ value, which can be compared to that measured from two-electrode voltage-clamp assay. If these values are comparable, this suggests that the cell line faithfully reproduces NR1/NR2D properties.

A cell line, such as a BHK cell line which expresses a low affinity glutamate transporter system ($K_m$ ~40 μM) should help keep glutamate concentration low, and reduce cytotoxicity due to NMDA receptor over-activation (Scott & Pateman, 1978; Arathoon & Telling, 1981).

BHK cells can be preferred, because they adhere tightly to the culture plastic, allowing thorough washing of potentiators present during culture without losing cells from the bottom of the dish. However, BHK cells can extrude a low level of glutamate through the reversal of the transporter when glutamate is absent from the extracellular solution, such as during wash and dye loading. Because glutamate activates NR2D-containing receptors with submicromolar $EC_{50}$ (<500 nM), even tens of nanomolar concentrations of glutamate (plus trace glycine) extruded by BHK cells from time of washing through dye loading are sufficient to activate NR1/NR2D receptors, injure cells, and compromise subsequent assays. This toxic activation also creates a high baseline $Ca^{+2}$ signal, which compromises the signal to noise ratio.

To circumvent this problem, one can remove cells from the incubator, wash out all antagonists, and subsequently add a competitive glycine site antagonist, such as 7-Cl-kynurenate, during the dye loading protocol. Use of a relatively low affinity antagonist enhances cell health during dye loading and experimental setup by preventing continual NR1/NR2D receptor activation by low levels of glutamate extruded by BHK cells.

At the time of the assay, the competitive glycine site antagonist is easily displaced by addition of an excess of glycine (for example, around 1 mM) together with glutamate (around 100 μM). The presence of antagonist improves the reliability and the signal-to-noise ratio for the assay.

One can vary plating density, culture time, induction time, DMSO content, agonist concentration, $Ca^{+2}$ concentration, fluorescent dye loading conditions, recording duration, and other parameters to reduce well-to-well variability. Z' values are a standard measure of variability for multi-well assays, with values above 0.5 considered a good indication that an assay is suitable for single well screening of test compounds (Zhang et al. 1999).

$$Z'=1-3'(SD_{signal}+SD_{baseline})/A_{signal}-A_{baseline}$$

We have carried out the assay, as shown in Example 8, and the assay always yielded a favorable value for Z' (0.4-0.8). Real time $Ca^{+2}$ signals can be recorded in multi-well plates, for example, 96 well plates, using plate readers, for example, FlexStation II multi-mode plate readers.

The assay has been designed to identify modulators acting to alter agonist binding to NR2D-containing receptors by using supramaximal concentrations of glutamate and glycine.

The assay can be validated using commercially available libraries, such as the Lopac library (1200 compounds), which contain a number of known NMDA receptor antagonists.

Test compounds can be added to each well, together with agonist, to yield a final well concentration of around 10 μM test compound in 0.9% DMSO. Compounds that alter the response of any well, compared to on-plate control wells, beyond 2.5-fold of the standard deviation (calculated from all wells on the plate) and by more than 40% of the control response on a given plate, can be selected for secondary screening. This secondary screening can be performed, for example, using two-electrode voltage-clamp recordings from *Xenopus* oocytes expressing recombinant NR1/NR2D receptors.

In one embodiment, the library of candidate compounds is a focused library of candidate compounds, for lead optimization, based on the structure of high affinity leads identified in a first lead generation assay.

The library of candidate compounds can be a combinatorial library of, for example drug-like molecules or a focused small molecule library.

The invention also provides compounds, including small molecules and peptides, proteins, and genetic material, identified according to the methods described above, as well as methods of treating patients in need of a subtype specific NMDA modulator, which methods involve administering the modulator to a patient in need of treatment thereof.

Any method known in the art for selecting and synthesizing small molecule libraries for screening is contemplated for use in this invention. Small molecules to be screened are advantageously collected in the form of a combinatorial library. For example, libraries of drug-like small molecules, such as beta-turn mimetic libraries and the like, may be purchased from for example ChemDiv, Pharmacopia or Combichem or synthesized and are described in Tietze and Lieb, Curr. Opin. Chem. Biol. 2:363-371, 1998; Carrell et al., Chem Biol. 2:171-183, 1995; U.S. Pat. Nos. 5,880,972, 6,087,186 and 6,184,223, the disclosures of which are hereby incorporated by reference.

Any of these libraries known in the art are suitable for screening, as are random libraries or individual compounds. In general, hydrophilic compounds are preferred because they are more easily soluble, more easily synthesized, and more easily compounded. Compounds having an average molecular weight of about 500 often are most useful, however, compounds outside this range, or even far outside this range also may be used. Generally, compounds having c log P scores of about 5.0 are preferred, however the methods are useful with all types of compounds. Simple filters like Lipinski's "rule of five" have predictive value and may be used to improve the quality of leads discovered by this inventive strategy by using only those small molecules which are bioavailable. See Lipinski et al., Adv. Drug Delivery Rev. 23:3-25, 1997.

Combinatorial chemistry small molecule "libraries" can be screened against drug targets. The idea is that diversity of chemical structures increases the chances of finding the needle in the $10^{200}$ possible small organic molecule haystack. These collections provide an excellent source of novel, readily available leads. For example, ChemDiv uses more than 800 individual chemical cores, a unique Building Block Library, and proprietary chemistry in designing its Diversity Collections (small molecule libraries) to assemble 80,000-100,000 compounds a year. CombiLab lead library sets of 200-400 compounds also can be produced as a follow-up. In addition, ChemDiv's compounds are designed to ensure their similarity to drugs adjusted according to proprietary algorithms of "drug-likeness definitions" (group similarity and advanced neural net approaches), and a variety of intelligent instruments for ADME&T (Absorption, Distribution, Metabolism, Excretion and Toxicity) properties prediction, such as partition coefficient, solubility, dissociation coefficients, and acute toxicity.

Thus, focused synthesis of new small molecule libraries can provide a variety of compounds structurally related to the initial lead compound which may be screened to choose optimal structures. Preferably, a library of compounds is selected that are predicted to be "drug-like" based on properties such as pKa, log P, size, hydrogen bonding and polarity. The inventive multi-step approach which yields high affinity peptides in the first step, and small molecules in a subsequent step reduces the number of artificial hits by eliminating the lower affinity small molecules that would be selected and have to be assayed in a normal high throughput screening method. In addition, it focuses the search for molecules that can modulate the binding of a peptide the mimics the G protein rather than screening for binding to any site on the receptor. Other advantages of this technology are that it is simple to implement, amenable to many different classes of receptors, and capable of rapidly screening very large libraries of compounds.

Generally, it is convenient to test the libraries using a one well-one compound approach to identify compounds which compete with the peptide fusion protein or high affinity peptide for binding to the receptor. A single compound per well can be used, at about 1 µM each or at any convenient concentration depending on the affinity of the receptor for the compounds and the peptide against which they are being tested. Compounds may be pooled for testing, however this approach requires deconvolution. Compounds may be pooled in groups of about 2 to about 100 compounds per well, or more, or about 10 to about 50 compounds per well at about 10 nM each or at any convenient concentration depending on the affinity of the receptor for the compounds being tested. Several different concentrations may be used if desired.

Peptides desirably are screened using a pooled approach because of the layer members of peptides which are screened in the first instance. Peptides may be screened individually as well, but preferably are screened in pools of about $10^4$-$10^{12}$ peptides per well or about $10^8$-$10^{10}$ peptide per well.

Preferably, the most strongly binding and effective compounds are subjected to a subsequent lead optimization screening step.

Thorough evaluation of the selected compounds (either peptides or small molecules) for use as therapeutic agents may proceed according to any known method. Properties of the compounds, such as $pK_a$, log P, size, hydrogen bonding and polarity are useful information. They may be readily measured or calculated, for example from 2D connection tables, if not already known prior to identification by the inventive method as a useful compound. Association/dissociation rate constants may be determined by appropriate binding experiments. Parameters such as absorption and toxicity also may be measured, as well as in vivo confirmation of biological activity. The screen may be optimized for small molecules according to methods known in the art. Additionally, it is preferable to use a software system for presentation of data that allows fast analysis of positives.

Many databases and computer software programs are available for use in drug design. For example, see Ghoshal et al., Pol. J. Pharmacol. 48(4):359-377, 1996; Wendoloski et al., Pharmacol. Ther. 60(2):169-183, 1993; and Huang et al., J. Comput. Aided Mol. Des. 11:21-78, 1997. Databases can be used to store and manipulate data on the compounds obtained using the screen, and can compare the binding affinity against the NR2C and NR2D receptors, and/or other receptors, to determine the selectivity of the compounds for the desired receptor.

EXAMPLES

The following examples are provided to illustrate the present invention and are not intended to limit the scope thereof. Those skilled in the art will readily understand that known variations of the conditions and processes of the following preparative procedures can be used to manufacture the desired compounds. The materials required for the embodiments and the examples are known in the literature, readily commercially available, or can be made by known methods from the known starting materials by those skilled in the art.

Example 1: NMDA Receptor Activity of the Compounds of Formula A

FIG. 2A illustrates the subunit-selectivity with which the compounds of Formula A, including a specific compound herein referred to as DIQ-1180, acts on recombinant NMDA receptors. The structure of DIQ-1180 is shown below.

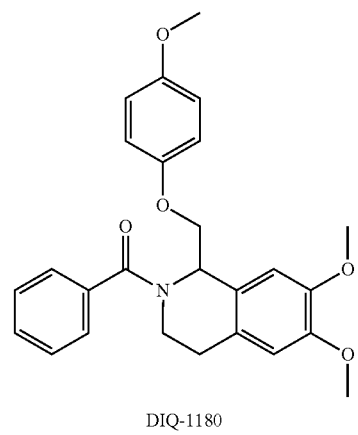

DIQ-1180

The $EC_{50}$ value for potentiation of NR2C-containing receptors was 11 µM (maximal potentiation 181%); the $EC_{50}$ value at NR2D-containing receptors was 13 µM 162%; several halogenated analogues are ~3-fold more potent with $EC_{50}$ values under 3 µM (not shown). The Hill slope at both receptors for all analogues was greater than 1, consistent with a cooperative effect of binding at two sites. Potentiation was reversible, repeatable, and did not lead to run down or run up of the response (data not shown). The potentiating actions of DIQ-1180 were voltage-independent (n=7) and pH-independent, suggesting that potentiation did not reflect relief of tonic proton inhibition (n=10-16), as has been proposed for spermine potentiation of NR2B-containing receptors (Traynelis et al 1995). Furthermore, at peak potentiation there is no shift in the $EC_{50}$ for activation of NR1/NR2D receptors by glutamate ($EC_{50}$ was 0.39 and 0.43 µM in the absence and presence of DIQ-1180; n=6,6) or glycine, which had an $EC_{50}$ of 0.20 µM both in the absence (n=5) and presence (n=8) of DIQ-1180.

These data suggest that potentiator binding is not allosterically coupled to agonist binding. Analysis of glutamate/glycine-activated unitary currents in an excised outside-out patch that contain at least two NR1/NR2D channels suggest that DIQ-1180 can increase the total open probability (nPo) from 0.083 to 0.207 (FIG. 3B). This reflected an increase to 178% of control in opening frequency, which was reversed by washout of compound DIQ-1180 (not shown). Our initial studies varying the compound structure confirm that there are strict requirements for the position and type of substituent on the isoquinoline backbone (see Table 3).

NR2C/D Expression in Hippocampal and Subthalamic Neurons

Figure 3:
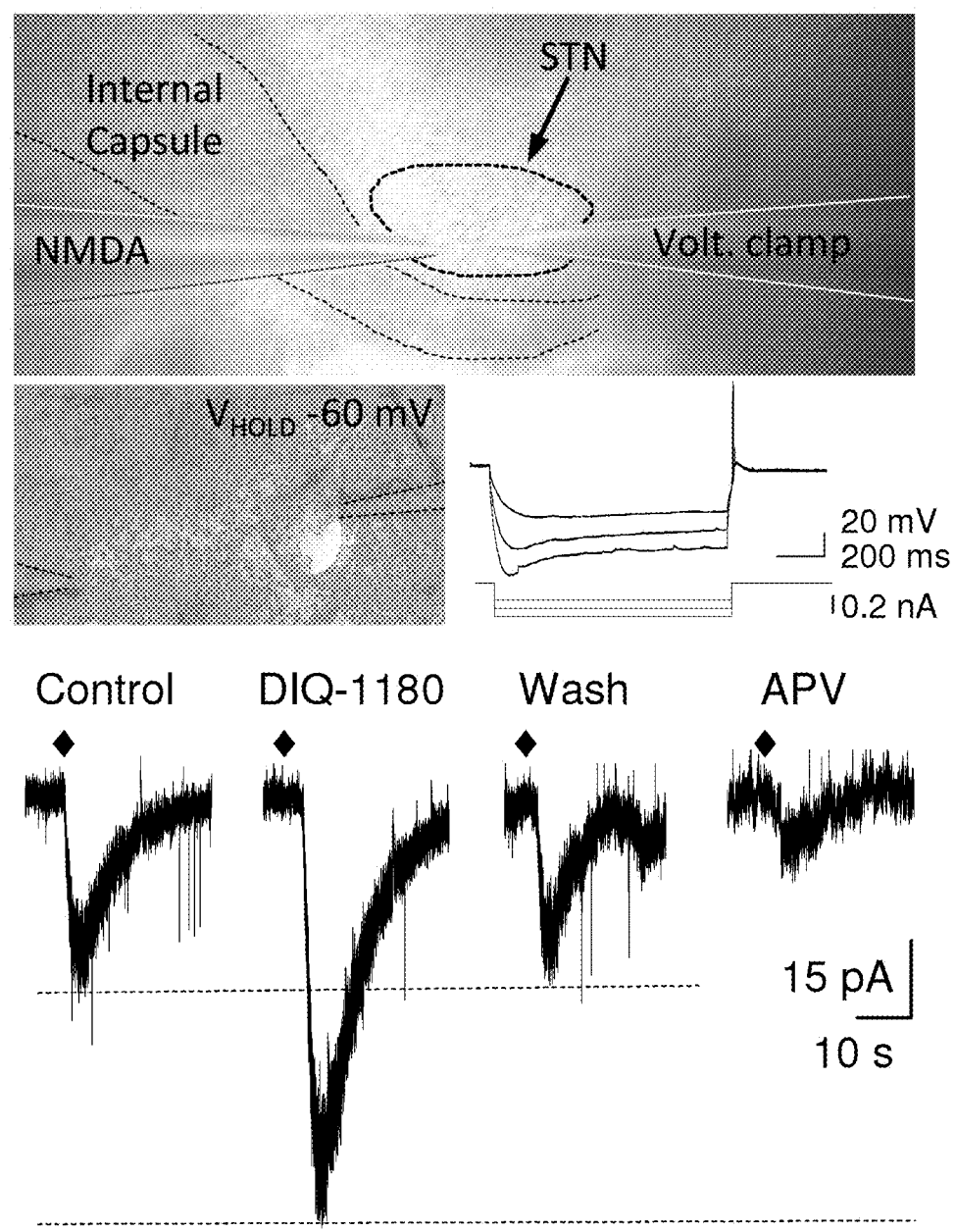
FIG. 3 is a photomicrograph of recording arrangement for the subthalamic nucleus. All neurons had an $I_H$ current, as expected for subthalamic neurons. Responses to pressure-applied NMDA/glycine (both 2 mM, 20 ms, 2 psi) in slices bathed in 0.2 mM $Mg^{2+}$, 0.5 µM TTX, 10 µM bicuculline, 10 µM CNQX were potentiated by 30 µM DIQ-1180, and blocked by 100 µM DL-APV.

We tested compound-1180 for activity at native NMDA receptor responses in neurons from basal ganglia slices. We focused on neurons that have been suggested to express NR2D. We performed patch clamp recording from slices of subthalamic nuclei in our lab. Preliminary data shows that DIQ-1180 (30 µM) potentiates the current response to pressure-applied NMDA (n=2; FIG. 3) in slices bathed in tetrodotoxin (1 µM) to eliminate synaptic activity.

These data are consistent with the idea derived from anatomical data suggesting that subthalamic neurons likely express NMDA receptors that contain functional NR2D subunit (Standaert et al 1994; Dunah et al 1998, 2003).

Data on additional potentiators is shown below in the following tables:

| # | Structure | 2A IC50 (µM) | 2B IC50 (µM) | 2C IC50 (µM) | Max | 2D IC50 (µM) | Max |
|---|---|---|---|---|---|---|---|
| 1180 | 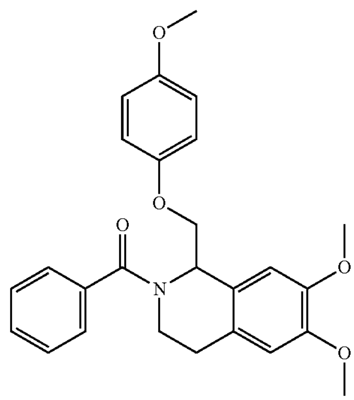 | 81% at 100 µM | 67% at 100 µM | 12 | 145 | 11 | 156 |
| 1369 | 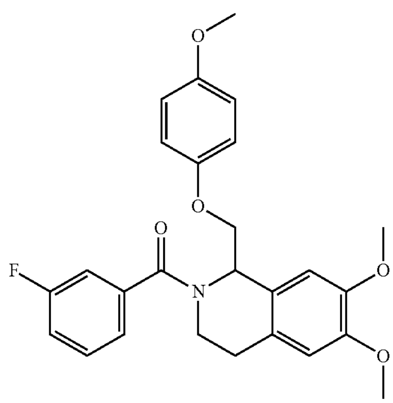 | 94% at 100 µM | 84% at 100 µM | 7 | 184 | 7 | 169 |
| 1390 | 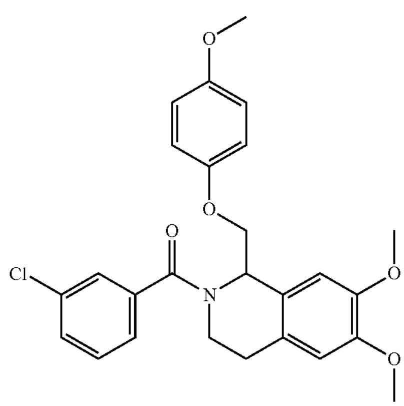 | 115% at 100 µM | 82% at 100 µM | 3 | 215 | 3 | 205 |

-continued
| | | 1180 P COMPOUNDS | | | | | |
|---|---|---|---|---|---|---|---|
| # | Structure | 2A IC50 (μM) | 2B IC50 (μM) | 2C IC50 (μM) | Max | 2D IC50 (μM) | Max |
| 1391 | 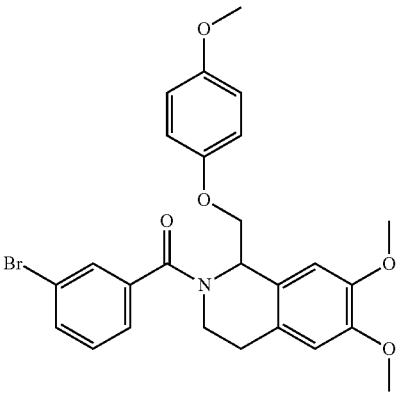 | 119% at 100 μM | 74% at 100 μM | 1 | 195 | 2 | 188 |
| 1426 | 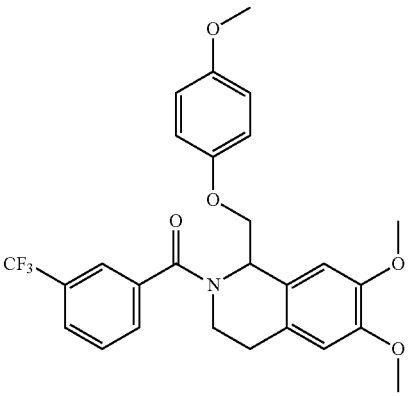 | 88% at 100 μM | 86% at 100 μM | 2 | 171 | 2 | 204 |
| 1425 | 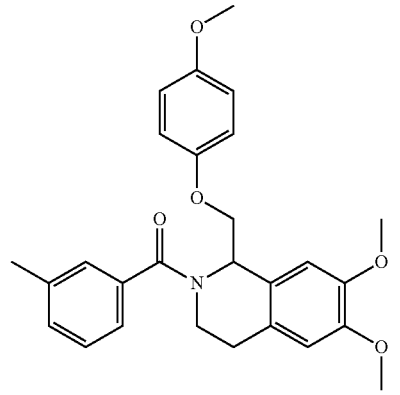 | 74% at 100 μM | 94% at 100 μM | 5 | 208 | 5 | 172 |

| 1180 P COMPOUNDS | | | | | | |
|---|---|---|---|---|---|---|
| | | 2A IC50 (μM) | 2B IC50 (μM) | 2C IC50 (μM) | Max | 2D IC50 (μM) | Max |
| # | Structure | | | | | | |
| 1392 | | 104% at 100 μM | 59% at 100 μM | 6 | 181 | 12 | 179 |
| 1368 | | 105% at 100 μM | 78% at 100 μM | 4 | 135 | 5 | 114 |
| 1409 | | | | 76% at 100 μM | | 82% at 100 μM | |

| 1180 P COMPOUNDS | | | | | | | |
|---|---|---|---|---|---|---|---|
| # | Structure | 2A IC50 (μM) | 2B IC50 (μM) | 2C IC50 (μM) | Max | 2D IC50 (μM) | Max |
| 1263 | 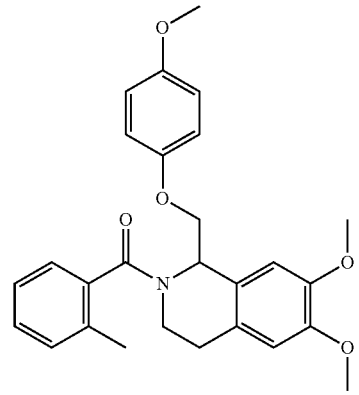 | | | 105% at 100 μM | | 97% at 100 μM | |
| 1371 | 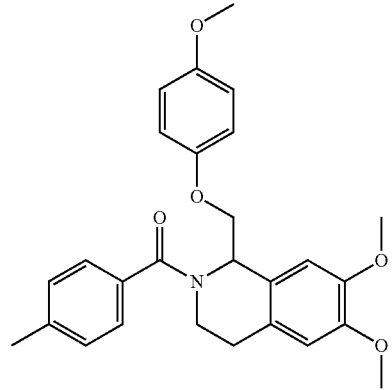 | 73% at 100 μM | 70% at 100 μM | 89% at 100 μM | | 100% at 100 μM | |
| 1408 | 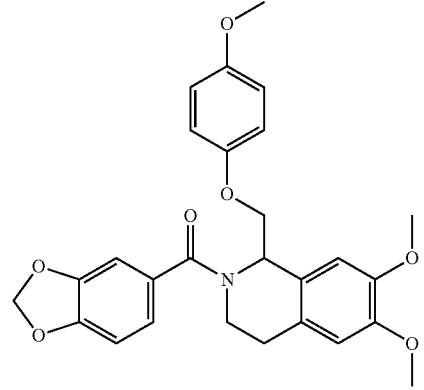 | | | 95% at 100 μM | | 88% at 100 μM | |

-continued

| | | 1180 P COMPOUNDS | | | | | |
|---|---|---|---|---|---|---|---|
| # | Structure | 2A IC50 (μM) | 2B IC50 (μM) | 2C IC50 (μM) | Max | 2D IC50 (μM) | Max |
| 1364 | | | 75% at 100 μM | 98% at 100 μM | | 93% at 100 μM | |
| 1393 | | 120% at 100 μM | 80% at 100 μM | 96% at 100 μM | | 94% at 100 μM | |
| 1370 | | 77% at 100 μM | 78% at 100 μM | 83% at 100 μM | | 95% at 100 μM | |

1180 P COMPOUNDS

| # | Structure | 2A IC50 (µM) | 2B IC50 (µM) | 2C IC50 (µM) | Max | 2D IC50 (µM) | Max |
|---|---|---|---|---|---|---|---|
| 1510 | 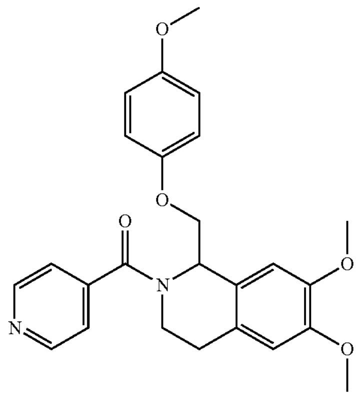 | | 87% at 100 µM | 90% at 100 µM | | 87% at 100 µM | |
| 1484 | 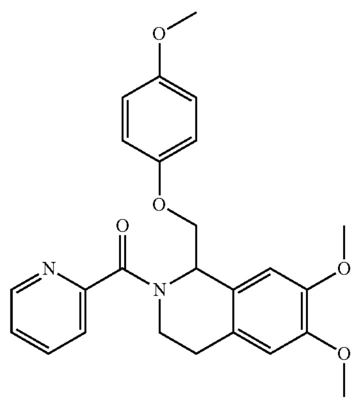 | 100% at 100 µM | 80% at 100 µM | 76% at 100 µM | | 84% at 100 µM | |
| 1485 | 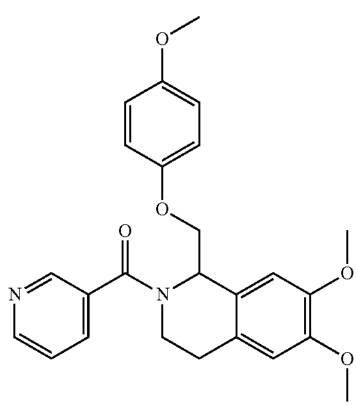 | 75% at 100 µM | 85% at 100 µM | 82% at 100 µM | | 74% at 100 µM | |

| | | 1180 P COMPOUNDS | | | | | |
|---|---|---|---|---|---|---|---|
| # | Structure | 2A IC50 (μM) | 2B IC50 (μM) | 2C IC50 (μM) | Max | 2D IC50 (μM) | Max |
| 1486 | | 78% at 100 μM | 88% at 100 μM | 9 | 131 | 6 | 112 |
| 1487 | | 89% at 100 μM | 71% at 100 μM | 69% at 100 μM | | 79% at 100 μM | |
| 1511 | | | | 99% at 10 μM | | 96% at 10 μM | |

-continued

| | | 1180 P COMPOUNDS | | | | | |
|---|---|---|---|---|---|---|---|
| # | Structure | 2A IC50 (μM) | 2B IC50 (μM) | 2C IC50 (μM) | Max | 2D IC50 (μM) | Max |
| 1367 | | | | 104% at 100 μM | | 93% at 100 μM | |
| 1444 | | 91% at 100 μM | 68% at 100 μM | 102% at 100 μM | | 111% at 100 μM | |
| 1410 | | | | 94% at 100 μM | | 89% at 100 μM | |

| | | 1180 P COMPOUNDS | | | | |
|---|---|---|---|---|---|---|
| # | Structure | 2A IC50 (μM) | 2B IC50 (μM) | 2C IC50 (μM) | Max | 2D IC50 (μM) | Max |
| 1366 | | 98% at 100 μM | 97% at 100 μM | 3 | 121 | 108% at 100 μM | |
| 1394 | | 101% at 100 μM | 61% at 100 μM | 71% at 100 μM | | 68% at 100 μM | |
| 1438 | | 114% at 100 μM | 85% at 100 μM | 77% at 100 μM | | 87% at 100 μM | |

1180 P COMPOUNDS
| # | Structure | 2A IC50 (μM) | 2B IC50 (μM) | 2C IC50 (μM) | Max | 2D IC50 (μM) | Max |
|---|---|---|---|---|---|---|---|
| 1439 | 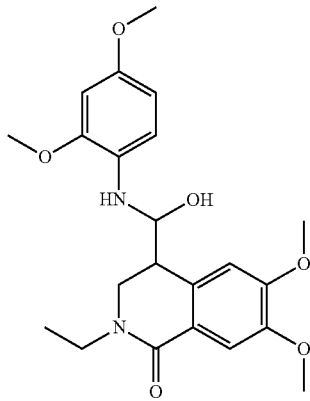 | | 99% at 100 μM | 96% at 100 μM | 84% at 100 μM | | 89% at 100 μM | |
| 1440 | 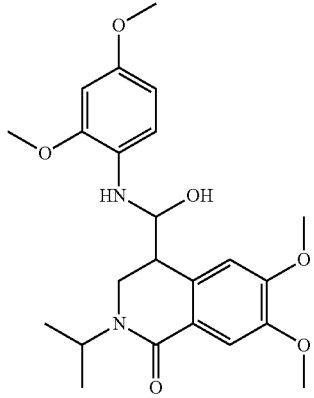 | | 123% at 100 μM | 90% at 100 μM | 71% at 100 μM | | 82% at 100 μM | |
| 1407 | 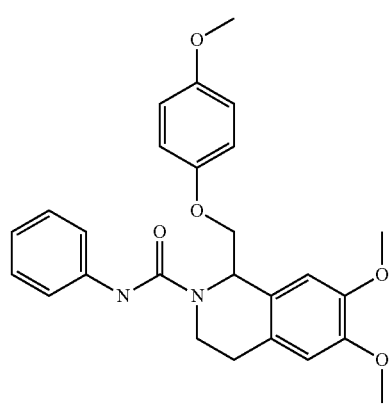 | | | 86% at 100 μM | | | 88% at 100 μM | |

1180 P COMPOUNDS

| # | Structure | 2A IC50 (μM) | 2B IC50 (μM) | 2C IC50 (μM) | Max | 2D IC50 (μM) | Max |
|---|---|---|---|---|---|---|---|
| 1411 | 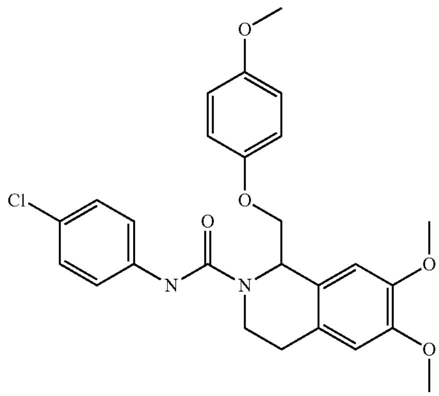 | | | 84% at 100 μM | | 66% at 100 μM | |
| 1412 | 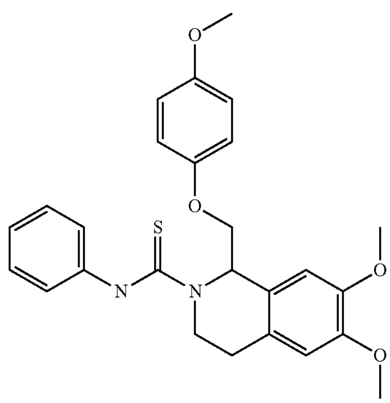 | | | 93% at 100 μM | | 79% at 100 μM | |
| 1413 | 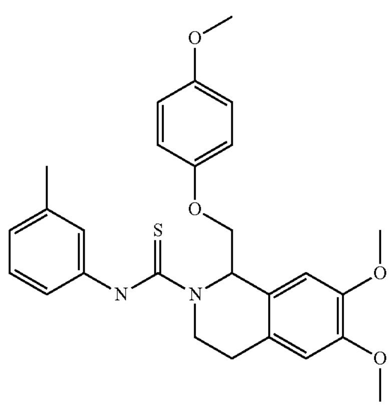 [SMILES: COc1ccc(OCC2c3cc(OC)c(OC)cc3CCN2C(=S)Nc2cccc(C)c2)cc1] | | | 102% at 100 μM | | 74% at 100 μM | |

-continued

| | | 1180 P COMPOUNDS | | | | | |
|---|---|---|---|---|---|---|---|
| # | Structure | 2A IC50 (μM) | 2B IC50 (μM) | 2C IC50 (μM) | Max | 2D IC50 (μM) | Max |
| 1414 | | | | | 99% at 100 μM | | 93% at 100 μM |
| 1415 | | | | | 99% at 100 μM | | 87% at 100 μM |
| 1416 | | | | | 96% at 100 μM | | 87% at 100 μM |

No compounds potentiated homomeric GluR1 AMPA receptor responses. When no inhibition or potentiation is given, the percent effect at the maximum tested concentration is given.

In the table above, potency is expressed as fitted $EC_{50}$ value to average composite concentration-effect data constructed from current responses recorded under two electrode voltage clamp from *Xenopus laevis* oocytes expressing either NR1/NR2A, B, C, or D, GluR1, or GluR6. No effect means less than 20% change in response amplitude at 30 μM of drug.
| # | Structure | 2A IC50 (μM) | 2B IC50 (μM) | 2C IC50 (μM) | Max | 2D IC50 (μM) | Max |
|---|---|---|---|---|---|---|---|
| 1180-1 | 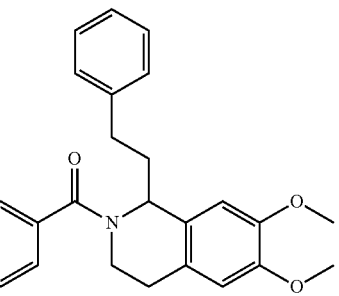 | 110% at 100 μM | | 96% at 30 μM | | 90% at 30 μM | |
| 1180-2 | 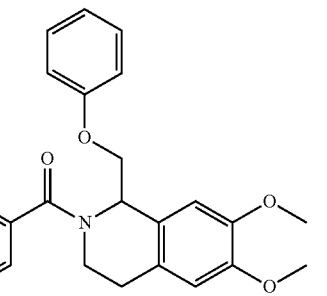 | 100% at 100 μM | 101% at 100 μM | 77% at 100 μM | | 81% at 100 μM | |
| 1180-3 | 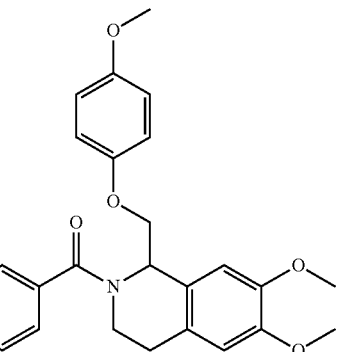 | 126% at 100 μM | 78% at 100 μM | 81% at 100 μM | | 79% at 100 μM | |
| 1180-4 | 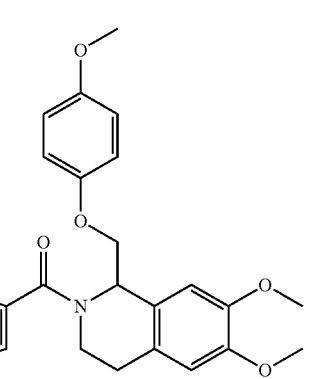 | 105% at 100 μM | 69% at 100 μM | 100% at 100 μM | | 89% at 100 μM | |
1180 S Compounds -continued

| | | 1180 S Compounds | | | | | |
|---|---|---|---|---|---|---|---|
| # | Structure | 2A IC50 (μM) | 2B IC50 (μM) | 2C IC50 (μM) | Max | 2D IC50 (μM) | Max |
| 1180-5 | | 98% at 100 μM | 86% at 100 μM | 83% at 100 μM | | 81% at 100 μM | |
| 1180-6 | | 93% at 100 μM | 97% at 100 μM | 94% at 100 μM | | 88% at 100 μM | |
| 1180-7 | | 94% at 100 μM | 92% at 100 μM | 75% at 100 μM | | 75% at 100 μM | |
| 1180-8 | | 99% at 100 μM | 89% at 100 μM | 73% at 100 μM | | 84% at 100 μM | |

-continued

| | 1180 S Compounds | | | | | | |
|---|---|---|---|---|---|---|---|
| # | Structure | 2A IC50 (μM) | 2B IC50 (μM) | 2C IC50 (μM) | Max | 2D IC50 (μM) | Max |
| 1180-9 | | 87% at 100 μM | 97% at 100 μM | 109% at 100 μM | | 99% at 100 μM | |
| 1180-10 | | | | 3 | 134 | 8 | 172 |
| 1180-11 | | 84% at 30 μM | 82% at 30 μM | 31 | 431 | 111% at 30 μM | |
| 1180-12 | | 97% at 30 μM | 90% at 30 μM | 2 | 133 | 109% at 30 μM | |

-continued
| | | 1180 S Compounds | | | | | | |
|---|---|---|---|---|---|---|---|---|
| # | Structure | | 2A IC50 (μM) | 2B IC50 (μM) | 2C IC50 (μM) | Max | 2D IC50 (μM) | Max |
| 1180-13 | 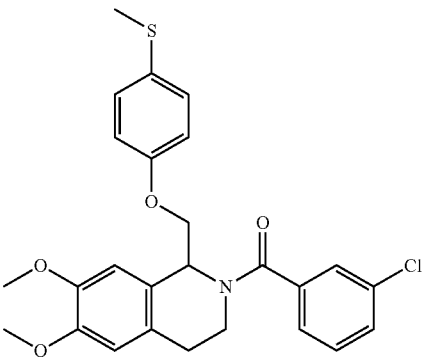 [SMILES: COc1cc2c(cc1OC)C(COc1ccc(SC)cc1)N(C(=O)c1cccc(Cl)c1)CC2] | | 112% at 100 μM | 67% at 100 μM | 97% at 100 μM | | 105% at 100 μM | |
| 1180-14 | 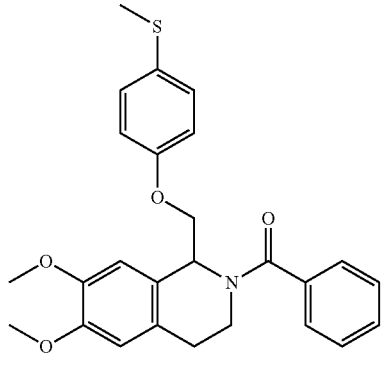 [SMILES: COc1cc2c(cc1OC)C(COc1ccc(SC)cc1)N(C(=O)c1ccccc1)CC2] | | 115% at 100 μM | 128% at 100 μM | 93% at 100 μM | | 103% at 100 μM | |
| 1180-15 | 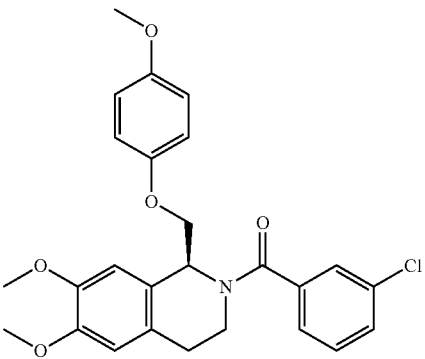 [SMILES: COc1ccc(OC[C@@H]2c3cc(OC)c(OC)cc3CCN2C(=O)c2cccc(Cl)c2)cc1] | | 128% at 30 μM | | 2.4 | 330 | 4 | 364 |
| 1180-16 | 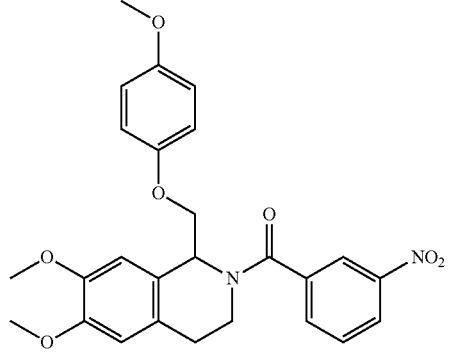 [SMILES: COc1ccc(OCC2c3cc(OC)c(OC)cc3CCN2C(=O)c2cccc([N+](=O)[O-])c2)cc1] | | 50% at 100 μM | 123% at 100 μM | 13 | 267 | 16 | 297 |

1180 S Compounds

| # | Structure | 2A IC50 (μM) | 2B IC50 (μM) | 2C IC50 (μM) | Max | 2D IC50 (μM) | Max |
|---|---|---|---|---|---|---|---|
| 1180-17 | 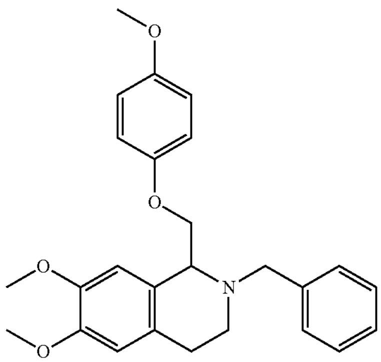 [SMILES: COc1ccc(OCC2c3cc(OC)c(OC)cc3CCN2Cc2ccccc2)cc1] | 50% at 20 uM | 90% at 100 μM | 95% at 100 μM | | 83% at 100 μM | |
| 1180-18 | 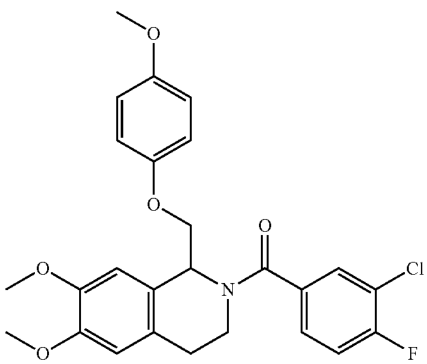 | 136% at 100 μM | 95% at 100 μM | 6 | 226 | 7 | 206 |
| 1180-19 | 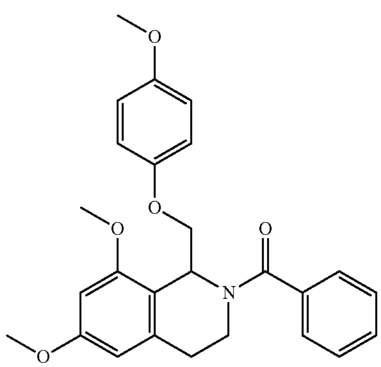 [SMILES: COc1ccc(OCC2c3c(cc(OC)cc3OC)CCN2C(=O)c2ccccc2)cc1] | 63% at 100 μM | 100% at 100 μM | 10 | 160 | 9 | 150 |
| 1180-20 | 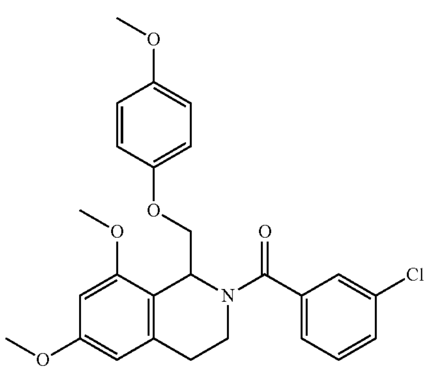 [SMILES: COc1ccc(OCC2c3c(cc(OC)cc3OC)CCN2C(=O)c2cccc(Cl)c2)cc1] | 92% at 100 μM | 86% at 100 μM | 11 | 253 | 18 | 271 |

1180 S Compounds

| # | Structure | 2A IC50 (μM) | 2B IC50 (μM) | 2C IC50 (μM) | Max | 2D IC50 (μM) | Max |
|---|---|---|---|---|---|---|---|
| 1180-21 | 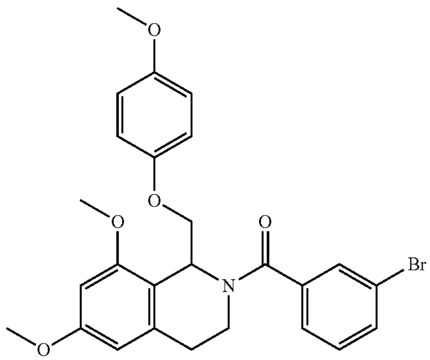 [SMILES: COc1ccc(OCC2c3c(cc(OC)cc3OC)CCN2C(=O)c2cccc(Br)c2)cc1] | 92% at 100 μM | 72% at 100 μM | 7 | 265 | 7 | 230 |
| 1180-22 | 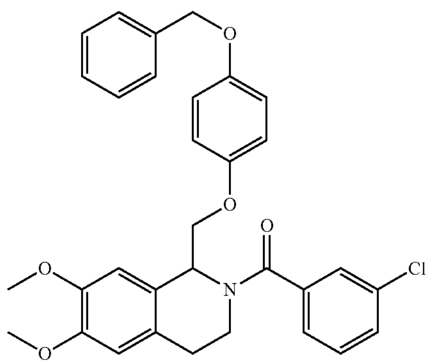 [SMILES: COc1cc2c(cc1OC)C(COc1ccc(OCc3ccccc3)cc1)N(C(=O)c1cccc(Cl)c1)CC2] | 95% at 100 μM | 50% at 20 μM | 79% at 100 μM | | 58% at 100 μM | |
| 1180-23 | 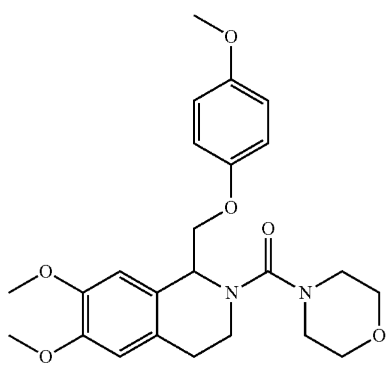 [SMILES: COc1ccc(OCC2c3cc(OC)c(OC)cc3CCN2C(=O)N2CCOCC2)cc1] | 140% at 100 μM | 61% at 100 μM | 87% at 100 μM | | 78% at 100 μM | |
| 1180-24 | 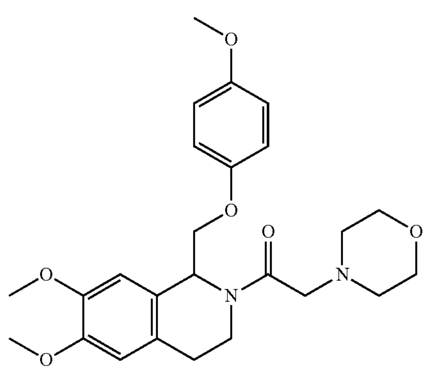 [SMILES: COc1ccc(OCC2c3cc(OC)c(OC)cc3CCN2C(=O)CN2CCOCC2)cc1] | 100% at 100 μM | 96% at 100 μM | 79% at 100 μM | | 83% at 10 0μM | |

-continued
| | | 1180 S Compounds | | | | | |
|---|---|---|---|---|---|---|---|
| # | Structure | 2A IC50 (μM) | 2B IC50 (μM) | 2C IC50 (μM) | Max | 2D IC50 (μM) | Max |
| 1180-25 | 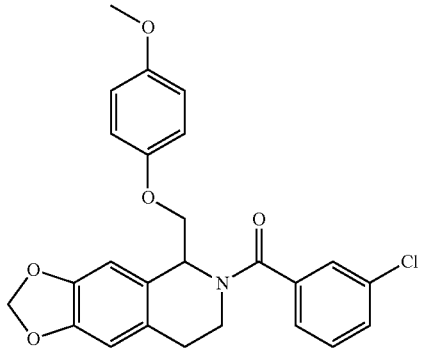 [SMILES: COc1ccc(OCC2c3cc4c(cc3CCN2C(=O)c2cccc(Cl)c2)OCO4)cc1] | 96% at 100 μM | 76% at 100 μM | 12 | 188 | 7 | 162 |
| 1180-26 | 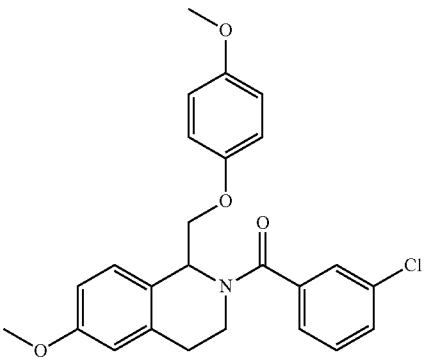 [SMILES: COc1ccc(OCC2c3ccc(OC)cc3CCN2C(=O)c2cccc(Cl)c2)cc1] | 93% at 100 μM | 75% at 100 μM | 0.8 | 196 | 1.0 | 185 |
| 1180-27 | 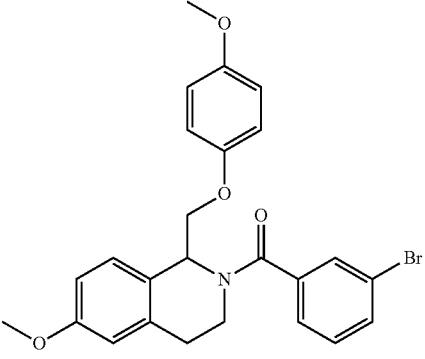 [SMILES: COc1ccc(OCC2c3ccc(OC)cc3CCN2C(=O)c2cccc(Br)c2)cc1] | 107% at 100 μM | 77% at 100 μM | 1 | 192 | 1.0 | 168 |
| 1180-28 | 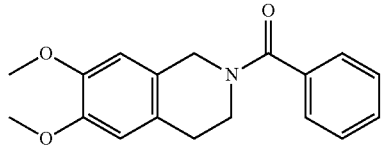 [SMILES: COc1cc2c(cc1OC)CN(C(=O)c1ccccc1)CC2] | 71% at 100 μM | 95% at 100 μM | 78% at 100 μM | | 80% at 100 μM | |
| 1180-29 | 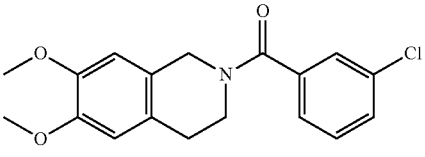 [SMILES: COc1cc2c(cc1OC)CN(C(=O)c1cccc(Cl)c1)CC2] | 75% at 100 μM | 58% at 100 μM | 82% at 100 μM | | | |

1180 S Compounds

| # | Structure | 2A IC50 (μM) | 2B IC50 (μM) | 2C IC50 (μM) | Max | 2D IC50 (μM) | Max |
|---|---|---|---|---|---|---|---|
| 1180-30 | 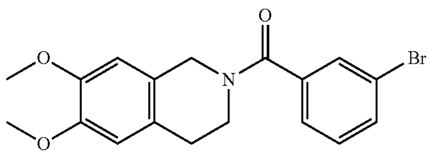 [SMILES: COc1cc2c(cc1OC)CN(C(=O)c1cccc(Br)c1)CC2] | | | | | | |
| 1180-31 | 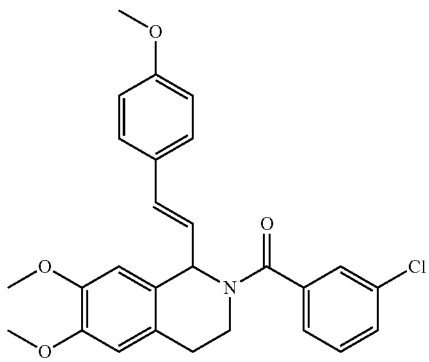 [SMILES: COc1ccc(/C=C/C2c3cc(OC)c(OC)cc3CCN2C(=O)c2cccc(Cl)c2)cc1] | 95% at 30 μM | 82% at 30 μM | 1.2 | 190 | 1.5 | 172 |
| 1180-32 | 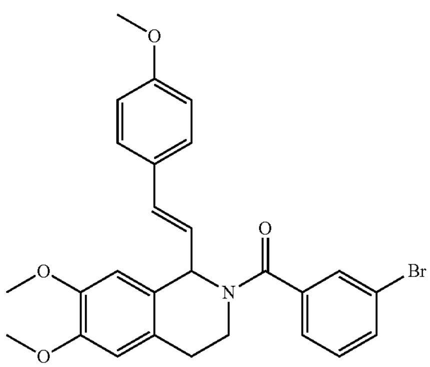 [SMILES: COc1ccc(/C=C/C2c3cc(OC)c(OC)cc3CCN2C(=O)c2cccc(Br)c2)cc1] | | | | | | |
| 1180-33 | 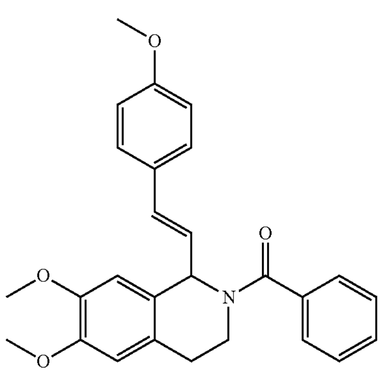 [SMILES: COc1ccc(/C=C/C2c3cc(OC)c(OC)cc3CCN2C(=O)c2ccccc2)cc1] | | | | | | |

1180 S Compounds

| # | Structure | 2A IC50 (μM) | 2B IC50 (μM) | 2C IC50 (μM) | Max | 2D IC50 (μM) | Max |
|---|---|---|---|---|---|---|---|
| 1180-34 | 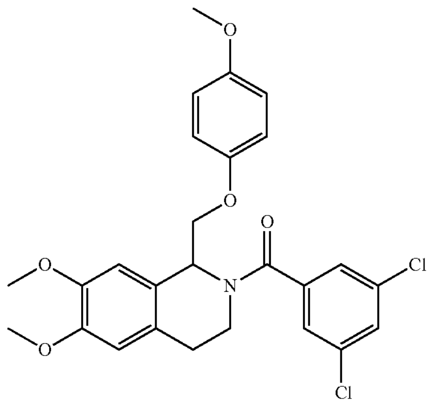 [SMILES: COc1ccc(OCC2c3cc(OC)c(OC)cc3CCN2C(=O)c2cc(Cl)cc(Cl)c2)cc1] | | | | | | |
| 1180-35 | 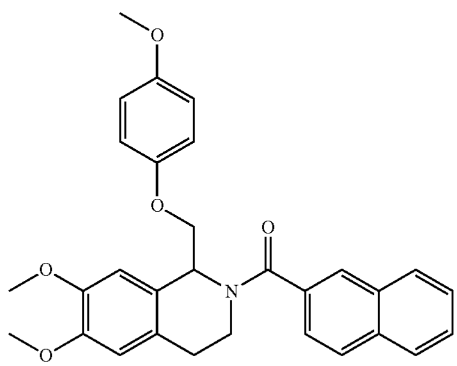 [SMILES: COc1ccc(OCC2c3cc(OC)c(OC)cc3CCN2C(=O)c2ccc3ccccc3c2)cc1] | | | | | | |

No compounds potentiated homomeric GluR1 AMPA receptor responses. When no inhibition or potentiation is given, the percent effect at the maximum tested concentration is given.

1357 S Compounds

| # | Structure | 2A IC50 (μM) | 2B IC50 (μM) | Max | 2C IC50 (μM) | Max | 2D IC50 (μM) | Max |
|---|---|---|---|---|---|---|---|---|
| 1357 | 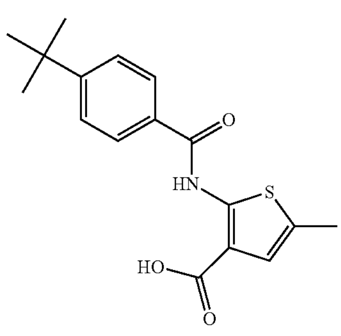 [SMILES: Cc1cc(C(=O)O)c(NC(=O)c2ccc(C(C)(C)C)cc2)s1] | 102% at 100 μM | 102% at 100 μM | | 175 | 388 | 120 | 326 |

-continued

| | | 1357 S Compounds | | | | | | |
|---|---|---|---|---|---|---|---|---|
| # | Structure | 2A IC50 (μM) | 2B IC50 (μM) | Max | 2C IC50 (μM) | Max | 2D IC50 (μM) | Max |
| 1418 | | 99% at 100 μM | 115% at 100 μM | | 33 | 187 | 35 | 195 |
| 1421 | | 106% at 100 μM | 100% at 100 μM | | 41 | 159 | 35 | 152 |
| 1399 | | 100% at 100 μM | 108% at 100 μM | | 77 | 301 | 26 | 261 |
| 1417 | | 87% at 100 μM | 102% at 100 μM | | 20 | 202 | 16 | 205 |

| # | Structure | 2A IC50 (μM) | 2B IC50 (μM) | Max | 2C IC50 (μM) | Max | 2D IC50 (μM) | Max |
|---|---|---|---|---|---|---|---|---|
| 1482 | 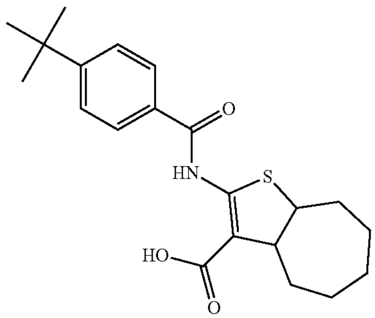 [SMILES: CC(C)(C)c1ccc(C(=O)NC2=C(C(=O)O)C3CCCCCC3S2)cc1] | 97% at 100 μM | 116% at 100 μM | | 19 | 127 | 16 | 170 |
| 1481 | 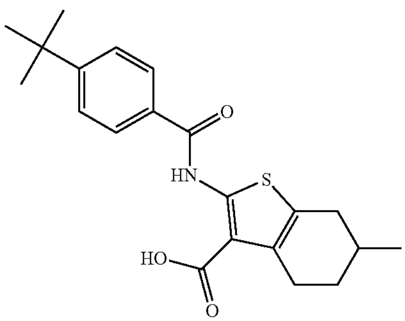 [SMILES: CC1CCc2c(sc(NC(=O)c3ccc(C(C)(C)C)cc3)c2C(=O)O)C1] | 113% at 100 μM | 119% at 100 μM | | 97% at 100 μM | | 21 | 124 |
| 1406 | 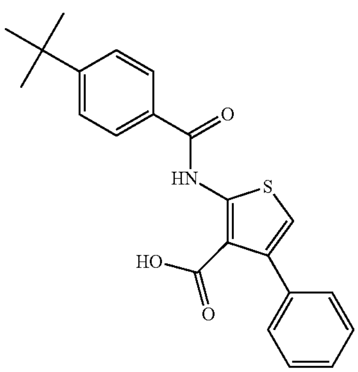 [SMILES: CC(C)(C)c1ccc(C(=O)Nc2scc(-c3ccccc3)c2C(=O)O)cc1] | 75% at 100 μM | 37 | 145 | 45 | 341 | 44 | 351 |
| 1423 | 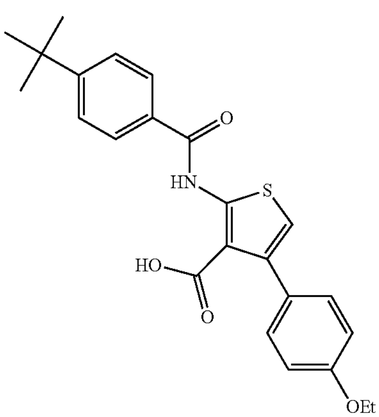 [SMILES: CCOc1ccc(-c2csc(NC(=O)c3ccc(C(C)(C)C)cc3)c2C(=O)O)cc1] | 121% at 100 μM | 18 | 224 | 26 | 323 | 25 | 370 |

1357 S Compounds

| # | Structure | 2A IC50 (μM) | 2B IC50 (μM) | Max | 2C IC50 (μM) | Max | 2D IC50 (μM) | Max |
|---|---|---|---|---|---|---|---|---|
| 1424 | | 123% at 100 μM | 19 | 225 | 42 | 434 | 43 | 475 |
| 1434 | | 121% at 100 μM | 11 | 199 | 16 | 224 | 18 | 273 |
| 1435 | | 107% at 100 μM | 98% at 100 μM | | 103% at 100 μM | | 103% at 100 μM | |

-continued

| | | 1357 S Compounds | | | | | | |
|---|---|---|---|---|---|---|---|---|
| # | Structure | 2A IC50 (μM) | 2B IC50 (μM) | Max | 2C IC50 (μM) | Max | 2D IC50 (μM) | Max |
| 1428 | | 105% at 100 μM | 70% at 100 μM | | 80% at 100 μM | | 72% at 100 μM | |
| 1395 | | 92% at 100 μM | 94% at 100 μM | | 95% at 100 μM | | 77% at 100 μM | |
| 1420 | | 118% at 100 μM | 97% at 100 μM | | 94% at 100 μM | | 75% at 100 μM | |
| 1489 | | 95% at 100 μM | 78% at 100 μM | | 83% at 100 μM | | 76% at 100 μM | |

-continued

| | | 1357 S Compounds | | | | | | |
|---|---|---|---|---|---|---|---|---|
| | | 2A | 2B | | 2C | | 2D | |
| # | Structure | IC50 (μM) | IC50 (μM) | Max | IC50 (μM) | Max | IC50 (μM) | Max |
| 1488 | | 98% at 100 μM | 83% at 100 μM | | 82% at 100 μM | | 80% at 100 μM | |
| 1404 | | 86% at 100 μM | 68% at 100 μM | | 99% at 100 μM | | 77% at 100 μM | |
| 1419 | | 93% at 100 μM | 91% at 100 μM | | 97% at 100 μM | | 90% at 100 μM | |
| 1396 | | 96% at 100 μM | 97% at 100 μM | | 95% at 100 μM | | 81% at 100 μM | |

-continued

1357 S Compounds

| # | Structure | 2A IC50 (μM) | 2B IC50 (μM) | Max | 2C IC50 (μM) | Max | 2D IC50 (μM) | Max |
|---|---|---|---|---|---|---|---|---|
| 1441 | 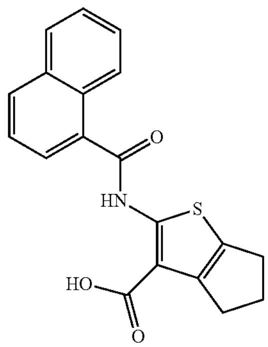 [SMILES: O=C(O)c1c(NC(=O)c2cccc3ccccc23)sc2c1CCC2] | 81% at 100 μM | 43 | 0 | 78% at 100 μM | | 86% at 100 μM | |
| 1400 | 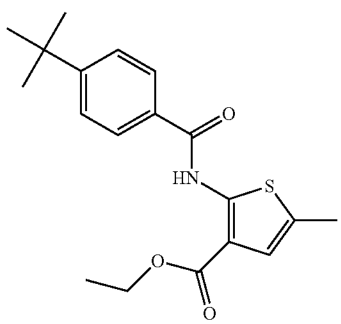 [SMILES: CCOC(=O)c1cc(C)sc1NC(=O)c1ccc(C(C)(C)C)cc1] | 80% at 100 μM | 89% at 100 μM | | 96% at 100 μM | | 86% at 100 μM | |
| 1433 | 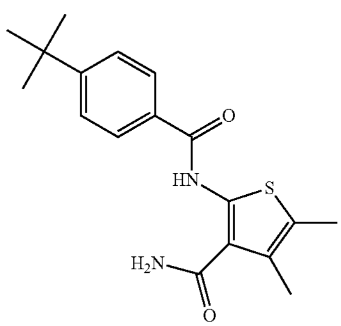 [SMILES: Cc1sc(NC(=O)c2ccc(C(C)(C)C)cc2)c(C(N)=O)c1C] | 97% at 100 μM | 98% at 100 μM | | 51 | 134 | 34 | 150 |
| 1398 | 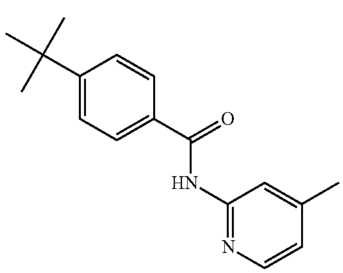 [SMILES: Cc1ccnc(NC(=O)c2ccc(C(C)(C)C)cc2)c1] | 89% at 100 μM | 102% at 100 μM | | 87% at 100 μM | | 76% at 100 μM | |

1357 S Compounds

| # | Structure | 2A IC50 (μM) | 2B IC50 (μM) | Max | 2C IC50 (μM) | Max | 2D IC50 (μM) | Max |
|---|---|---|---|---|---|---|---|---|
| 1401 | 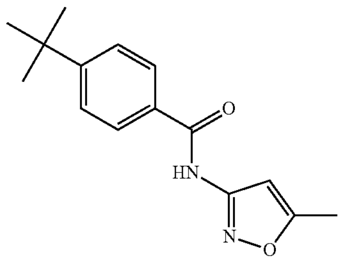 [SMILES: Cc1cc(NC(=O)c2ccc(C(C)(C)C)cc2)no1] | 105% at 100 μM | 87% at 100 μM | | 97% at 100 μM | | 86% at 100 μM | |
| 1479 | 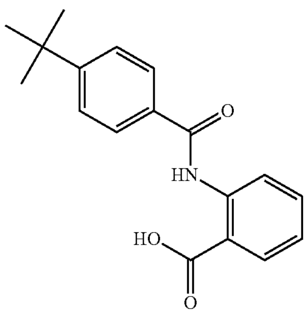 [SMILES: CC(C)(C)c1ccc(C(=O)Nc2ccccc2C(=O)O)cc1] | 94% at 100 μM | 97% at 100 μM | | 102% at 100 μM | | 113% at 100 μM | |
| 1480 | 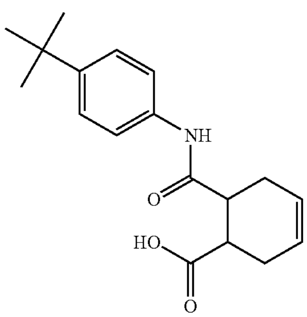 [SMILES: CC(C)(C)c1ccc(NC(=O)C2CC=CCC2C(=O)O)cc1] | 92% at 100 μM | 83% at 100 μM | | 86% at 100 μM | | 85% at 100 μM | |

No compounds potentiated homomeric GluR1 AMPA receptor responses. When no inhibition or potentiation is given, the percent effect at the maximum tested concentration is given.

1357 P Compounds and 1343 and 1568 Compounds

| # | Structure | 2A IC50 (μM) | 2B IC50 (μM) | Max | 2C IC50 (μM) | Max | 2D IC50 (μM) | Max |
|---|---|---|---|---|---|---|---|---|
| 1343 | 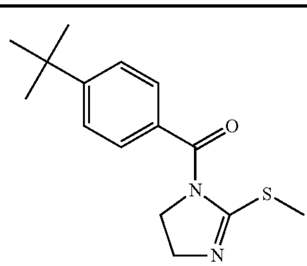 | 115% at 100 μM | 138 | 0 | 139 | 303 | 210 | 480 |

-continued

| # | Structure | 2A IC50 (μM) | 2B IC50 (μM) | Max | 2C IC50 (μM) | Max | 2D IC50 (μM) | Max |
|---|---|---|---|---|---|---|---|---|
| 1344 | 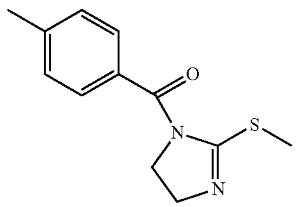 | 78% at 100 μM | 174 | 0 | 88% at 100 μM | | 97% at 100 μM | |
| 1397 | 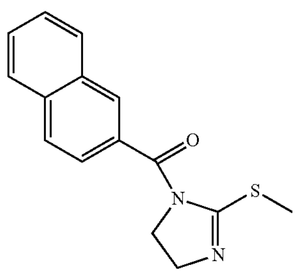 [SMILES: CSC1=NCCN1C(=O)c1ccc2ccccc2c1] | | | | 98% at 100 μM | | 87% at 100 μM | |
| 1402 | 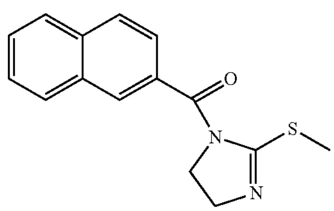 [SMILES: CSC1=NCCN1C(=O)c1ccc2ccccc2c1] | 104% at 100 μM | 80% at 100 μM | | 103% at 100 μM | | 93% at 100 μM | |
| 1403 | 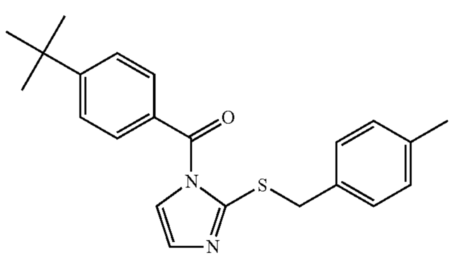 [SMILES: Cc1ccc(CSc2nccn2C(=O)c2ccc(C(C)(C)C)cc2)cc1] | 88% at 100 μM | 94% at 100 μM | | 104% at 100 μM | | 86% at 100 μM | |
| 1563 | 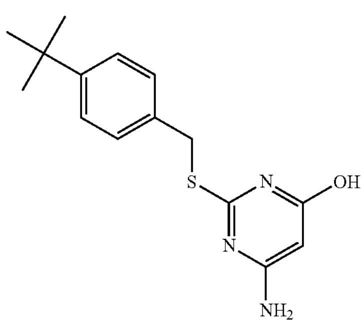 [SMILES: CC(C)(C)c1ccc(CSc2nc(N)cc(O)n2)cc1] | 91% at 100 μM | 24 | 140 | 39 | 424 | 68 | 614 |

1357 P Compounds and 1343 and 1568 Compounds

In the tables shown herein, in those embodiments where the nitrogen atom in an amide or thioamide linkage is not shown attached to three atoms, an N—H linkage is intended.

Example 2: In Vitro Binding Studies for Secondary Effects

Compounds can be evaluated for binding to the human ether-a-go-go potassium channel (hERG) expressed in HEK293 cells by displacement of $^3$[H]-astemizole according to the methods by Finlayson et al. (K. Finlayson., L. Turnbull, C. T. January, J. Sharkey, J. S. Kelly; [$^3$H] Dofetilide binding to HERG transfected membranes: a potential high throughput preclinical screen. *Eur. J. Pharmacol.* 2001, 430, 147-148). Compounds can be incubated at 1 or 10 μM final concentration, in duplicate, and the amount of displaced $^3$[H]-astemizole determined by liquid scintillation spectroscopy. In some cases, a seven concentration (each concentration in duplicate) displacement curve can be generated to determine an $IC_{50}$. Binding to the rat alpha-1 adrenergic receptor in rat brain membranes can be determined by displacement of $^3$[H]-prazosin (P. Greengrass and R. Bremner; Binding characteristics of $^3$H-prazosin to rat brain a-adrenergic receptors. *Eur. J. Pharmacol.* 1979, 55: 323-326). Compounds can be incubated at 0.3 or 3 μM final concentration, in duplicate, and the amount of displaced $^3$[H]-prazosin determined by liquid scintillation spectroscopy. Binding $IC_{50}$ values can be determined from displacement curves (four-six concentrations, each concentration in duplicate) fit by a non-linear, least squares, regression analysis using MathIQ (ID Business Solutions Ltd., UK). The binding Ki's can be determined from the $IC_{50}$ according to the method of Cheng and Prusoff (Y. Cheng and W. H. Prusoff; Relationship between the inhibition constant (K1) and the concentration of inhibitor which causes 50 percent inhibition ($IC_{50}$) of an enzymatic reaction. *Biochem. Pharmacol.* 1973, 22: 3099-3108).

Example 3: Metabolic Stability

Compounds can be incubated with pooled human (from at least 10 donors) or rat liver microsomes, 1.0 mg/ml microsomal protein, and 1 mM NADPH, in buffer at 37° C. in a shaking water bath according to the method of Clarke and Jeffrey (S. E. Clarke and P. Jeffrey; Utility of metabolic stability screening: comparison of in vitro and in vivo clearance. Xenobiotica 2001. 31: 591-598). At 60 min the samples can be extracted and analyzed for the presence of the parent compound by LC-MS/MS. The parent material remaining in the sample at 60 min can be compared to that at 0 min and expressed as a percentage. A control compound, testosterone, can be run in parallel.

Rats (n=3 per dose) can be administered compounds at doses of 1-4 mg/kg in a single bolus i.v. infusion (2 ml/kg body weight) via the tail vein formulated in 2% dimethyl acetamide/98% 2-hydroxy-propyl cyclodextrin (5%). Animals can be fasted overnight prior to dose administration and food returned to the animals two hours after dosing. Following IV dosing, blood samples (ca 200 μL) can be collected into separate tubes containing anticoagulant (K-EDTA) via the orbital plexus at various times post administration. Plasma samples can be prepared immediately after collection by centrifugation for ten minutes using a tabletop centrifuge, and stored at −80° C. Brain tissue can be weighed, homogenized on ice in 50 mM phosphate buffer (2 ml per brain) and the homogenate stored at −80° C. Plasma and brain homogenate samples can be extracted by the addition of 5 volumes of cold acetonitrile, mixed well by vortexing and centrifuged at 4000 rpm for 15 minutes. The supernatant fractions can be analyzed by LC-MS/MS operating in multiple reaction monitoring mode (MRM). The amount of parent compound in each sample can be calculated by comparing the response of the analyte in the sample to that of a standard curve.

Example 5: High Throuphut Screening Assay

A high throughput bioassay was developed to identify modulators that are selective for NR2C- or NR2D-containing receptors. NR2C or NR2D-containing recombinant NMDA receptors show little desensitization and are $Ca^{+2}$ permeable—two properties that renders them amenable to optical assays that measure agonist-induced $Ca^{+2}$ accumulation in mammalian cells using multi-well formats.

The high throughput bioassay used a commercially-available BHK-21 cell line expressing NR1 under control of the Tet-On system (Clontech) (Hansen et (12008) to create two new cell lines that constitutively express either NR2C or NR2D. FIG. 4A illustrates vector design for the NR2D cell line. A similar strategy was employed for the NR2C cell line, except that the NR2C cDNA replaced the NR2D cDNA.

Stable expression of NMDA receptor subunits is cytotoxic. To avoid this toxicity, the culture media was supplemented with NMDA receptor antagonists (200 μM DL-APV and 200 μM 7Cl-kynurenate), and functional NR1 expression was induced by doxycyclin 48 hours prior to assay (FIG. 5B). Fura-2 $Ca^{+2}$ imaging of the functional response of the NR1/NR2D cell line (FIG. 5C) produced a glutamate $EC_{50}$ value (340 nM) that was similar to that measured from two-electrode voltage-clamp assay (460 nM), suggesting this cell line faithfully reproduces NR1/NR2D properties. The BHK cell line expresses a low affinity glutamate transporter system ($K_m$ ~40 μM) which should help keep glutamate concentration low and reduce cytotoxicity due to NMDA receptor over-activation (Scott & Pateman, 1978; Arathoon & Telling, 1981).

In addition, these cells adhere tightly to the culture plastic, allowing thorough washing of antagonists present during culture without losing cells from the bottom of the dish. However, BHK cells can extrude a low level of glutamate through the reversal of the transporter when glutamate is absent from the extracellular solution, such as during wash and dye loading.

Because glutamate activates NR2D-containing receptors with submicromolar $EC_{50}$ (<500 nM), even tens of nanomolar concentrations of glutamate (plus trace glycine) extruded by BHK cells from time of washing through dye loading are sufficient to activate NR1/NR2D receptors, injure cells, and compromise subsequent assays. This toxic activation also creates a high baseline $Ca^{+2}$ signal, which compromises the signal to noise ratio.

To circumvent this problem, we removed cells from the incubator, washed out all antagonists, and subsequently added the competitive glycine site antagonist 7-Cl-kynurenate (30 μM) during the dye loading protocol. This involved adding a cell permeant $Ca^{2+}$ sensitive dye for 10-30 minutes before experimentation. This relatively low affinity antagonist enhances cell health during dye loading and experimental setup by preventing continual NR1/NR2D receptor or NR1/NR2C receptor activation by low levels of glutamate extruded by BHK cells. At the time of the assay, 30 μM of the competitive glycine site antagonist 7-Cl-kynurenate is easily displaced by addition of an excess of glycine (1 mM) together with glutamate (100 μM; FIG. 5A).

The presence of antagonist improved the reliability and the signal-to-noise ratio for the assay.

In another embodiment, however, one could alternatively add a competitive glutamate site antagonist and, when the assay is performed, the competitive glutamate site antagonist is displaced by adding an excess of glutamate together with glycine to improve the reliability and the signal-to-noise ratio for the assay.

We varied plating density, culture time, induction time, DMSO content, agonist concentration. $Ca^{2+}$ concentration, fluorescent dye loading conditions, recording duration, and other parameters to reduce well-to-well variability. Z' values are a standard measure of variability for multi-well assays, with values above 0.5 considered a good indication that an assay is suitable for single well screening of test compounds (Zhang et al. 1999).

$$Z'=1-3'(SD_{signal}+SD_{baseline})/A_{signal}-A_{baseline}$$

Our assay always yielded a favorable value for Z' (0.4-0.8). Real time $Ca^{+2}$ signals were recorded in 96 well plates using a pair of FlexStation II multi-mode plate readers. The assay was designed to identify non-competitive modulators of NR2D-containing receptors by using supramaximal concentrations of glutamate and glycine.

We validated our assay using the commercially available Lopac library (1200 compounds) and our own focused library (~500 biaryl nitrogen-containing compounds with ring systems separated by a defined distance); these two libraries contained a number of known NMDA receptor antagonists in addition to several unpublished NMDA receptor potentiators that we had previously identified. Test compounds were added to each well together with agonist to yield a final well concentration of 10 μM test compound in 0.9% DMSO.

Compounds that altered the response of any well compared to on-plate control wells beyond 2.5-fold of the standard deviation (calculated from all wells on the plate) and by more than 40% of the control response on a given plate were selected for secondary screening using two-electrode voltage-clamp recordings from *Xenopus* oocytes expressing recombinant NR1/NR2D receptors.

An NR1/NR2C expressing cell line was made using similar methods, optimized for single well screening, and tested for sensitivity to known NMDA antagonists. The results obtained confirmed that the NR1/NR2C cell line was also well-suited for high-throughput screening.

Having hereby disclosed the subject matter of the present invention, it should be apparent that many modifications, substitutions, and variations of the present invention are possible in light thereof. It is to be understood that the present invention can be practiced other than as specifically described. Such modifications, substitutions and variations are intended to be within the scope of the present application.

The invention claimed is:

1. A pharmaceutical composition comprising a compound of the following formula:

or pharmaceutically acceptable salts or esters thereof wherein, $R_1$, $R_3$, and $R_4$ are selected independently from H, OMe, OH, SH, SMe, Cl, F, I, Br, $C_{1-6}$ alkyl, $C_{6-10}$ aryl, alkylaryl, and arylalkyl;

$R_2$, is hydrogen;

$R_5$ is a meta or para substituent and are selected independently from OMe, OH, SH, SMe, Cl, F, I, Br, —C(CH$_2$)OMe, C(O)OMe, ethyl, $C_{6-10}$ aryl, alkylaryl, and arylalkyl;

$R_6$ is selected independently from H, OMe, OH, SH, SMe, I, Br, $C_{1-6}$ alkyl, $C_{6-10}$ aryl, alkylaryl, and arylalkyl;

X is O; and

Y is selected from S and O.

2. A pharmaceutical composition comprising a compound of the following formula:

or pharmaceutically acceptable salts or esters thereof wherein, $R_1$, $R_3$ and $R_4$, are selected independently from H, OMe, OH, SH, SMe, Cl, F, I, Br, $C_{1-6}$ alkyl, $C_{6-10}$ aryl, alkylaryl, and arylalkyl;

$R_2$ is hydrogen;

$R_5$ is a meta or para substituent and are selected independently from OMe, OH, SH, SMe, Cl, F, I, Br, —C(CH$_2$)OMe, C(O)OMe, ethyl, $C_{6-10}$ aryl, alkylaryl, and arylalkyl;

$R_6$ is meta substituted OH, CF$_3$, OMe, Br, or I;

X is O; and

Y is selected from S and O.

3. The pharmaceutical composition of claim 1, wherein $R_3$ is methoxy.

4. The pharmaceutical composition of claim 2, wherein $R_3$ is methoxy.

* * * * *